(12) United States Patent
Blak et al.

(10) Patent No.: US 9,708,582 B2
(45) Date of Patent: Jul. 18, 2017

(54) METHOD OF DIFFERENTIATING STEM CELLS

(71) Applicant: STEMCELL TECHNOLOGIES INC., Vancouver (CA)

(72) Inventors: Alexandra A. Blak, Frechen (DE); Sharon A. Louis, Vancouver (CA); Michael John Riedel, Vancouver (CA)

(73) Assignee: Stemcell Technologies Inc., Vancouver, British Columbia (CA)

( * ) Notice: Subject to any disclaimer, the term of this patent is extended or adjusted under 35 U.S.C. 154(b) by 0 days.

(21) Appl. No.: 13/829,783

(22) Filed: Mar. 14, 2013

(65) Prior Publication Data

US 2013/0224857 A1 Aug. 29, 2013

Related U.S. Application Data

(63) Continuation-in-part of application No. 12/903,521, filed on Oct. 13, 2010.

(60) Provisional application No. 61/354,947, filed on Jun. 15, 2010, provisional application No. 61/251,130, filed on Oct. 13, 2009.

(51) Int. Cl.
*C12N 5/071* (2010.01)
*C12N 5/0735* (2010.01)
*C12N 5/0797* (2010.01)

(52) U.S. Cl.
CPC ......... *C12N 5/0608* (2013.01); *C12N 5/0606* (2013.01); *C12N 5/0623* (2013.01); *C12N 2500/60* (2013.01); *C12N 2500/90* (2013.01); *C12N 2500/92* (2013.01); *C12N 2500/98* (2013.01); *C12N 2502/13* (2013.01); *C12N 2506/02* (2013.01); *C12N 2509/00* (2013.01); *C12N 2533/32* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 5,221,537 A | 6/1993 | Hecht et al. | |
| 2006/0040385 A1 | 2/2006 | Itskovitz-Eldor et al. | |
| 2008/0286862 A1 | 11/2008 | Ludwig et al. | |
| 2009/0023208 A1* | 1/2009 | Thomson et al. | 435/366 |
| 2009/0068741 A1* | 3/2009 | Wu | C12N 5/0018 435/440 |
| 2010/0081200 A1* | 4/2010 | Rajala | C12N 5/0606 435/377 |
| 2011/0086379 A1* | 4/2011 | Blak et al. | 435/29 |
| 2011/0269233 A1* | 11/2011 | Malphettes | C12N 15/63 435/440 |

FOREIGN PATENT DOCUMENTS

| | | | |
|---|---|---|---|
| WO | 02/09733 | 2/2002 | |
| WO | WO 2007/050043 * | 5/2007 | ............... C12N 5/06 |
| WO | 2008065381 | 6/2008 | |
| WO | WO2008085879 A2 | 7/2008 | |
| WO | WO2008148938 A1 | 12/2008 | |
| WO | WO 2011044684 * | 4/2011 | ........... C12N 5/0735 |

OTHER PUBLICATIONS

Muhammad Arshad S. Chaudry "Analysis of Stem and Progenitor Cell Responses to variations in Bioprocess Culture Variables" A Thesis from the University of British Columbia, Aug. 2006. pp. 1-212.*
http://tools.lifetechnologies.com/content/sfs/brochures/LowOsmoLP.pdf, Invitrogen, 2006, pp. 1-2.
Chaudhry M A et al., "Culture pH and Osmolality Influence Proliferation and Embryoid Body Yields of Murine Embryonic Stem Cells", Biochemical Engineering Journal, Elsevier, vol. 45, No. 2, Jul. 15, 2009, pp. 126-135.
Waymouth, C., et al. "Osmolality of Mammalian Blood and of Media for Culture of Mammalian Cells", In Vitro, vol. 6, No. 2, 1970, pp. 109-127.
Itskovitz-Eldor, J., et al. "Differentiation of human embryonic stem cells into embryoid bodies compromising the three embryonic germ layers." Molecular Medicine. Feb. 2000;6(2):88-95.
Swistowski, A., et al. "Xeno-free defined conditions for culture of human embryonic stem cells, neural stem cells and dopaminergiv neurons derived from them." PloS One. Jul. 2009, 4(7):e6233 (1-11).
Ungrin, M.D., et al. "Reproducible, ultra high-throughput formation of multicellular organization from single cell suspension-derived human embryonic stemm cell aggregates." PloS One. Feb. 2008;3(2): e1565 (1-12).
Knockout(TM) D-MEM. Certificate of Analysis, Datasheet (online). Invitrogen Corporation. 2002 [Retrieved from the internet, Jan. 27, 2011].
Knockout(TM) SR. Certificate of Analysis, Datasheet (online). Invitrogen Corporation. 2002 [Retrieved from the internet, Jan. 27, 2011].
DMEM-F-12 (1X). Certificate of Analysis, Datasheet (online). Invitrogen Corporation. 2002 [Retrieved from the internet, Jan. 27, 2011].

(Continued)

*Primary Examiner* — Laura Schuberg
(74) *Attorney, Agent, or Firm* — Robert C. Netter, Jr.; Dann, Dorfman, Herrell and Skillman

(57) ABSTRACT

The present disclosure provides methods of generating germ layers from stem cells comprising culturing the stem cells in a culture media having osmolality ranges that promote the generation of specific germ layer progenitor cells. The present disclosure also includes a method to generate different cell lineages from the germ layers as well as to detect them by immunological methods. The present disclosure further provides methods for the generation, isolation, cultivation and propagation of committed progenitor cells and for the production of differentiated cells from the three germ layers. The present disclosure also provides culture media and kits for use in inducing the three germ layers.

28 Claims, 47 Drawing Sheets

(56) References Cited

OTHER PUBLICATIONS

Neurobasel(TM)—A Medium (1X). Certificate of Analysis, Datasheet (online). Invitrogen Corporation. 2003 [Retrieved from the internet, Jan. 27, 2011].

Stempro Accutase Cell Dissociation Reagent. Certificate of Analysis, Datasheet (online). Invitrogen Corporation. Mar. 2009 [Retrieved from the internet, Jan. 27, 2011].

Lonza X-Vivo 10 Serum-free Medium, Product Catalog (online). Fischer Scientific Corporation [Retrieved from the internet, Jan. 27, 2011].

Blak, A., et al. "Generation and Culture of human embryoid bodies (EBs) using AggreWell 400 and a novel neural introduction medium." Society for Neuroscience Annual Meeting Oct. 17, 2009. Poster Presentation.

Blak, A., et al. "Efficient production of neural progenitors from human pluripotent stem cells using a novel neural induction culture system." ISSCR 8th Annual Meeting. Presentation on Jun. 18, 2010. Description—Commercial Tutorial submitted to ISSCR on Mar. 31, 2013.

Van De Lavoir, M.C., et al. "Avian embryonic stem cells." Methods in Enzymology. 2006;418:38-64.

Nat, R., et al. Neurogenic neuroepithelial and radial glial cells generated from six human embryonic stem cell lines in serum-free suspension and adherent cultures. Glia. 2007;55(4):385-399.

Dhara et al., "Neural Differentiation of Human Embryonic Stem Cells", Journal of Cellular Biochemistry, 2008, vol. 105, pp. 633-640.

Smukler, S.R., et al., "Embryonic Stem Cells Assume a Primitive Neural Stem Cell Fate in the Absence of Extrinsic Influences," J. Cell Biol. (2006) 172:79-90.

* cited by examiner

| Condition | | Rosette / Total |
|---|---|---|
| 270 mOsm | 2000 cells/EB | 120 / 120 = 100% |
| 320 mOsm | 2000 cells/EB | 14 / 146 = 10% |
| 340 mOsm | 2000 cells/EB | 8/ 84 = 10% |
| 400 mOsm | 2000 cells/EB | 0 / 174 = 0% |
| 450 mOsm | 2000 cells/EB | Visual: 0% |

| Day EBs were released from microwell | Day NPCs were isolated from attached EBs | Total no of days at dissociation | No of cells per EB | Day picture of NPCs was taken (total no of days in culture) |
|---|---|---|---|---|
| d5 | d6 | d11 | 5000 | D6 (17) |
| d5 | d7 | d12 | 10000 | D6 (18) |
| d6 | d8 | d14 | 10000 | D6 (20) |
| d11 | d5 | d16 | 2000 | D5 (21) |
| d7 | d11 | d18 | 2000 | D4 (22) |
| d9 | d9 | d18 | 2000 | D4 (22) |
| d11 | d7 | d18 | 2000 | D4 (22) |
| d5 | d7 | d12 | 5000 | D6 (18) |

B.

A.

A. A13700

B. H1

METHOD OF DIFFERENTIATING STEM CELLS

RELATED APPLICATIONS

This application is a continuation-in-part of U.S. application Ser. No. 12/903,521 filed Oct. 13, 2010 (now pending), which claims the benefit of priority of U.S. provisional application No. 61/354,947 filed Jun. 15, 2010 and No. 61/251,130 filed Oct. 13, 2009, all of which are incorporated herein by reference in their entirety.

FIELD OF THE DISCLOSURE

The disclosure relates to methods of differentiating stem cells into germ layers and further into cell lineages. The disclosure also relates to media for said differentiation.

BACKGROUND OF THE DISCLOSURE

Human embryonic stem (ES) cells are pluripotent cells isolated from developing blastocysts. Induced pluripotent stem cells (iPS cells) are pluripotent cells originally isolated from somatic cells of the body reprogrammed by genetic and non-genetic approaches (for review see Amabile and Meissner, 2009). While iPS cells share many characteristics of ES cells including the ability to be differentiated in vitro to cells of all three germ layers, they are not identical. Genetic and epigenetic differences between these two cell types have been reported in the literature and these differences may contribute to altered differentiation efficiencies when subjected to in vitro differentiation protocols. ES cells as well as iPS cells serve as an excellent in vitro system for studying differentiation events and as unlimited source for generating various specialized cell types in large quantities for basic research, drug screening and regenerative therapeutic applications.

Protocols to induce a certain germ layer cell type and subsequent definitive tissue types from human pluripotent stem cells, which includes human embryonic stem cells and induced pluripotent stem cells, are numerous, diverse and currently not standardized. They commonly involve differentiation using 3 major categories of protocols (for a review see Murry and Keller, 2008):

1. Based on co-culture of pluripotent stem cells with other cell types such as feeder cells (e.g. D'Amour et al., 2005, Perrier et al., 2005) or a somatic cell type (eg. induction of cardiomyocytes via co-culture with murine endoderm-like cell lines (Mummery et al., 2007); in medium conditioned by the feeder cells, which induces a certain germ layer fate (Schulz et al., 2003) or alternatively with the addition of factors (D'Amour et al., 2005);
2. Based on adherent culture as monolayers with or in the absence of serum and including the addition of morphogens (Nat et al., 2007; Chambers et al., 2009). Monolayer cultures of pluripotent stem cells can be achieved by dissociating pluripotent stem cells to single cells and then plating those single cells on a coated or uncoated culture surface. Typically, pluripotent stem cells are plated onto culture surfaces that have been precoated with extracellular matrix proteins or synthetic peptides that promote the attachment and survival of pluripotent stem cells. Common proteins and peptides that support this attachment and survival are generally known to those in the field and include for example Matrigel™, vitronectin, E-Cadherin, and laminin. Synthetic peptides that can serve as substrates for pluripotent stem cells are also known to those in the field and can include for example integrin-binding RGD peptides. Additionally, cells can be seeded onto synthetic or biological scaffolds, including artificial organ scaffolds or de-cellularized organs or tissues. Generally, single cells are plated at a known density yielding a monolayer of a defined confluence. There is evidence that cell plating densities can affect cultured cells by influencing cell growth, death, and differentiation. For example, plating efficiency of human pluripotent stem cells is improved if single cells are plated at higher density or if the cells are maintained as clumps where localized areas of high density can improve cell survival. Many protocols for the differentiation of pluripotent stem cells to more specified lineages require plating of pluripotent stem cells at a particular confluence. Confluence is typically assessed by the user by visually assessing the percentage of the culture surface covered by the adherent cells. For example, a 50% confluent culture would appear to have adhered cells covering half of the area of the culture surface. A 100% confluent culture would appear to have cells covering the entire culture surface. Confluence therefore does not indicate a particular number of cells given that cells can be of different size (the same number of smaller cells will cover less area than larger cells) or may spread out on a culture surface to different degrees. Pluripotent stem cells can also be plated as clumps or aggregates of 2 or more cells adhered to each other. These clumps also require similar attachment substrates to those required for single pluripotent stem cells. These clumps are typically multilayered and confluence of these cultures is assessed again by estimating the percentage of the culture surface that is not covered by these adhered clumps. Cultures can also be stacked on top of one another to create multilayered or 3-dimensional cultures. In this type of culture system, cells from one monolayer can either be directly in contact with the adjacent monolayer, or the monolayers can be separated from each other by a matrix or other biological or physical barrier;
3. Based on the formation of 3-D aggregates called embryoid bodies (EBs). Cells in the EBs are multipotential, with the propensity to develop into cells of any of the 3 germ layers (endoderm, mesoderm or ectoderm) (Odorico et al., 2001). Usually morphogens are also added either directly at the time of EB formation to serve as inductive cues or at a later time-point (e.g. after plating of the EBs) to selectively support survival of or differentiation to the desired cell lineage (see embryonic stem cell protocols). EBs can be cultured in suspension, for example in ultra-low adherent culture plates or in bioreactors, or they can re-adhered to a culture surface.

The major disadvantages of these protocols can be summarized as follows. Exact protocol details can vary significantly between different labs as well as different operators within a single lab. In addition, protocol efficiencies can vary among different cell lines and within the same cell line if cultured using alternate methods. Thus reproducing published or disclosed protocols can require significant optimization. Media formulations used in the 3 different categories of protocols above consist of a variety of media components, additives, and supplement mixtures that are not consistent between labs and protocols. Detailed lists of the individual components in culture medium and their working concentrations are very often not available especially when premixed supplements from commercial vendors are used.

The cultures derived from pluripotent stem cells even under the most defined conditions, are inherently heterogeneous, consisting of cell types of different lineages and at different stages of development. Heterogeneity may be explained by intrinsic cell-to-cell signaling and the variations in the time points used when manipulating the cells in some of the protocols. One solution that has been applied to increase the percentages of the desired cell type that are being induced is the use of morphogens like cytokines or growth factors as additives to the medium. These can be very costly and variable depending on the source.

The method of culturing human pluripotent stem cells can have a significant impact on the ability of those cells to respond to differentiation cues. There are several methods for culturing human pluripotent stem cells including the use of specialized media with (feeder-dependent) or without (feeder-free) co-culture with mouse or human irradiated fibroblasts. Several home-made and commercial media have been developed to promote the maintenance of the pluripotent state in human pluripotent stem cells including KO-DMEM+Knock Out Serum Replacer (KOSR), conditioned medium from irradiated feeder cells, mTeSR™ 1 (STEMCELL Technologies, Inc., Cat #05850, 2008), TeSR™-E8™ (STEMCELL Cat #05840, 2012), Essential-8™ (Life Technologies, Inc., Cat #A14666SA, 2012) and others. Use of each of these specialized media can result in the propagation of human pluripotent stem cells with somewhat different phenotypes. The culture media used to maintain human pluripotent stem cells can therefore affect the ability of these cells to differentiate in response to a given stimulus. For example, human pluripotent stem cells cultured in mTeSR™ 1 are able to respond to the commercially available STEMdiff™ Definitive Endoderm Kit (STEMCELL Technologies, Inc., Cat #05110, 2012) with highly efficient differentiation towards definitive endoderm. Human pluripotent stem cells cultured in TeSR™-E8™ or Essential 8™ are not routinely able to differentiate with high efficiency to definitive endoderm using the STEMdiff™ Definitive Endoderm Kit. Therefore this indicates that there are inherent differences in the functional properties of the stem cells cultured using these different pluripotency or maintenance media which effect their downstream differentiation potential.

Another common approach to control for heterogeneity is the use of selection strategies to obtain the desired cell types, such as mechanical selection or promotion of selective survival using certain media supplements and factors. Mechanical selection can be very tedious and also hardly gives rise to an entirely pure population of desired cell types. A major drawback of using certain supplements for the induction of cell types (e.g. N2 supplement for neural induction) is the interference with cell survival at later stages of the protocol when actual progenitor cells are isolated (Dhara et al., 2008).

Another disadvantage of many protocols is the amount of time it takes to obtain a pure differentiated cell population, especially when the protocol is multi-stepped and includes selection strategies as described above. The entire procedure may take up to several weeks.

Differentiated cell types derived from human pluripotent stem cells are the object of therapeutic approaches such as cell transplantations. Current research aims are focusing on the removal of animal derived proteins from human pluripotent stem cell cultures and differentiated lineages (Mallon et al., 2006). In many current protocols, so-called feeder cells used for the induction of germ layers are commonly derived from mouse tissues. In addition, differentiation of EBs especially into mesoderm often involves the use of fetal bovine serum in culture media, which is a non-characterized animal derived product.

Cell plating densities in monolayer cultures are often not well defined in many protocols and might influence the percentages of the desired cell types induced due to cell intrinsic signaling as described above. Early induction events may also be potentially influenced using differentiation protocols based on EB formation, which deal with variability in EB size and shape.

There is some evidence in the literature that the osmolality of the culture medium influences cell proliferation, survival and differentiation. For example, the osmolality of mTeSR™ 1 medium was adjusted to a higher osmolality of 340 mOsm/kg compared to more standard osmolality of 290-330 mOsm/kg used in most cell culture media to better maintain the undifferentiated state of human ES cells (Ludwig et al., 2006). On the other hand, differentiated cell types such as primary neurons isolated from the CNS survive better in medium with low osmolality (230-280 mOsm/kg) compared to standard osmolality (Brewer et al., 1993; Brewer and Price 1996; Kivell et al., 2000). The available information suggests that a specific osmolality is either effective for maintaining cells in the undifferentiated state, promoting survival or maintaining already differentiated cells or mature cells in the differentiated state.

The lack of standardization of protocols for the differentiation of pluripotent stem cells has also been discussed widely in the literature (for a review see Sanchez-Pernaute and Sonntag, 2006).

Human ES cells are able to give rise to neural tissue in vitro either
1. Directed by an activity inherent to certain embryonic fibroblast cells of murine or human origin. This activity is referred to as stromal derived inducing activity or SDIA (Perrier et al., 2004, Sonntag et al., 2007);
2. Spontaneously under adherent conditions as monolayers as clumps or single cells and with the addition of supplements such as N2 and B27 (Nat et al., 2007) or directed by addition of morphogens (Osafune et al., 2007);
3. Spontaneously as an aggregated mass of differentiating cells known as embryoid bodies (EBs), which is believed to occur because of the presence of inductive factors inside of the EB mimicking the events taking place in the early embryo. These EBs contain cells of all three germ layers, including neuronal cells of the ectodermal lineage (Odorico et al., 2001, Zhang et al., 2001, Yan et al., 2005).

To date, all three of the foregoing methods of inducing neuroectoderm are inefficient and lead to heterogeneous populations of cells, many of which are non-neural.

However, higher efficiencies in neural/neuronal differentiation were achieved when human embryonic stem cells (hESCs) were exposed to morphogens like retinoic acid (Schuldiner et al., 2001), Fgf2 (Zhang et al., 2001), conditioned medium (Schulz et al., 2003; Shin et al., 2006), bone morphogenetic protein (BMP) inhibitors (Itsykson et al., 2005, Gerrard et al., 2005, Sonntag et al., 2007) or SMAD signaling inhibitors such as SB431542 (Chambers et al., 2009; Kim et al., 2010).

Although these protocols increase the emergence of neural cells, a subsequent selection of neural cells from this mixture had to be utilized in a majority of these protocols in order to obtain relatively pure populations of neuronal cells from differentiating cultures of ES cells. In vitro, early emerging neural progenitor cells are morphologically distinct from other cell types and are characterized by the formation of radially organized columnar epithelial cells termed "neural rosettes" (Zhang et al. 2001, 2005; Elkabetz et al., 2008). These structures comprise cells expressing early neuroectodermal markers such as Pax6 and Sox1 and are capable of differentiating into various region-specific neuronal and glial cell types in response to appropriate developmental cues (Yan et al., 2005, Perrier et al. 2004; Li et al. 2005). Over time in culture, the Pax6 positive cells down-regulate Pax6 expression and maintain Sox1 expression. However, they also begin to express Nestin. Similar protein expression profiles are observed in in vivo neural development when comparing neural precursors at the neural plate stage versus neural precursors emerging after neural tube closure (Jessell 2000). Currently, Nestin and Sox1 protein co-expression as well as formation of "neural rosettes" are considered a reliable criterion for the detection of neural progenitor cells (Elkabetz et al., 2008; Elkabetz and Studer 2009; Koch et al., 2009; Peh et al. 2009).

The controlled differentiation of human pluripotent cells into pure or highly enriched population neural progenitor cells and subsequent differentiation of these cells into the 3 cell types of the central nervous system (CNS): neurons, astrocytes and oligodendrocytes without any additional selection procedure would be highly desirable in the field since all these cell populations would provide real advantages for basic and applied studies of CNS development and disease.

To summarize, the field is lacking a standardized media formulation(s) and protocol(s) to induce the 3 germ layers and subsequently more specialized cell types derived thereof in a short period of time. The field also suffers from the lack of standardized protocols which are easy to reproduce in different labs and operator-independent. Furthermore, the field suffers from a lack of formulation(s) and protocol(s) that allow for efficient differentiation to the 3 germ layers or to a specific germ layer from pluripotent stem cells which are cultured under varying maintenance or pluripotency culture conditions.

SUMMARY OF THE DISCLOSURE

The present inventors have addressed some of the major limitations in the field of pluripotent stem cell differentiation by developing media formulation(s) that allow one to obtain the desired differentiated cell type in a selective and standardized manner. The present inventors have shown that early induction of the 3 germ layers: mesoderm, ectoderm and endoderm from undifferentiated pluripotent stem cells, can be biased by manipulating the osmolality of the culture medium. Such media allows highly efficient generation of germ layer progenitor cells under serum- and feeder-free culture conditions.

Accordingly, the present disclosure provides a method of generating a population of germ layer progenitor cells comprising culturing stem cells in culture media with an osmolality of 260 to 550 mOsm/kg, optionally 260 to 340 mOsm/kg or 320 to 550 mOsm/kg, 350 to 450 mOsm/kg, above 340 mOsm/kg or about 365 mOsm/kg and allowing the cells to differentiate into germ layer progenitor cells.

In an embodiment, the present disclosure provides a method of generating a population of germ layer progenitor cells comprising:
(a) dissociating pluripotent stem cells into clusters or single cells;
(b) culturing the dissociated cells from a) in culture media with an osmolality of 260 to 550 mOsm/kg; and
(c) differentiating the cells of b) into germ layer progenitor cells.

In an embodiment, for differentiating to endoderm progenitor cells, the cells are cultured in (b) for 16-60 hours in a microwell device, in suspension or adhered to a culture plate. In another embodiment, for differentiating to endoderm progenitor cells, the cells are cultured in (b) for about 24 hours in a microwell device, in suspension or adhered to a culture plate. In yet another embodiment, for differentiating to endoderm progenitor cells, the cells are cultured in (b) for about 48 hours in a microwell device, in suspension or adhered to a culture plate.

In one embodiment, differentiating the cells in (c) comprises dissociating the cells of b) and plating the cells onto coated culture dishes and culturing for at least 1 day in the culture media to produce germ layer progenitor cells.

In one embodiment, for ectoderm differentiation, culturing the dissociated cells in b) comprises culturing the dissociated cells from a) in a microwell device for about 24 hours to form aggregates and continuing the culture in the microwell device for more than 24 hours in the culture media followed by releasing the aggregates and adhering onto coated culture dishes and culturing in the culture media for at least 1 day. In one embodiment, the aggregates are cultured in the microwell device for up to 14 days, optionally 5-6 days, prior to releasing the aggregates and adhering onto the coated culture dishes. In another embodiment, the aggregates are cultured in the microwell device for up to 11 days.

In another embodiment, for ectoderm differentiation, culturing the dissociated cells in b) comprises culturing the dissociated cells from a) in the culture media in a microwell device for about 24 hours to form aggregates, releasing the aggregates from the microwell device, followed by culturing the released aggregates in suspension in the culture media for at least 1 day, dissociating and adhering the aggregates onto coated culture dishes and culturing in the culture media for at least 1 day. In one embodiment, the cells are cultured in suspension for up to 14 days, optionally 5-6 days, before dissociating and adhering the aggregates onto coated culture dishes.

In yet another embodiment, for ectoderm differentiation, culturing the dissociated cells in b) comprises culturing the dissociated cells from a) in suspension in the culture media for at least 1 day followed by dissociating the cells and adhering onto coated culture dishes and culturing in the culture media for at least 1 day. In one embodiment, the cells are cultured in suspension for up to 14 days, optionally 5-6 days, prior to dissociating and adhering onto the coated culture dishes.

In a further embodiment, for ectoderm differentiation, culturing the dissociated cells in b) comprises adhering the dissociated cells from a) onto coated culture dishes and culturing for at least 3 days in the culture media. In one embodiment, the cells are cultured on the coated culture dishes for up to 14 days in the culture media, optionally 5-6 days. In an embodiment, the adhered cells are cultured on feeders.

In one embodiment, for endoderm differentiation, culturing the dissociated cells in b) comprises culturing the dissociated cells from a) in a microwell device for at least 16 hours to form aggregates and continuing the culture in the microwell device in the culture media for up to 60 hours, prior to differentiating the cells in (c).

In an embodiment, for endoderm differentiation, the pluripotent stem cells have been maintained at an osmolality of 260-310 mOsm/kg prior to (a). In such embodiments (b)

comprises culturing the cells in a media of higher osmolality, such as 330-550 mOsm/kg and (c) optionally comprises culturing the cells of (b) in media of lower osmolality, such as 260-360 mOsm/kg, optionally 260-280 mOsm/kg.

In another embodiment, for endoderm differentiation, culturing the dissociated cells in b) comprises culturing the dissociated cells from a) in the culture media in a microwell device for at least 16 hours to form aggregates, releasing the aggregates from the microwell device, followed by culturing the released aggregates in suspension in the culture media for up to 60 hours, prior to differentiating the cells in (c).

In another embodiment, for endoderm differentiation, culturing the dissociated cells in b) comprises culturing the dissociated cells from a) in suspension in the culture media for at least 16 hours followed by dissociating the cells and adhering onto coated culture dishes and culturing in the culture media for up to 60 hours, prior to differentiating the cells in (c).

In yet another embodiment, for endoderm differentiation, culturing the dissociated cells in b) comprises adhering the dissociated cells from a) onto coated culture dishes and culturing for 16-60 hours in the culture media, prior to differentiating the cells in (c). In an embodiment, the adhered cells are cultured on feeders.

In an embodiment, for ectoderm differentiation, the culture media for (b) comprises Dulbecco's minimal essential medium (DMEM) and optionally, further comprises vitamins, trace elements, selenium, insulin, lipids, b-mercaptoethanol, non-essential amino acids, antibiotics, bFGF, B27, N2 or mixtures thereof. In another embodiment, the culture media comprises the components as shown in Table 2.

In an embodiment, the culture media for step (b) for endoderm induction comprises a mixture of DMEM and F-12 and optionally further comprises vitamins, salts, trace elements, selenium, insulin, lipids, proteins, amino acids, TGF-beta, FGF2, or mixtures thereof. In another embodiment, the culture media comprises the components as shown in Table 4.

In one embodiment, the stem cells are mammalian pluripotent stem cells, optionally, human pluripotent stem cells. In another embodiment, the pluripotent stem cells are induced pluripotent stem cells or embryonic stem cells. In yet another embodiment, the germ layer is ectodermal, endodermal and/or mesodermal.

In one embodiment, the aggregates or clusters comprise embryoid bodies. In an embodiment, the embryoid bodies comprise 10 to 20,000 cells, optionally 500 to 20,000 cells.

In one embodiment, the culture medium is 260 to 280 mOsm/kg for use in inducing or enriching for ectodermal progenitor cells when the dissociated cells are first cultured in the microwell device and/or in suspension. In another embodiment, the osmolality of the culture medium is 270 to 320 m mOsm/kg for use in inducing or enriching ectodermal progenitor cells when the dissociated cells are plated directly onto coated culture dishes.

Also provided herein is a method of maintaining single neural progenitor cells in culture media with an osmolality of 260-340 mOsm/kg comprising generating ectodermal progenitor cells according to the methods described herein; dissociating the ectodermal progenitor cells from the cultures; plating and culturing said progenitor cells in the culture media for at least 1 day. In one embodiment, the osmolality is about 270 mOsm/kg. In another embodiment, the culture media comprises bFGF. In yet another embodiment, the progenitor cells are plated and cultured for at least 4 days. In a further embodiment, the ectodermal progenitor cells are further differentiated to form neurons, oligodendrocytes or astrocytes.

In another embodiment, the osmolality of the culture media is above 280 mOsm/kg, optionally 290 to 550, or 290-340 mOsm/kg, for inducing or enriching for endodermal and/or mesodermal progenitor cells when the dissociated cells are first cultured in the microwell device and/or in suspension. In another embodiment, the osmolality of the culture medium is above 320 mOsm/kg, optionally 320 to 340 mOsm/kg, for inducing or enriching for endodermal and/or mesodermal progenitor cells when the dissociated cells are plated directly onto coated culture dishes.

Also provided herein is a method of maintaining single mesodermal and/or endodermal progenitor cells in culture media with an osmolality of 290-340 comprising generating mesodermal and/or endodermal progenitor cells according to the methods described herein; dissociating the mesodermal and/or endodermal progenitor cells from the adhered cultures; and plating and culturing said progenitor cells, optionally in culture media having an osmolality of 260-360 mOsm/kg, optionally 320-340. In an embodiment, the mesodermal and endodermal progenitor cells are further differentiated to form mesenchymal stem cells, chondrocytes, cardiomyocytes, hematopoietic stem cells, skeletal muscle cells, pancreatic cells, lung cells, intestinal cells, or liver cells.

In another embodiment, the osmolality of the culture media in (b) is 320-550 mOsm/kg for generating a population of enriched endodermal progenitor cells.

In yet another embodiment, the osmolality of the culture media in (b) is 350-450 mOsm/kg for generating a population of enriched endodermal progenitor cells.

In yet a further embodiment, the osmolality of the culture media in (b) is about 365 mOsm/kg for generating a population of enriched endodermal progenitor cells.

In yet another embodiment, the culture medium is 320 to 550 mOsm/kg in (b) for use in inducing or enriching for endodermal progenitor cells when the dissociated cells are first cultured in the microwell device and/or in suspension. In another embodiment, the osmolality of the culture medium is 320-550 mOsm/kg in (b) for use in inducing or enriching endodermal progenitor cells when the dissociated cells are plated directly onto coated culture dishes.

In some embodiments, the pluripotent stem cells are first cultured in a medium that supports the maintenance of undifferentiated pluripotent stem cells where that culture medium has an osmolality below 320 mOsm/Kg. Accordingly, in one embodiment, the pluripotent stem cells used to induce or enrich for endodermal progenitor cells have been maintained in a culture media having an osmolality of 260-310 mOsm/kg prior to dissociating the cells of (a). In one embodiment, this culture medium comprises a mixture of DMEM and F-12 and optionally further comprises vitamins, salts, trace elements, selenium, insulin, lipids, proteins, amino acids, TGF-beta, FGF2, or mixtures thereof. In another embodiment, the culture media comprises the components as shown in Table 4. In another embodiment, this culture medium is TeSR™-E8™, Essential 8™, or E8.

In yet another embodiment, the pluripotent stem cells are first cultured in a medium that supports the maintenance of undifferentiated pluripotent stem cells where that culture medium has an osmolality above 320 mOsm/Kg. In one embodiment, this culture medium is mTeSR™ 1, TeSR™ 2, mouse embryonic fibroblast (MEF) conditioned medium, or DMEM+(KOSR).

The medium used in (b) to raise the osmolality of culture for endoderm differentiation is any medium that supports the survival of mammalian cells, that medium having an osmolality greater than 330 mOsm/Kg. In one embodiment, the medium is STEMdiff™ Neural Induction Medium (STEMCELL Technologies, Inc. Cat #05831, 2011) where the osmolality has been adjusted with compounds, for example, sodium chloride to be greater than 330 mOsm/Kg.

In one embodiment, the osmolality of the culture medium is manipulated through the addition of a concentrated supplement. In an embodiment, the concentrated supplement comprises a physiological diluent and a salt, such as sodium chloride and optionally further comprises a protein. In an embodiment, the protein is albumin, optionally albumin is derived from a recombinant source. In an embodiment, the albumin is human recombinant albumin.

In an embodiment, the culture medium used in (c) to differentiate the human pluripotent stem cells to definitive endoderm is STEMdiff™ Definitive Endoderm (STEMCELL Technologies, Inc. Cat #05110) whereby the protocol is followed according to manufacturer's instructions.

In another embodiment, the culture medium used in (c) to differentiate the human pluripotent stem cells to definitive endoderm comprises a basal medium, a TGF-beta superfamily member, an FGF superfamily member, and a Wnt activator (Eg. Rezania et al., 2011).

In yet another embodiment, the culture medium used in (c) to differentiate the human pluripotent stem cells to definitive endoderm comprises a basal medium and a TGF-beta superfamily member (Eg. D'Amour et al., 2005).

In another embodiment, the culture medium used in (c) to differentiate the human pluripotent stem cells to definitive endoderm comprises a basal medium and a molecule that promotes SMAD phosphorylation.

In yet another embodiment, the endodermal progenitor cells are further differentiated to form pancreatic cells, respiratory cells, intestinal cells or liver cells.

In one embodiment, the endoderm cells derived from the pluripotent stem cells express one or more of CXCR4, SOX17, GATA-4, FOXA2, AFP, CER1, C-KIT, EPCAM, SNAI1, GSC, E-Cad, or N-Cad.

Also provided herein are culture media compositions and kits useful for inducing germ layer differentiation and screening assays for agents that can modulate the differentiation of the cells or for primary or secondary screens of the cells generated by the methods described herein.

Accordingly, in one embodiment, the present disclosure provides a kit comprising a medium with an osmolality of between 260 and 310 mOsm/Kg and a concentrated supplement. In an embodiment, the concentrated supplement comprises a physiological diluent and a salt, such as sodium chloride. In another embodiment, the concentrated supplement further comprises a protein. In one embodiment, the protein is albumin, optionally derived from an animal source or a recombinant source, such as human recombinant albumin.

The medium can be any cell culture medium. In one embodiment, the medium is a pluripotent stem cell maintenance medium. In another embodiment, the medium comprises a mixture of DMEM and F-12 and optionally further comprises vitamins, salts, trace elements, selenium, insulin, lipids, proteins, amino acids, TGF-beta, FGF2, or mixtures thereof. In another embodiment, the medium is TeSR™-E8™, Essential 8™, or E8. In yet another embodiment, the medium comprises the components shown in Table 4.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION OF THE DISCLOSURE

Methods of the Disclosure

Inducing Germ Layer Progenitor Cells

Figure 1:
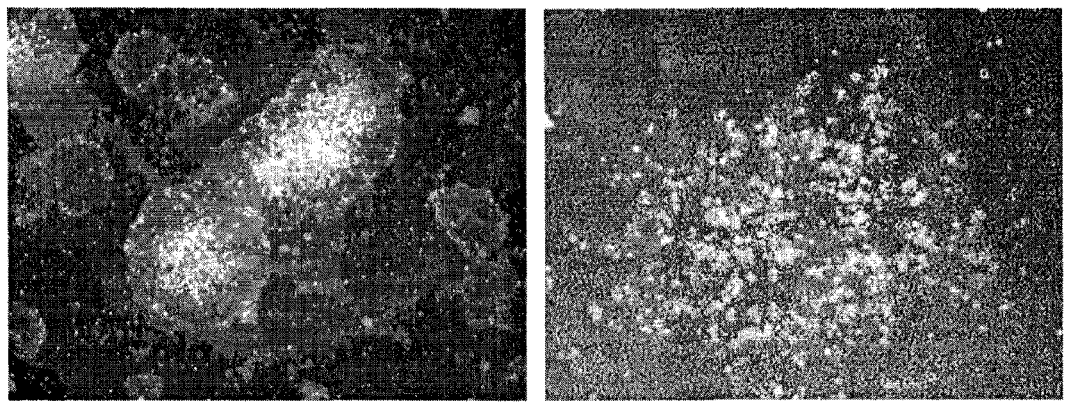
FIG. 1 shows human embryonic stem cells cultured on day 5 of culture on BD Matrigel™ (H9 p51) Magnification: 2× (left), 10× (right).

The present inventors have developed methods of inducing or enriching germ layer progenitor cells by culturing stem cells in media with controlled osmolality.

The phrase "inducing or enriching germ layer progenitor cells" or "generating an enriched population of germ layer progenitor cells" as used herein refers to increasing the population of a particular germ layer progenitor cell by at least 10%, 20%, 30%, 40%, 50%, 60%, 70%, 75%, 80% or more compared to other germ layer progenitor layer cells.

Accordingly, the present disclosure provides a method of generating a population of germ layer progenitor cells comprising culturing stem cells in culture media with an osmolality of 260 to 550 mOsm/kg, optionally 260 to 340 mOsm/kg, 320 to 550 mOsm/kg, 350 to 450 mOsm/kg, above 340 mOsm/kg or about 365 mOsm/kg, and allowing the cells to differentiate into germ layer progenitor cells.

In an embodiment, the present disclosure provides a method of generating a population of germ layer progenitor cells comprising:
(a) dissociating pluripotent stem cells into clusters or single cells;
(b) culturing the dissociated cells from a) in culture media with an osmolality of 260 to 550 mOsm/kg; and
(c) differentiating the cells of b) into germ layer progenitor cells.

In one embodiment, differentiating the cells in (c) comprises dissociating the cells of b) and plating the cells onto coated culture dishes and culturing for at least 1 day, optionally 3-6 days, in the culture media to produce germ layer progenitor cells.

The term "osmolality" as used herein refers to the concentration of a solution in terms of osmoles of solute per kilogram of solvent. Osmoles of solute per kilogram of solvent is equivalent to the number of particles per kg. In this case, it is the concentration of ions (originating from salt: NaCl=2) per kg of solvent, which is double the molality (mol/kg), which refers to molecules/kg. A person skilled in the art would readily be able to determine the amount of salt needed to obtain media of a particular osmolality. An example of such a determination is found in Example 5.

In an embodiment, the osmolality of the culture medium is manipulated through the addition of a concentrated supplement. In one embodiment, the concentrated supplement comprises a physiological diluent, salt, such as sodium chloride, and optionally further comprises a protein. In one embodiment, the protein is albumin, for example from an animal source or recombinant source, optionally human recombinant albumin.

In another embodiment, the osmolality of the culture medium is manipulated by addition of a salt. In an embodiment, the salt is sodium chloride.

Stem cell culture media are known in the art for maintaining stem cells. In one embodiment, the culture media is serum-free. In another embodiment, the culture media comprises Dulbecco's minimal essential medium. Examples of typical culture media include mTeSR™ 1, TeSR™ 2, TeSR™-E8™, Essential 8™, Knockout™ D-MEM with KOSR, ReproFF™, and ReproFF2™ (ReproCell Cat #RCHEMD004, RCHEMD006, 2012). Combinations of these media formulations can be used for mesoderm, ectoderm, and endoderm induction. In one embodiment, the culture media described herein comprises the components shown in Table 4 and the osmolality is adjusted to the desired level by addition of an osmotic modulator such as salt as described herein. In another embodiment, the culture media also comprises albumin.

The term "stem cell" as used herein refers to a cell that has the ability for self-renewal. In one embodiment, the stem cell is a pluripotent stem cell. The term "pluripotent" as used herein refers to an undifferentiated cell that maintains the ability to allow differentiation into various cell types. In one embodiment, pluripotency is determined morphologically for example as described in Example 4. In such an embodiment, a cell is considered pluripotent when the colony the cell is part of displays less than 50% differentiation, less than 30% differentiation, less than 20% differentiation, less than 15% differentiation, less than 10% differentiation, less than 5% differentiation or less than 1% of differentiation. In one embodiment, the pluripotent stem cell is an embryonic stem cell. In another embodiment, the pluripotent stem cell is an induced pluripotent stem cell derived from any somatic cell using genetical or chemical methods.

Embryonic stem cells can be obtained from the inner cell mass of an early mammalian embryo—the blastocyst. Induced pluripotent stem cells (iPSCs) are obtained by re-programming somatic cells of the body. The term "pluripotent stem cells" includes, without limitation, cultured embryonic stem cell lines and induced pluripotent stem cell lines derived from any tissue. Induced pluripotent stem cells can be derived from mammalian cells. Stem cells have also been discovered in non-mammalian sources such as zebra fish, *drosophila* and newts. In one embodiment, the pluripotent stem cells are human.

In one embodiment, the aggregates or clusters are formed in the presence of Y27632 (rock inhibitor), which is added to increase the survival of single stem cells.

The term "aggregate" as used herein refers to one cell attached to another cell or more than one cell attached together or a group of cells attached together. Such aggregates are formed from cells after disruption of confluent or semi-confluent culture of human pluripotent stem cells or from clusters of cells obtained by disruption of confluent or semi-confluent culture of human pluripotent stem cells. The term "embryoid body" or "EB" as used herein refers to a three-dimensional aggregate derived from human pluripotent stem cells. Embryoid bodies are formed using various protocols including scraping of human pluripotent stem cells. Aggregates and embryoid bodies are used interchangeably. However in some instances aggregates will specifically refer to aggregates when using the microwell device called AggreWell™ 400 as shown in Example 7 or AggreWell™ 800 as shown in Example 24. In one embodiment, the embryoid bodies comprise 10 to 20,000 cells, optionally 500 to 20,000 cells.

The term "dissociation" as used herein refers to the breaking up of cell aggregates or clusters into smaller aggregates or different sizes or into a single cell suspension. Dissociation of the cells described herein can be by any method, including, without limitation, non-enzymatic, enzymatic, chemical or mechanical means. In one embodiment, dissociation comprises mechanical means. In another embodiment, dissociation comprises enzymatic means, such as Accutase™ (STEMCELL Technologies Cat #07920, 2007), Dispase™ (STEMCELL Technologies Cat #07923, 2008), Neurocult™ Chemical Dissociation Kit (STEMCELL Technologies Cat #05707, 2005) or trypsin-EDTA (STEMCELL Technologies Cat #07910, 2005). In another embodiment, dissociation comprises non-enzymatic means, such as EDTA or Gentle Cell Dissociation Reagent™ (STEMCELL Technologies Cat #07174, 2012).

In one embodiment, the coated culture dishes comprise factors which promote cell attachment, such as extracellular matrix molecules, synthetic molecules, synthetic peptides or chemical substrates. In another embodiment, the coated culture dishes comprise poly-L-ornithine/laminin, laminin alone or Matrigel. The concentration of laminin is readily determined by a person skilled in the art and includes, 1-20 ug/mL, such as 1 ug/mL, 5 ug/mL, 10 ug/mL or 20 ug/mL. The concentration of poly-L-ornithine is readily determined by a person skilled in the art and includes, 1-100 ug/mL, such as 1 ug/mL, 5 ug/mL, 10 ug/mL or 20 ug/mL. In another embodiment, the coated culture dishes comprise vitronectin, fibronectin, or e-cadherin. The concentrations of these coating can be readily determined by a person skilled in the art. In yet another embodiment, the culture dishes are tissue culture-treated but otherwise uncoated.

The term 3-dimensional as used herein to describe the culture system refers to any orientation of the cultured cells that results in one cell being in direct contact with a substrate and a second cell being in contact with the first cell but not directly with the substrate. In one embodiment, the second cell may be in contact with a substrate that is continuous or not continuous with the substrate that is in contact with the first cell. In an embodiment, the term 3-dimensional refers to cell clumps, aggregates, or embryoid bodies. In some embodiments, this term can refer to multilayered cells adhered to a culture surface such as an artificial scaffold or de-cellularized organ.

The term "differentiation" as used herein refers to the process by which a less specialized cell, such as a stem cell, becomes a more specialized cell type, such that it is committed to a specific lineage including, without limitation, certain progenitor cells as well as more specialized somatic cells. Conditions for differentiation of the stem cells are readily known in the art.

The term "germ layer progenitor cells" as used herein refers to cells that are able to differentiate into the three layers of cells that are formed during mammalian embryogenesis. Accordingly, in one embodiment, the germ layer is ectoderm(al), which refers to the outer germ layer that develops into skin and nervous tissue; endoderm(al), which refers to the inner germ layer that develops into the lining of the digestive and respiratory systems; and/or mesoderm(al), which refers to the middle germ layer that develops into muscle, bone and cartilage and blood and connective tissue.

Ectodermal Differentiation

The present inventors have shown that an ectodermal germ layer can be induced or enriched by culturing the stem cells in a culture media with an osmolality range of 260 to 280 mOsm/kg for dissociated cells that are first cultured in the microwell device and/or in suspension and with an osmolality range of 270 to 320 mOsm/kg for dissociated cells directly plated onto coated culture dishes according to the methods described herein. Accordingly, in one embodiment, the osmolality of the culture medium is 260 to 280 mOsm/kg for inducing ectodermal progenitor cells. In another embodiment, the osmolality of the culture media used in the methods described herein is 270 to 320 mOsm/kg for inducing ectodermal progenitor cells.

Accordingly, in an embodiment, the present disclosure provides a method of generating a population of germ layer progenitor cells comprising:
(a) dissociating pluripotent stem cells into clusters or single cells;
(b) culturing the dissociated cells from a) in culture media with an osmolality of 270 to 320 mOsm/kg, optionally 260-280 mOsm/kg; and
(c) differentiating the cells of b) into germ layer progenitor cells.

In one embodiment, differentiating the cells in (c) comprises dissociating the cells of b) and plating the cells onto coated culture dishes and culturing for at least 1 day, optionally 3-6 days, in the culture media to produce germ layer progenitor cells.

In one embodiment, for generating an enriched population of ectodermal progenitor cells, culturing the dissociated cells in b) comprises culturing the dissociated cells from a) in a microwell device for about 24 hours to form aggregates and continuing the culture in the microwell device for more than 24 hours in the culture media followed by releasing the aggregates and adhering onto coated culture dishes and culturing in the culture media for at least 1 day. Aggregates are optionally cultured inside the microwell device for 2, 3, 4, 5, 6, 7, 8, 9, 10, 11, 12, 13, 14 or more days prior to releasing and adhering onto the coated culture dishes.

In another embodiment, for generating an enriched population of ectodermal progenitor cells, culturing the dissociated cells in b) comprises culturing the dissociated cells from a) in the culture media in a microwell device for about 24 hours to form aggregates, releasing the aggregates from the microwell device, followed by culturing the released aggregates in suspension in the culture media for at least 1 day, dissociating and adhering the aggregates onto coated culture dishes and culturing in the culture media for at least 1 day. Aggregates are optionally cultured in suspension for 2, 3, 4, 5, 6, 7, 8, 9, 10, 11, 12, 13, 14 or more days prior to releasing and adhering onto the coated culture dishes. In one embodiment, the pluripotent stem cells are cultured in suspension in a liquid or semi-solid medium.

In yet another embodiment, for generating an enriched population of ectodermal progenitor cells, culturing the dissociated cells in b) comprises culturing the dissociated cells from a) in suspension in the culture media for at least 1 day followed by dissociating the cells and adhering onto coated culture dishes and culturing in the culture media for at least 1 day. In this method, EBs are generated from stem cells by the scraping methods and are cultured for at least 1 day in the culture medium. Aggregates are optionally cultured in suspension for 2, 3, 4, 5, 6, 7, 8, 9, 10, 11, 12, 13, 14 or more days prior to dissociating and adhering on the coated culture dishes.

In a further embodiment, for generating an enriched population of ectodermal progenitor cells, culturing the dissociated cells in b) comprises adhering the dissociated cells from a) onto coated culture dishes or feeders and culturing for at least 1-3 days in the culture media. The cells are optionally cultured in adherent cultures for 1, 2, 3, 4, 5, 6, 7, 8, 9, 10, 11, 12, 13, 14 or more days.

In yet a further embodiment, the methods described herein further comprise identifying ectodermal or neural progenitor cells based on the presence of markers associated with neural cell fate selected from Pax6, Sox1, Sox2, A2B5, CD15, CD24, CD29, CD81, CD133, PSA-NCAM, Vimentin, Musashi1, Musashi2 and Nestin.

The present disclosure also provides a method of maintaining single neural progenitor cells in culture media with an osmolality of 260-340 mOsm/kg comprising generating ectodermal progenitor cells according to the methods described herein, dissociating the ectodermal progenitor cells from the adhered cultures; plating and culturing said progenitor cells for at least 1 day. In one embodiment, the single neural progenitor cells are maintained in the presence of bFGF. In another embodiment, the progenitor cells are plated and cultured for at least 4 days. In one embodiment, the cells are plated on coated culture dishes. In an embodiment, the coated culture dishes comprise factors which promote cell attachment, such as extracellular matrix molecules, synthetic molecules, synthetic peptides or chemical substrates. In another embodiment, the coated culture dishes comprise poly-L-ornithine/laminin. Typical concentrations of laminin are as described herein.

In one embodiment, the bFGF is at a concentration of 10-100 ng/mL. In another embodiment, the cells are propagated and maintained in culture for at least 3 passages. In one embodiment, the cells are propagated and maintained on coated culture dishes as described herein.

The present inventors found that incubation of adhered cultures with a buffer of $Ca^{2+}$ and $Mg^{2+}$ free 1×PBS buffer with a pH of 7.0 to 8.0 allowed selective release or dissociation of single neural progenitor cells. Accordingly, in another embodiment, the single neural progenitor cells are dissociated in a buffer comprising a $Ca^{2+}$ and $Mg^{2+}$ free 1×PBS or 1× Hank's Buffered Solution with a pH of 7.0 to 8.0. In one embodiment, the single cells are incubated in the buffer for 1 to 2 hours. In another embodiment, the cells are incubated in the buffer for 30-90 minutes.

In yet another embodiment, the cells are cultured in neuronal cell differentiation medium comprising DMEM-F12, N2, B27 or combinations thereof, non-essential amino acids, hormones, lipids, BDNF, GDNF, ascorbic acid, retinoic acid, TGFβ (neurons), sonic hedgehog (SHH), thyroid hormone, any member of the BMP family, EGF and PDGF (oligodendrocytes), cyclopamine or any other SHH inhibitor (astrocytes) to produce differentiated cells. The differentiated cells are optionally propagated and maintained on a coated culture dish as described herein. For differentiation, bFGF is removed. In one embodiment, the differentiated cells comprise neurons, astrocytes or oligodendrocytes, which are optionally identified based on the presence of markers selected from TUJ1, MAP2 (neurons), A2B5, GFAP, GLAST (glial cells, astrocytes and radial glial cells), FGFR1, FGFR2, FGFR3, FGFR4, O4, OLIG2, GalC, and NG2 (oligodendrocytes).

Endodermal/Mesodermal Differentiation

The present inventors have shown that an endodermal/mesodermal germ layer can be induced by culturing stem cells in a culture media with an osmolality range higher than 280 mOsm/kg, optionally 290-340 mOsm/kg for dissociated cells cultured in the microwell device and/or in cell suspension prior to plating on coated culture dishes by the methods described herein and an osmolality above 320 mOsm/kg, optionally 320 to 340 mOsm/kg, for dissociated cells plated directly onto coated culture dishes by the methods described herein.

Accordingly, in another embodiment, the osmolality of the culture media used in the methods described herein is higher than 280 mOsm/kg for inducing or enriching endodermal/mesodermal progenitor cells. In another embodiment, the osmolality of the culture medium is 290 to 340 mOsm/kg, for inducing or enriching endodermal/mesodermal progenitor cells. In yet another embodiment, the osmolality of the culture media used in the methods described herein is higher than 320 mOsm/kg for inducing or enriching endodermal/mesodermal progenitor cells. In yet a further embodiment, the osmolality of the culture medium is 320 to 340 mOsm/kg for inducing or enriching endodermal/mesodermal progenitor cells.

In one embodiment, a culture medium at an osmolality higher than 280 mOsm/kg, optionally higher than 320 mOsm/kg, provides differentiation into mesodermal fate, which can give rise to mesenchymal stem cells, chondrocytes, cardiomyocytes, hematopoietic stem cells and skeletal cells. In another embodiment, a culture medium at an osmolality higher than 280 mOsm/kg, optionally higher than 320 mOsm/kg, provides differentiation into endodermal fate, which can give rise to pancreas, intestinal cells and liver cells.

Accordingly, in an embodiment, the present disclosure provides a method of generating a population of germ layer progenitor cells comprising:
(a) dissociating pluripotent stem cells into clusters or single cells;
(b) culturing the dissociated cells from a) in culture media with an osmolality of 290 to 340 mOsm/kg, optionally 320-340 mOsm/kg; and
(c) differentiating the cells of b) into germ layer progenitor cells.

In one embodiment, differentiating the cells in (c) comprises dissociating the cells of b) and plating the cells onto coated culture dishes and culturing for at least 1 day, optionally 3-6 days, in the culture media to produce germ layer progenitor cells.

In an embodiment, b) comprises
 i) culturing the dissociated cells from a) in a microwell device for about 24 hours to form aggregates and continuing the culture in the microwell device for more than 24 hours in the culture media followed by releasing the aggregates and adhering onto coated culture dishes and culturing in the culture media for at least 1 day;
 ii) culturing the dissociated cells from a) in the culture media in a microwell device for about 24 hours to form aggregates, releasing the aggregates from the microwell device, followed by culturing the released aggregates in suspension in the culture media for at least 1 day, dissociating and adhering the aggregates onto coated culture dishes and culturing in the culture media for at least 1 day; or
 iii) culturing the dissociated cells from a) in suspension in the culture media for at least 1 day followed by dissociating the cells and adhering onto coated culture dishes and culturing in the culture media for at least 1 day.

In yet a further embodiment, the methods described herein further comprise identifying endodermal and/or mesodermal progenitor cells based on the presence of markers selected from Sox17, HNF1β, HNF3β, Gata4, Gata6, CXCR4 (CD184), AFP (endoderm) and Bry, MixL1, Snail, Bmp2, Bmp4, CD31, and CD34 (mesoderm).

The present disclosure also provides a method of maintaining single endodermal or mesodermal progenitor cells in culture media with an osmolality of 290 to 340 mOsm/kg comprising generating endodermal or mesodermal progenitor cells according to the methods described herein, dissociating single endodermal or mesodermal progenitor cells from the adhered cultures; and plating and culturing said progenitor cells. In one embodiment, the cells are plated on coated culture dishes as described herein.

In one embodiment, inductive factors are added to the culture media to obtain endoderm and mesoderm. The factors, for example, comprise members of the BMP and FGF family as well as activin A (Boyd et al., 2009; Kubo et al., 2004; Lee et al., 2009, Takei et al., 2009, Sulzbacher et al., 2009).

In one embodiment, the cells are propagated and maintained in culture for at least 3 passages. In one embodiment, the cells are propagated and maintained on coated culture dishes as described herein.

The present inventors found that incubation of adhered cultures with a buffer of $Ca^{2+}$ and $Mg^{2+}$ free 1×PBS buffer with a pH of 7.0 to 8.0 allowed release or dissociation of single ectodermal or neural progenitor cells. Accordingly, in another embodiment, the endodermal or mesodermal progenitor cells are obtained by releasing ectodermal cells from the culture by dissociating in a buffer of $Ca^{2+}$ and $Mg^{2+}$ free 1×PBS buffer with a pH of 7.0 to 8.0, thus leaving the endodermal and/or mesodermal cells adhered to the plate for culturing. The endodermal and mesodermal progenitor cells do not detach from the surface and therefore this method is removing the ectodermal progenitor cells, leaving an enriched population of endodermal and mesodermal cells, which can then be dissociated.

In yet another embodiment, the cells are cultured in mesodermal or endodermal cell differentiation medium to produce differentiated cells. Said differentiated cells are optionally propagated and maintained on coated culture dishes as described herein. Such differentiation medium includes, without limitation, fetal bovine serum (FBS), members of the BMP and FGF family, follistatin, Noggin, and activin A. In one embodiment, the differentiated cells comprise mesenchymal stem cells, chondrocytes, cardiomyocytes, hematopoietic stem cells, skeletal muscle cells (mesoderm), pancreatic cells, intestinal cells or liver cells (endoderm).

In another embodiment the differentiated cell lineages are identified using the differentiation markers, including, without limitation, Stro1, Collagen2, MyoD, Sox9, Actin, Msx2, Runx2, Dlx5 (mesenchymal stem cells); CD44, CD151, Sox9, Osteonectin, Collagen 2 (chondrocytes), MyoD (cardiomyocytes), CD34, CD31, CD133, Tie2 (hematopoietic stem cells), Actin, α-actinin, MyoD, Desmin (skeletal muscle cells), Islet1, Islet2, Pdx1, Insulin (pancreatic cells), Hnf1β, Cdx2 (intestinal cells), Albumin, ApoE (liver cells).

Endodermal Differentiation

The present inventors have developed methods of generating an enriched population of endoderm cells by culturing stem cells in media with controlled osmolality.

The present inventors have shown that an endodermal germ layer can be primed by culturing stem cells in a culture media with an osmolality range higher than 320 mOsm/kg, optionally 320-550 mOsm/kg, 350-450 mOsm/kg or about 365 mOsm/kg for dissociated cells cultured in the microwell device and/or in cell suspension prior to plating on coated culture dishes by the methods described herein and an osmolality higher than 320 mOsm/kg, optionally 320-550 mOsm/kg, 350-450 mOsm/kg or about 365 mOsm/kg, for dissociated cells plated directly onto coated culture dishes by the methods described herein.

Accordingly, in an embodiment, the present disclosure provides a method of generating a population of germ layer progenitor cells comprising:
(a) dissociating pluripotent stem cells into clusters or single cells;
(b) culturing the dissociated cells from a) in culture media with an osmolality of 320 to 550 mOsm/kg; and
(c) differentiating the cells of b) into germ layer progenitor cells.

In one embodiment, differentiating the cells in (c) comprises dissociating the cells of b) and plating the cells onto coated culture dishes and culturing in differentiation media.

In an embodiment, the osmolality of the culture media used in (b) of the methods described herein is higher than 320 mOsm/kg for generating an enriched population of endodermal progenitor cells. In another embodiment, the osmolality of the culture medium is 320 to 550 mOsm/kg, for generating an enriched population of endodermal progenitor cells. In yet another embodiment, the osmolality of the culture media used in the methods described herein is 350-450 mOsm/kg for generating an enriched population of endodermal progenitor cells. In yet a further embodiment, the osmolality of the culture medium is about 365 mOsm/kg for generating an enriched population of endodermal progenitor cells.

In an embodiment, for generating an enriched population of endodermal progenitor cells, the cells are cultured in (b) for 16-60 hours in a microwell device, in suspension or adhered to a culture plate. In another embodiment, for generating an enriched population of endodermal progenitor cells, the cells are cultured in (b) for about 24 hours in a microwell device, in suspension or adhered to a culture plate. In yet another embodiment, for generating an enriched population of endodermal progenitor cells, the cells are cultured in (b) for about 48 hours in a microwell device, in suspension or adhered to a culture plate.

In one embodiment, for generating an enriched population of endodermal progenitor cells, culturing the dissociated cells in b) comprises culturing the dissociated cells from a) in a microwell device for at least 16 hours to form aggregates and continuing the culture in the microwell device for up to 60 hours in the culture media prior to differentiating the cells in (c).

In another embodiment, for generating an enriched population of endodermal progenitor cells, culturing the dissociated cells in b) comprises culturing the dissociated cells from a) in the culture media in a microwell device for at least 16 hours to form aggregates, releasing the aggregates from the microwell device, followed by culturing the released aggregates in suspension in the culture media for up to 60 hours prior to differentiating the cells in (c). In one embodiment, the pluripotent stem cells are cultured in suspension in a liquid or semi-solid medium.

In yet another embodiment, for generating an enriched population of endodermal progenitor cells, culturing the dissociated cells in b) comprises culturing the dissociated cells from a) in suspension in the culture media for at least 16 hours followed by dissociating the cells and adhering onto coated culture dishes and culturing the media for up to 60 hours prior to differentiating the cells in (c).

In yet another embodiment, for generating an enriched population of endodermal progenitor cells, culturing the dissociated cells in b) comprises adhering the dissociated cells from a) onto coated culture dishes or feeders and culturing for 16-60 in the culture media, prior to differentiating the cells in (c).

In one embodiment, the pluripotent stem cells are maintained in a pluripotency medium with an osmolality below 320 mOsm/Kg prior to (a). In one embodiment, this pluripotency medium is TeSR™-E8™, Essential 8™, or Hesc-GRO™ (Millipore Cat #SCM020, 2007).

In another embodiment, the pluripotent stem cells are maintained in a pluripotency medium with an osmolality above 320 mOsm/Kg. In one embodiment, this pluripotency medium is from the list of mTeSR™ 1, TeSR™ 2, ReproFF™, ReproFF2™, DMEM+KOSR, or feeder-conditioned medium.

In one embodiment, the culture medium for step (b) is supplemented with protein(s). In one embodiment, that protein is albumin. In another embodiment, that albumin is derived from human.

Methods to differentiate pluripotent stem cells to definitive endoderm are known to those in the field and typically involve exposing pluripotent stem cells to growth factors from the TGF-beta superfamily (eg. D'Amour et al., NBT, 2005, 2006) or small molecules that activate similar intracellular signaling pathways (eg. Borowiak et al., 2009).

Definitive endoderm is defined as a cell expressing one or more markers of the definitive endoderm lineage. These markers can include CXCR4, SOX17, GATA-4, FOXA2, AFP, CER1, C-KIT, EPCAM, SNAI1, GSC, E-Cad, or N-Cad. Definitive endoderm is defined functionally by cells that are capable of further differentiating towards one or more of the tissues that are derived from the endoderm germ layer. This can include the lungs, thyroid, liver, pancreas, or intestines. The term definitive endoderm is used interchangeably with the term endoderm herein.

In one embodiment, the definitive endoderm derived from the pluripotent stem cells can give rise to cells of pancreatic, hepatic, respiratory, or intestinal lineage.

In one embodiment, the definitive endoderm cells derived from the pluripotent stem cells express, without limitation, one or more of CXCR4, SOX17, GATA-4, FOXA2, AFP, CER1, C-KIT, EPCAM, SNAI1, GSC, E-Cad, or N-Cad.

In an embodiment, for endoderm differentiation, the pluripotent stem cells have been maintained at an osmolality of 260-310 mOsm/kg prior to (a). In such embodiments (b) comprises culturing the cells in a media of higher osmolality, such as 330-550 mOsm/kg and (c) optionally then comprises culturing the cells of (b) in media of lower osmolality, such as 260-360 mOsm/kg, optionally 260-280 mOsm/kg.

Accordingly, in another embodiment, the media used for differentiating the cells in (c) has an osmolality of 260-360 mOsm/kg. In another embodiment, the media used for differentiating the cells in (c) has an osmolality of 260-280 mOsm/kg.

In an embodiment, the culture medium used in (c) to differentiate the human pluripotent stem cells to definitive endoderm is STEMdiff™ Definitive Endoderm (STEMCELL Technologies, Inc. Cat #05110) whereby the protocol is followed according to manufacturer's instructions.

In another embodiment, the culture medium used in (c) to differentiate the human pluripotent stem cells to definitive endoderm comprises a basal medium, a TGF-beta superfamily member, an FGF superfamily member, and a Wnt activator (Eg. Rezania et al., 2011).

In yet another embodiment, the culture medium used in (c) to differentiate the human pluripotent stem cells to definitive endoderm comprises a basal medium and a TGF-beta superfamily member (Eg. D'Amour et al., 2005).

In another embodiment, the culture medium used in (c) to differentiate the human pluripotent stem cells to definitive endoderm comprises a basal medium and a molecule that promotes SMAD phosphorylation.

In yet another embodiment, the endodermal progenitor cells are further differentiated to form pancreatic cells, respiratory cells, intestinal cells or liver cells.

In an embodiment, the definitive endoderm markers are expressed in greater than 50% of the cells. In another embodiment, the definitive endoderm markers are expressed in greater than 75% of the cells. In yet another embodiment, the definitive endoderm markers are expressed in greater than 80% of the cells.

Assays of the Disclosure

The cells generated by the methods described herein will allow experimental dissection of the events during early development of the nervous system, and the identification of new genes and polypeptide factors which may have a therapeutic potential such as for induction of regenerative processes. Additional pharmaceutical applications may include the development of toxicity assays and drug discovery platforms, such as high-throughput screens for neuroprotective compounds. Generation of neural progenitors from hES cells in vitro may serve as an unlimited source of cells for potential cell therapies for neurodegenerative diseases and for the delivery and expression of factors in the nervous system.

The neural progenitor cells and differentiated neural cells that are generated by the methods described herein may be used for the study of the cellular and molecular biology of human neural development, for the discovery of genes, growth factors, and differentiation factors that play a role in neural differentiation and regeneration, for drug discovery and for the development of screening assays for teratogenic, toxic and neuroprotective effects.

Accordingly, the present disclosure provides a method of screening germ layer cells comprising (a) preparing a culture of ectodermal, endodermal and/or mesodermal germ layer cells by the methods described herein;

(b) treating the germ layer cells with a test agent or agents; and (c) subjecting the treated germ layer cells to analysis.

In another embodiment, there is provided a method of screening neural progenitor cells comprising (a) preparing a culture of neural progenitor cells by the methods described herein;

(b) treating the neural progenitor cells with a test agent or agents; and (c) subjecting the treated neural progenitor cells to analysis.

In one embodiment, the test agent is a chemical or other substance being tested for its effect on differentiation of the germ layer cells or neural progenitor cells into specific cell types. In such an embodiment, the analysis may comprise detecting markers of differentiated cell types. For neural differentiation from ectodermal or neural progenitor cells, markers include, without limitation, Nestin, Sox1, and TUJ1. For endodermal differentiation from endodermal cells, the markers include, without limitation, Sox7, Sox17, HNF1β, HNF3β, Gata4, Gata6, CXCR4 (CD184), alpha-fetoprotein (AFP) (endoderm). For mesodermal differentiation from mesodermal cells the markers include, without limitation Bry, MixL1, Snail, Bmp2, Bmp4, CD31, CD34, (mesoderm). In an embodiment, the screening assay is used to identify compounds that may have therapeutic potential such as for induction of regenerative processes or providing neuroprotective compounds.

In another embodiment, the test agent is a chemical or drug and the screening is used as a primary screen or as a secondary pharmacology and toxicology evaluation screen for the chemical or drug.

Culture Media of the Disclosure

The present disclosure also provides culture media compositions useful for inducing germ layer progenitor cells. In one embodiment, the culture media comprises an osmolality lower than 550, optionally lower than 340 mOsm/kg. In another embodiment, the culture media comprises an osmolality of 240 to 550 mOsm/kg, optionally 240 to 340 mOsm/kg. In yet another embodiment, the culture media comprises an osmolality of 260 to 340 mOsm/kg. In yet another embodiment, the culture media comprises an osmolality of 330 to 450 mOsm/kg.

The present disclosure also provides culture media compositions for use in inducing ectodermal germ layer progenitor cells. In one embodiment, the culture media comprises an osmolality of 260 to 280 mOsm/kg. In another embodiment, the culture media comprises an osmolality of 270 to 320 mOsm/kg. The present disclosure further provides culture media for use in inducing mesodermal and/or endodermal germ layer progenitor cells. In one embodiment, the culture media comprises an osmolality above 280 mOsm/kg, optionally, 290 to 340 mOsm/kg. In another embodiment, the culture media comprises an osmolality above 320 mOsm/kg, optionally, above 330 mOsm/kg, such as from 350 mOsm/kg to 450 mOsm/kg.

The culture media for ectoderm induction in (b) can be any culture media useful in maintaining or differentiating stem cells. For example, the culture media is optionally pluripotent factor free or factor free media comprising the components shown in Table 2 and adjusted for the desired osmolality, optionally 260-340, 260-280, 290-340 or about 270 mOsm/kg.

Alternatively, for priming pluripotent stem cells for endoderm induction in (b), the culture medium is optionally pluripotency media comprising the components shown in Table 4 and adjusted for desired osmolality, optionally 320-550, 350-450, or about 365 mOsm/Kg.

A person skilled in the art would readily understand how to adjust the osmolality of the solution, for example, the osmolality can be adjusted by adding salt as described in Example 5. Briefly, the amount of salt to be added to a 5× supplement is calculated using the following formula: For example to obtain an osmolality of 270 after mixing a 5× supplement (initial osmolality of 100 mOsm/kg) and a basal medium (here: initial osmolality of 300 mOsm/kg):

$$[270-((0.8\times300 \text{ mOsm})+(0.2\times100 \text{ mOsm}))]/2000\times 58.44\times1.05=0.30 \text{ g/L of NaCl}$$

The osmolality of 270 mOsm/Kg can be achieved by any other media preparation methods and starting medium formulation by adjusting the concentration of NaCl.

Kits of the Disclosure

The present disclosure also provides a kit comprising a medium with an osmolality of between 260 and 310 mOsm/Kg and a concentrated supplement. In an embodiment, the concentrated supplement comprises a physiological diluent and a salt, such as sodium chloride. In another embodiment, the concentrated supplement further comprises a protein. In one embodiment, the protein is albumin, optionally derived from an animal source or a recombinant source, such as human recombinant albumin.

Stem cell culture media are known in the art for maintaining stem cells. In one embodiment, the culture media is serum-free. In another embodiment, the culture media comprises a mixture of DMEM and F-12 and optionally further comprises vitamins, salts, trace elements, selenium, insulin, lipids, proteins, amino acids, TGF-beta, FGF2, or mixtures thereof. Examples of typical culture media include mTeSR™ 1, TeSR™ 2, TeSR™-E8™, Essential 8™, Knockout™ D-MEM with KOSR, ReproFF™, and ReproFF2™ (ReproCell Cat #RCHEMD004, RCHEMD006, 2012). Combinations of these media formulations can be used for mesoderm, ectoderm, and endoderm induction.

In one embodiment, the kit comprises a pluripotent stem cell maintenance medium. In another embodiment, the medium is TeSR™-E8™, Essential 8™, or E8. In yet another embodiment, media comprises the components shown in Table 4.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1. Culture of Human Pluripotent Stem Cells as Aggregates in Defined Serum-Free Medium on BD Matrigel™ Coating Human pluripotent cells were maintained on BD Matrigel™ coated dishes in defined serum-free medium. A detailed protocol can be found in manual #29106 "Maintenance of Human Embryonic Stem Cells in mTeSR™ 1" by STEMCELL TECHNOLOGIES INC. for the maintenance of human pluripotent stem cells which includes the procedure for BD Matrigel™ coating. Cells were passaged when the colonies were large, beginning to merge, and had centers that are dense and phase-bright compared to their edges (see FIG. 1). Depending on the size and density of seeded aggregates, cultures were passaged 5-7 days after initial seeding.

Medium was aspirated from the stem cell culture and cells were rinsed with DMEM/F-12 (2 mL/well). 1 mL of dispase (STEMCELL TECHNOLOGIES INC. catalogue #07923) was added per well at a concentration of 1 mg/mL. The dish was placed at 37° C. for 7 minutes.

Once the colony edges appeared slightly folded back, dispase was removed, and each well was gently rinsed 2-3 times with 2 mL of DMEM/F-12 per well to dilute away any remaining dispase. 2 mL/well of DMEM/F-12 or mTeSR™ 1 was added to the well and colonies were scraped off with a cell scraper (e.g. Corning Catalog #3010) or a serological pipette tip.

The detached cell aggregates were transferred to a 15 mL conical tube and the well was rinsed with an additional 2 mL of DMEM/F-12 to collect any remaining aggregates. The rinsed media containing remaining cells was added to the same 15 mL tube.

The 15 mL tube containing the aggregates was centrifuged at 300×g for 5 minutes at room temperature (15-25° C.). The supernatant was aspirated. For each well of hESC aggregates collected in the 15 mL tube, 1-2 mL of mTeS®1 were added. The pellet was resuspended gently by pipetting up and down using a P1000 micropipette (1-2 times). Cells were maintained as aggregates. Using the "clump count" method the number of clumps was estimated. To enumerate clumps that are likely to attach and grow of the right size (~50-60 μm in diameter), a micrometer placed in the microscope eyepiece is used. To perform the clump count, 30 μL of DMEM/F-12 were aliquoted into 2 wells of a 96-well flat-bottom plate. A "+" was drawn centered on the bottom of these wells to serve as a counting grid. 5 μL of a freshly mixed clump suspension was added to each well. Clumps were counted in duplicate that were approximately 3500 μm² or greater. This corresponds to clumps with a diameter of approximately 60 μm. The total number of clumps per μl was estimated using the formula:

Total # of clumps per μl=$x$ clumps counted/5 μL
total volume of suspension

A defined number of clumps according to the size of the well or dish that is being seeded was plated. The volume of clump suspension (y) used to seed new dishes was calculated using the guide in Table 1 for appropriate seeding densities. For example (y) for a 6-well equals: 350/# clumps counted per μl.

hESC aggregates were plated with 2 mL of mTeSR™ 1 per new 6-well coated with BD Matrigel™. The plate was moved in several quick, short, back-and-forth and side-to-side motions to disperse cells evenly across the surface of the wells. The plate was placed in a 37° C. incubator. hESCs cultured in mTeSR™ 1 and BD Matrigel™ can be used as a consistent source of cells for the differentiation protocols in this disclosure. FIG. 1 shows undifferentiated H9 hESCs at passage 51 on day 5 of culture.

Figure 2:
FIG. 2 shows human embryonic stem cells cultured on mouse fibroblast cells (MEFs) on day 4 of culture. Magnification: 2×.

Example 2. Preparation of Mouse Embryonic Fibroblast Layers (MEFs) for Maintenance Cultures of hES Cells Irradiated embryonic day 13 mouse embryonic fibroblasts (MEF's) (CF-1 mouse strain) were prepared according to standard protocols (WiCell Research Institute web page: https://www.wicell.org and Dravid et al., Human Embryonic Stem Cell Protocols, Humana press). The day prior to plating human pluripotent stem cells onto the MEFs, a vial of irradiated MEFs was thawed into standard "MEF-medium" according to the WiCell Research Institute's standard protocols. Approximately 2×10⁴ cells/cm², which corresponds to approximately 2×10⁵ cells per 6-well, were plated. FIG. 2 shows hESCs cultured on MEFs at day 4.

Example 3. Culture of Human Pluripotent Stem Cells on Mouse Feeder Cells

Human pluripotent stem cells maintained on mouse feeder cells can also be used as a consistent source of cells for the differentiation protocols in this disclosure.

H9 hESCs were grown on MEF's (see Example 2) in hESC medium (DMEM-F12 (STEMCELL TECHNOLOGIES INC., catalog #36254), 25% knock-out serum replacer (Invitrogen, catalog #10828028), 200 mM L-glutamine (Invitrogen, catalog #25030081), 0.1 mM β-mercaptoethanol (Sigma, catalog #63689), 1×NEAA solution (Invitrogen, catalog #11140050), 4 ng/ml bFGF (STEMCELL TECHNOLOGIES INC., catalog #02634) according to the WiCell Research Institute's standard protocols which can be found on the WiCell Research Institute web page (https://www-.wicell.org) and Dravid et al., Human Embryonic Stem Cell Protocols, Humana press).

Briefly, cells were split when the feeder layer was more than 2 weeks old; colonies started to merge or became large with dense centers. For passaging of human pluripotent stem cells, a 1 mg/ml collagenase type IV (STEMCELL TECHNOLOGIES INC., catalog #07909) solution in DMEM/-F12 was used per 6-well. The culture medium was aspirated and collagenase solution was added for 5 minutes at 37° C. Using a 5-ml serological pipette, cells were scraped off the plate, while slowly pipetting the collagenase solution up and down to wash the cells of the surface. The suspension was transferred into 15-ml conical tube (Falcon) and was centrifuged at 300 g for 5 minutes. The supernatant was aspirated and 2-3 ml of hESC medium was added. By gently tapping the tube, the pellet was reconstituted and centrifuged again at 300×g for 5 minutes. In the meantime, media was aspirated from the MEF's and cells were washed 2× with 1×PBS (Ca, Mg free), pH 7.4. Supernatant was removed from the pelleted hESCs and 12 ml of fresh hESC medium were added. Using a 10-ml serological pipette, the pellet was carefully resuspended and the cell suspension was distributed onto the 6-well plate of MEFs (this equals a 1:6 split ratio of the hESCs). The plate was moved back-and-forth and side-to-side several times to distribute the cells evenly. The plate was then returned to the incubator.

Example 4. Morphological Assessment of Pluripotency of Human Pluripotent Stem Cells (hPSCs) Grown in mTeSR™ 1 on BD Matrigel™

Figure 3:
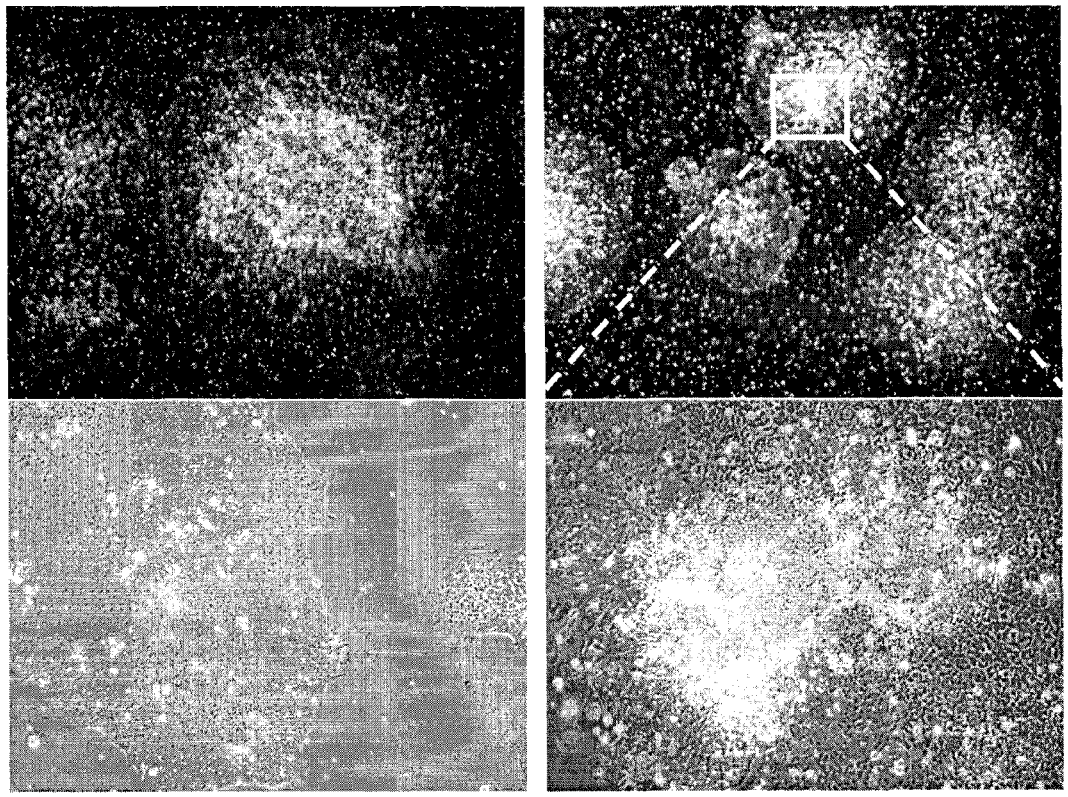
FIG. 3 shows the morphology of undifferentiated pluripotent human ESCs (left side) and of a culture showing signs of differentiation (right side). Top: magnification 2×, bottom: 10×.

For the successful induction of germ layers, a highly pure population of pluripotent stem cells was used. The following criteria were employed to assess the morphology and quality of cells (described in technical manual #29106 by STEMCELL TECHNOLOGIES INC.): Undifferentiated human pluripotent stem cells, grew as compact, multi-cellular colonies, as shown in FIG. 1. They exhibited a high nuclear-to-cytoplasm ratio and prominent nucleoli. These colonies were characterized by a distinct border. Healthy hPSCs colonies were multilayered in the center, resulting in clusters of phase-bright cells when viewed under phase contrast. Differentiation was characterized by loss of border integrity, gross non-uniform cell morphology within the colony and the emergence of obvious alternate cell types. The percentage of pluripotency was estimated by observation of the colonies under the microscope (using 4× and 10× objectives). Cells were used for germ layer induction only when they displayed less than 1% of differentiation. FIG. 3 shows pluripotent stem cells in the left column and an example of a colony with a differentiating center (red box and close-up) in the right column.

Example 5. Media Formulations with Different Osmolality Ranges: Factor Free mTeSR™ 1 Medium with Modified Osmolalities The complete media formulation and method of preparation for modified TeSR (mTeSR™ 1, STEMCELL TECHNOLOGIES INC., catalogue #05850) is published in Ludwig et al, Nature Methods 3(8): 637, 2006. It is based on the original TeSR formulation published in Ludwig et al., Nature Biotechnology 24(2): 185, 2006, with the following modification: substitution of human serum albumin (HSA) with bovine serum albumin (BSA).

To manufacture the factor free mTeSR™ 1 (mTeSR™ 1-F) media, a 5× supplement was produced containing all of the mTeSR™ 1 reagents at 5-fold concentrations, with the exceptions of the following 5 factors: GABA, pipecolic acid, bFGF, TGFβ1, lithium chloride. The components for the media are shown in Table 2.

After mixing the components of the 5× supplement together, the pH was adjusted to 7.4 by adding 10N NaOH. The osmolality of the solution was measured using a standard osmometer. The initial osmolality of the 5× supplement was usually around 100 mOsm/kg, and salt (NaCl) was used to increase the osmolality while taking into account that the 5× supplement is combined with 400 mL of the base medium DMEM/F12 (Hyclone, catalog #SH30004) (with an osmolality of around 300 mOsm/kg) to obtain mTeSR™ 1-F. The amount of salt that had to be added to the 5× supplement was calculated using the following formula: For example to obtain an osmolality of 270 after mixing the 5× supplement and the basal medium:

[270−((0.8×300 mOsm)+(0.2×100 mOsm))]/2000× 58.44×1.05=0.30 g/L of NaCl

The x amount of NaCl was added to the 5× supplement. Four media with different osmolalities were prepared: 260 mOsm/kg, 280 mOsm/kg, 320 mOsm/kg and 340 mOsm/kg.

Example 6. Generating a Single Cell Suspension of Human Pluripotent Cells for EB Formation in AggreWell™ 400

The procedure to generate single cells from human pluripotent stem cell colonies and use them in the AggreWell™ 400 protocol and device is described in technical manual 29146 (STEMCELL TECHNOLOGIES INC.). Briefly, 10-cm plates containing undifferentiated H1 passage 46 hESCs at semi-confluence were removed from the incubator and placed inside a sterile tissue culture hood. mTeSR™ 1 maintenance medium was aspirated from the H9 cultures, and each plate was then rinsed with 2 mL of 1×PBS (Ca, Mg free), pH 7.4 was then aspirated and discarded. Accutase (STEMCELL TECHNOLOGIES INC. catalogue #07920) was used to dissociate the adherent hESC culture into single cells. 3 mLs of Accutase were added directly to each 10-cm plate containing undifferentiated H9 cell cultures. Plates were then incubated at 37° C. for approximately 10 minutes, or until cells detached easily from the plate with gentle shaking. The H1 cell suspension was gently pipetted 2-3 times with a serological pipette to ensure any remaining clumps were fully dissociated and to dislodge any cells that were still attached to the surface of the dish. The suspension was transferred to a 50 mL conical tube. Each plate was rinsed with 10 mL of 1×PBS (Ca, Mg free), pH 7.4 and the rinsing solution was transferred to the same 50 mL tube containing the cell suspension.

H9 hESCs grown on MEFs (see Example 3) were dissociated into a single cell suspension using the same procedure. Most feeder cells within the EBs died during EB formation and are believed to not disturb the germ layer induction process within the EBs.

Cell suspensions were centrifuged at 350×g for 7 minutes at room temperature (15-25° C.). The supernatant was aspirated and discarded. Cell pellets were resuspended in a 1 mL volume of the medium mTeSR™ 1-F of osmolality 270, 290, 320 or 340 mOsm/kg. Y27632 rock inhibitor (STEMCELL TECHNOLOGIES INC. catalogue #07171/2) was also added to the medium at a final concentration of 10 µg/mL to enhance cell survival during EB formation (Watanabe et al, 2007). Viable cells were counted using standard techniques, by diluting a 10 µL sample of the cell suspension 1:10 in 90 µL of trypan blue (Invitrogen, catalog #15250061) and counting unstained cells on a haemocytometer. The number of cells per µl allows calculating the volume of cells to use for EB formation (Example 7). One 10-cm dish of hESCs gave rise to 7-10×10$^6$ cells.

Figure 4:
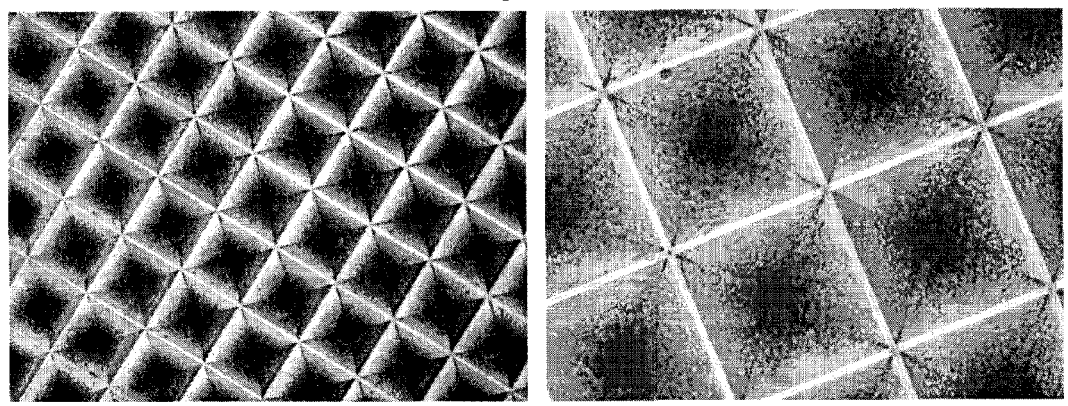
FIG. 4 shows EB formation in AggreWell: single cell suspensions are distributed in a single well of an AggreWell™ 400 plate. Each microwell holds 2000 cells. Magnification: 2× (left) and 10× (right).

Example 7. EB Formation from Human Pluripotent Stem Cells Using a Microwell Device (AggreWell™ 400) in mTeSR™ 1-F 270, 290, 320 and 340 mOsm/kg Media to Induce the 3 Germ Layers Controlled sized EBs can be generated very efficiently using AggreWell™ 400. Briefly, undifferentiated H1 hESCs were cultured to semi-confluency, using the method of Example 1. As described in technical manual #29146 (STEMCELL TECHNOLOGIES INC.), an AggreWell™ 400 plate was removed from the packaging in a sterile tissue culture hood. Each of the 8 microwell-containing wells of the plate was rinsed with 1 mL of 1×PBS ($Ca^{2+}$, $Mg^{2+}$ free), pH 7.4, and the PBS was then removed by aspiration. 1 mL of medium was added to each well of the AggreWell™ 400 plate. To induce the three different germ layer cell types: ectoderm, endoderm and mesoderm, media with 4 different osmolalities were used for EB formation: 270 mOsm/kg, 290 mOsm/kg, 320 mOsm/kg and 340 mOsm/kg (preparation: see Example 4). Y27632 rock inhibitor was also added to the medium at a final concentration of 10 μg/mL to enhance cell survival during EB formation. The AggreWell™ 400 plate was centrifuged at 3000×g for 2 minutes in a swinging bucket rotor fitted with a plate holder to remove any small bubbles from the microwells. AggreWell™ 400 plates were then set aside while preparing a single cell suspension of H1 hESCs cells using the method of Example 6. A volume of the cell suspension containing $2.4 \times 10^6$ cells was added to each well of the AggreWell™ 400 plate prepared previously. This amount of cells will distribute into the approximately 1200 microwells to form EBs of approximately 2,000 cells each. Medium was added as above, to a final volume of 2 mL per well. The AggreWell™ 400 plate was centrifuged at 100×g for 3 minutes to capture the cells in the microwells. Plates were incubated at 37° C. with 5% $CO_2$ and 95% humidity for 24 hours. FIG. 4 shows the distributed single H1 hESCs cells within the microwells of an AggreWell™ 400 well.

Figure 5:
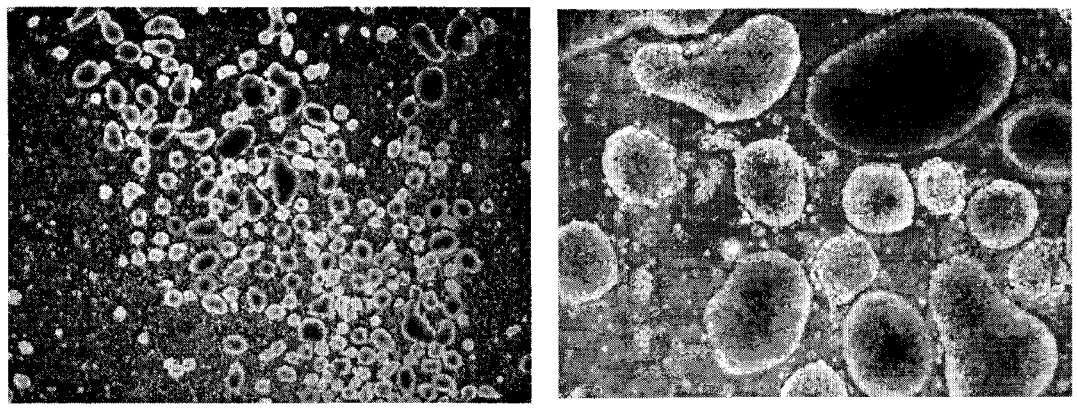
FIG. 5 shows scraped EBs after 1 day of suspension culture. Magnification: 2× (left) and 10× (right).

Example 8. EB Formation by the "Scraped EB" Method and Culture in Suspension Cultures to Induce Differentiation into the Three Germ Layers EBs can also be routinely generated by the scraping method which does not allow control for size and shape of EB. To form EBs, adherent human pluripotent stem cell colonies were lifted from the tissue culture plate using mechanical scraping. The resulting randomly sized clumps of cells were placed into non-adherent suspension culture and EBs were incubated in a standard tissue culture incubator, at 37° C., 5% $CO_2$ and 95% humidity for a period of 5 days, with a media change every 2 days. For this purpose, the dish was tilted towards one side and using a 1000-μl pipette tip, approximately half the volume of the medium was removed without disturbing the EBs. For induction of the 3 germ layers the same media were used as described in Example 7. Fresh medium was added up to 5 ml. EBs were further processed for ectoderm, mesoderm and endoderm induction as described in Example 9 and 11-13. FIG. 5 shows scraped EBs 1 day after formation in mTeSR™ 1-F 270 mOsm/kg.

Example 9. Five Day Suspension Culture of EBs in mTeSR™ 1-F 260, 270 and 280 mOsm/kg to Induce Neuroectodermal Cell Lineages EBs were formed from H9 hESCs cells as described in Example 7. Briefly, a single cell suspension containing $2.4 \times 10^6$ human ES cells was added to a well of AggreWell™ 400, to generate approximately 1200 EBs of 2,000 cells each.

Figure 6:
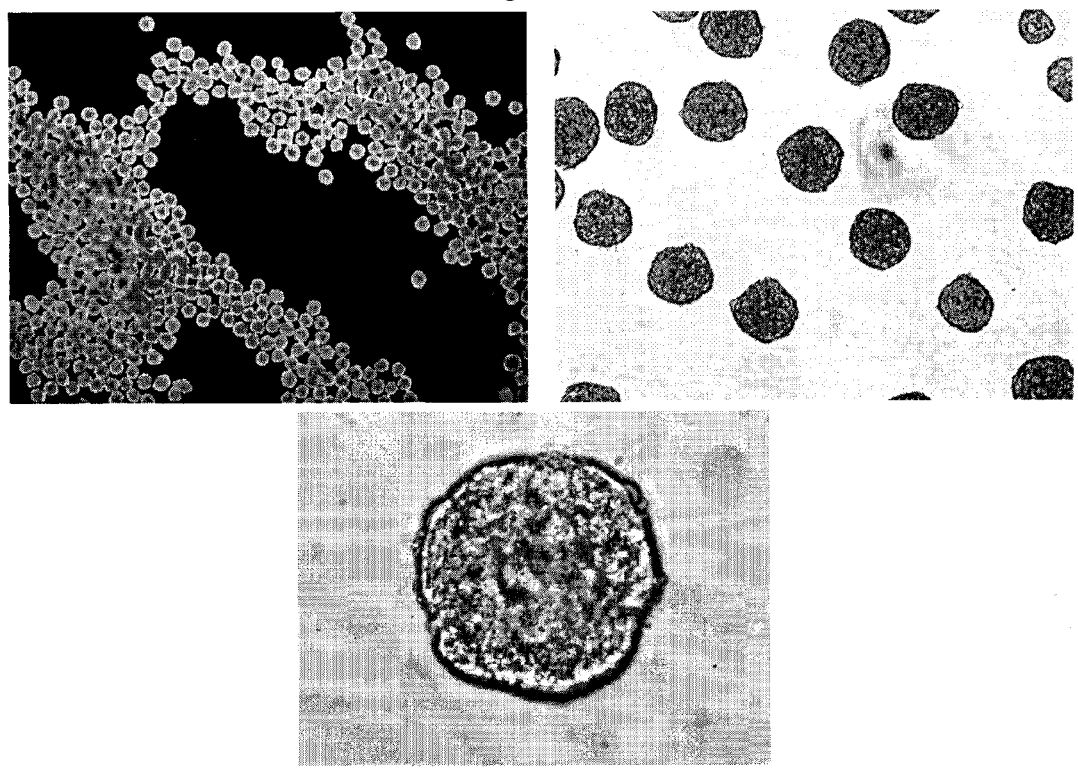
FIG. 6 shows EBs after 24 h incubation in AggreWell™ 400 plate. EBs formed via forced aggregation in the AggreWell™ 400 plate were applied onto cell strainer to remove single cells. 2×, 10× and 40× magnification.

EBs were then harvested in a sterile tissue culture hood, by gently pipetting up and down the medium in the AggreWell™ 400 microwells 2-3 times with 1 mL disposable pipette tip to dislodge most of the EBs. To harvest the EBs, the suspension was passed through an inverted 40 μm nylon cell strainer (Falcon) sitting on top of a 50 mL conical tube to remove unaggregated single cells and debris. AggreWell™ 400 surface was washed a further 5 times with 1 mL each of DMEM/F-12, pipetting across the entire surface to dislodge all aggregates. All washes were applied onto the cell strainer membrane. The cell strainer was turned upside down, holding it close over a low-adherence 6-well. EBs were washed of the membrane using mTeSR™ 1-F 260, 270 or 280 mOsm/kg medium to induce differentiation of the formed EBs into neuroectoderm. Approximately 5 ml of medium were used to remove the EBs from the nylon membrane holding the strainer over a single well of a 6-well ultra-low adherence dish (STEMCELL TECHNOLOGIES INC., catalog #27145). EBs were incubated in a standard tissue culture incubator, at 37° C., 5% $CO_2$ and 95% humidity for a period of 5 days, with a media change every 2 days. For this purpose, the dish was tilted towards one side and using a 1000-μl pipette tip, approximately half the volume of the medium was removed without disturbing the EBs. Fresh medium was added up to 5 ml. FIG. 6 shows the released EBs after 24 hours of incubation in the AggreWell™ 400 plate at 2×, 10× and 40× magnification. There were no morphological differences observed at the time of recovery of EBs from the AggreWell™ 400 plates.

Example 10. Induction of in Vitro Differentiation of Human Pluripotent Stem Cells into Neural Progenitors in Adherent Monolayer Culture Containing Media in an Osmolality Range of 270 to 320 mOsm/kg For this purpose human pluripotent stem cells were used either as clusters or as single cell layers plated on BD Matrigel™ or onto human or mouse feeder cells. To plate cells as clusters 1×PBS (Ca, Mg free), pH 7.4 was used to dissociate stem cell colonies. Alternatively, any enzymatic, chemical or mechanical method that generated clusters of hESC can be used, such as but not limited to collagenase, dispase or mechanical scraping. Cells were rinsed with 1×PBS (Ca, Mg free), pH 7.4 after removal of culture media. The PBS was left on the cells for approximately 10 minutes at room temperature. Cells were gently pipetted up and down using a 5-mL serological pipette and transferred into a 15 mL conical tube. Clumps were centrifuged at room temperature at 350×g for 5 minutes. The 1×PBS (Ca, Mg free), pH 7.4 was removed and cells were resuspended in 1 mL of either mTeSR™ 1-F 270 or 320 mOsm/kg, briefly shooting them off the bottom of the tube using a 1000 μl pipette tip. Optionally, N2A (STEMCELL TECHNOLOGIES INC., catalog #07152) and B27 (STEMCELL TECHNOLOGIES INC., catalog #07153) at a 1× concentration were added to the induction media. The cell clump suspension was distributed between 5 wells of a 6-well plate coated with BD Matrigel™.

To obtain single cell suspensions to use for adherent induction, the method of Example 6 was used. Cells were plated at densities of approximately $2 \times 10^5$ cells per 6-well into mTeSR™ 1-F 270 or 320 mOsm/kg. Medium was changed every 2 days.

Figure 7:
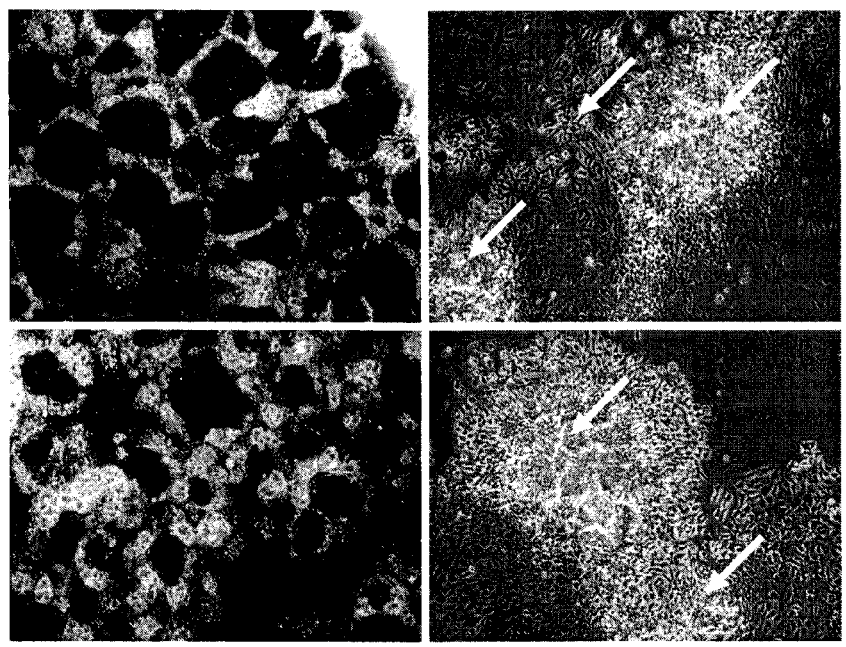
FIG. 7 shows neural rosettes induced from human embryonic stem cells at day 5 in adherent culture conditions. Media used were mTeSR™ 1-F 270 mOsm/kg+1×B27/N2A (upper row) and mTeSR™ 1-F 320 mOsm/kg+1×B27/N2A (lower row). Arrows point towards rosette structures. Left column: magnification 2×, right column: magnification 10×.

FIG. 7 shows neural progenitor cells emerging from the seeded clumps after 5 days of induction. During neural differentiation human pluripotent stem cells undergo morphogenetic events characterized by the formation of radially organized columnar epithelial cells termed "neural rosettes" (Zhang et al. 2001; Perrier et al. 2004). These structures comprise cells that are capable of differentiating into various region-specific neuronal and glial cell types in response to appropriate developmental cues (Perrier et al. 2004; Li et al. 2005). Rosettes appear in different sizes and shapes and can be easily identified. In both media (mTeSR™ 1-F 270 and 320 mOsm/kg) rosettes formed with almost the same efficiencies and were visible after 3 days. The induction period was 5-6 days. Arrows point towards some examples of rosettes.

Example 11. Plating of EBs After Suspension Cultures in mTeSR™ 1-F 260, 270 and 280 mOsm/kg to Enable Outgrowth of Neuroectodermal Progenitors After EB formation and cultivation using the methods of Examples 6 and 7, the EBs were visualized under the microscope. There was no obvious morphological difference observed in the EBs cultivated in different osmolalities.

Figure 8:
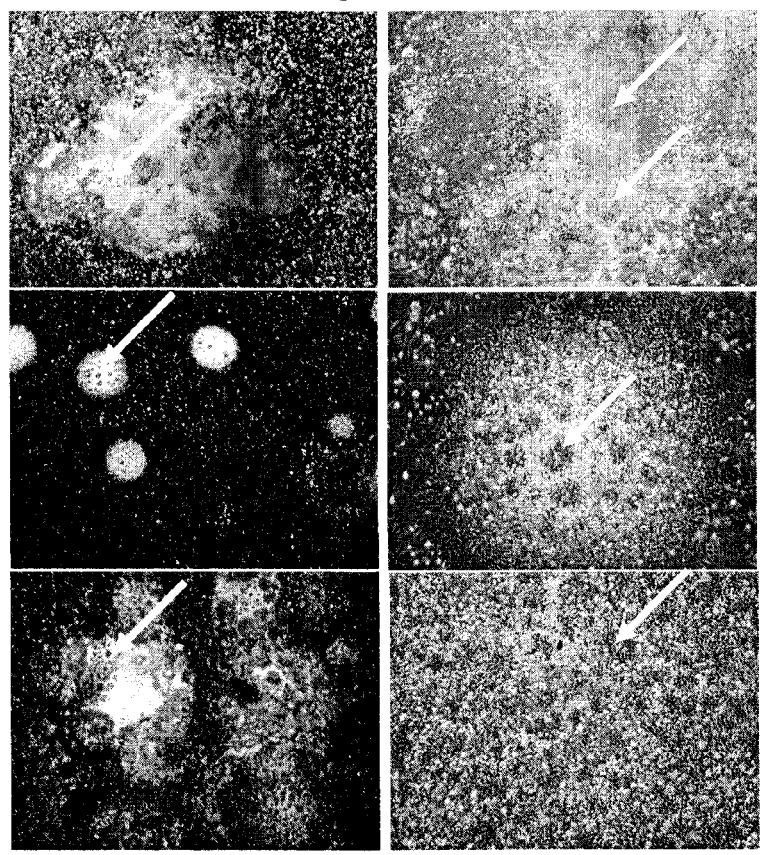
FIG. 8 shows neural rosettes induced in 3 different media in EB based conditions in AggreWell™ 400. Upper row: mTeSR™ 1-F 260 mOsm/kg; middle row: mTeSR™ 1-F 270 mOsm/kg; lower row: mTeSR™ 1-F 280 mOsm/kg. Arrows point towards rosette structures. Left column: magnification 2×, right column: magnification 10×.

To be able to cultivate individual neural progenitor cells, using optionally mechanical trituration the EBs were dissociated into small clusters. Alternatively, other chemical methods alone or in combination with enzymatic dissociation methods, or enzymatic dissociation may be used for this purpose. This procedure enabled the neural progenitor cells to grow out from these structures and form multi-layered clusters of cells and single cell layers. For mechanical trituration, EBs were transferred from 6-well plates into conical 15 mL tubes using a 1000 µl-pipette tip. EBs were left to settle to the bottom of tube, by incubating for 5 mins at room temp. Supernatant was removed, leaving pelleted EBs at the bottom of the tube. 1 ml of fresh mTeSR™ 1-F 260, 270 or 280 mOsm/kg was added to corresponding tubes. Using a 1000 µl-pipette tip, cells were dissociated by pipetting up and down 5-20 times depending on the consistency of the EBs until a cell suspension containing barely visible small clusters was generated. The cell suspension of one 15 mL tube (corresponding to EBs that were cultured in one 6-well) was distributed onto 3 wells of a 6-well dish each containing 3 glass coverslips coated with Poly-L-Ornithine/Laminin (see Example 18). Media was filled up to 2 ml and cells were distributed evenly by gently rocking the plate back and forth. The dishes were placed back into 37° C. Attachment was observed after several hours. FIG. 8 shows the attached EBs after 2 days. Arrows point towards some examples of rosettes. Rosettes are present in all 3 media and can be seen after 2 days of attachment. The percentage of rosettes and therefore the efficiency of neural induction were assessed as described in Example 12.

Figure 9:
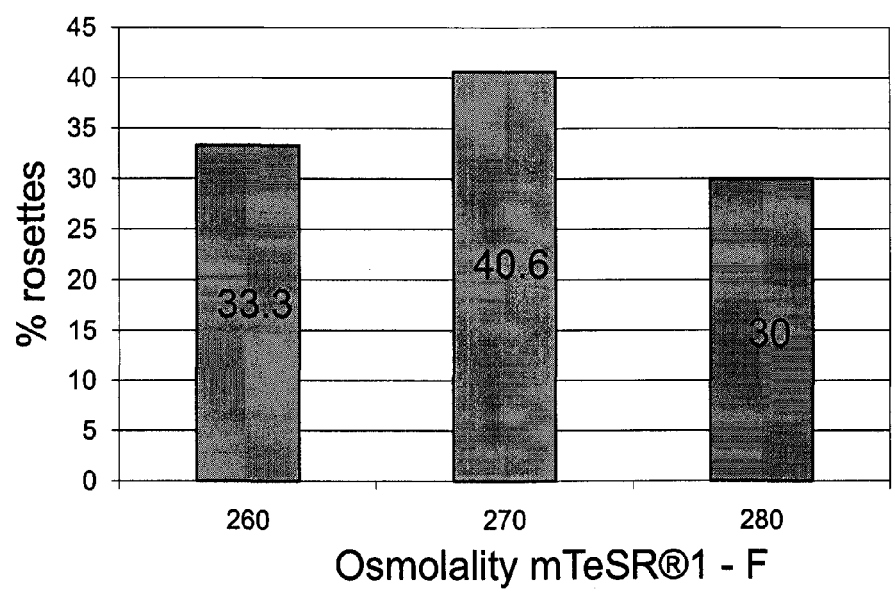
FIG. 9 shows average rosettes counts of experiments where EBs were induced and cultured in mTeSR™ 1-F 260 mOsm/kg (33.3%); mTeSR™ 1-F 270 mOsm/kg (40.6%) or mTeSR™ 1-F 280 mOsm/kg (30%).

Example 12. Morphological Assessment of Attached EBs from Suspension Culture in Media within the Osmolality Range of 260-280 mOsm/kg to Determine the Percentage of Neuroectoderm Present Two days after plating the dissociated EBs (see Example 11), rosette structures became apparent (FIG. 8). These neural rosettes represented a mixture of size-ranged rosettes, "ridge-like" rosettes with multiple cell layers and single cell layered "star-shaped" rosettes. Scoring criteria were set up to estimate the percentage of rosette containing colonies. To make the criteria stringent, only colonies with more than 50% of rosettes present were counted. Colonies with a lower percentage were not included. The following formula was used to calculate the total percentage of neural rosettes: "Total number of colonies/number of colonies with more than 50% of rosettes present". FIG. 9 summarizes the results of rosette-counts.

Figure 10:
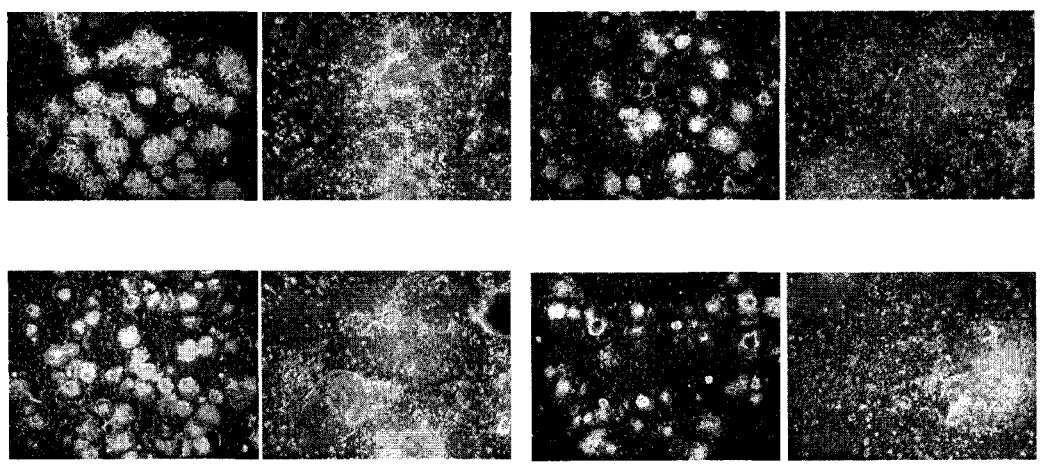
FIG. 10 shows the morphology of attached EBs after 5 days of suspension culture in mTeSR™ 1-F 270 mOsm/kg (upper row, left 2 pictures); mTeSR™ 1-F 290 mOsm/kg (upper row, right 2 pictures); mTeSR™ 1-F 320 mOsm/kg (lower row, left 2 pictures) or mTeSR™ 1-F 340 mOsm/kg (lower row, right 2 pictures). Magnifications: 2× (left pictures in each condition) and 10× (right pictures in each condition).
Figure 11:
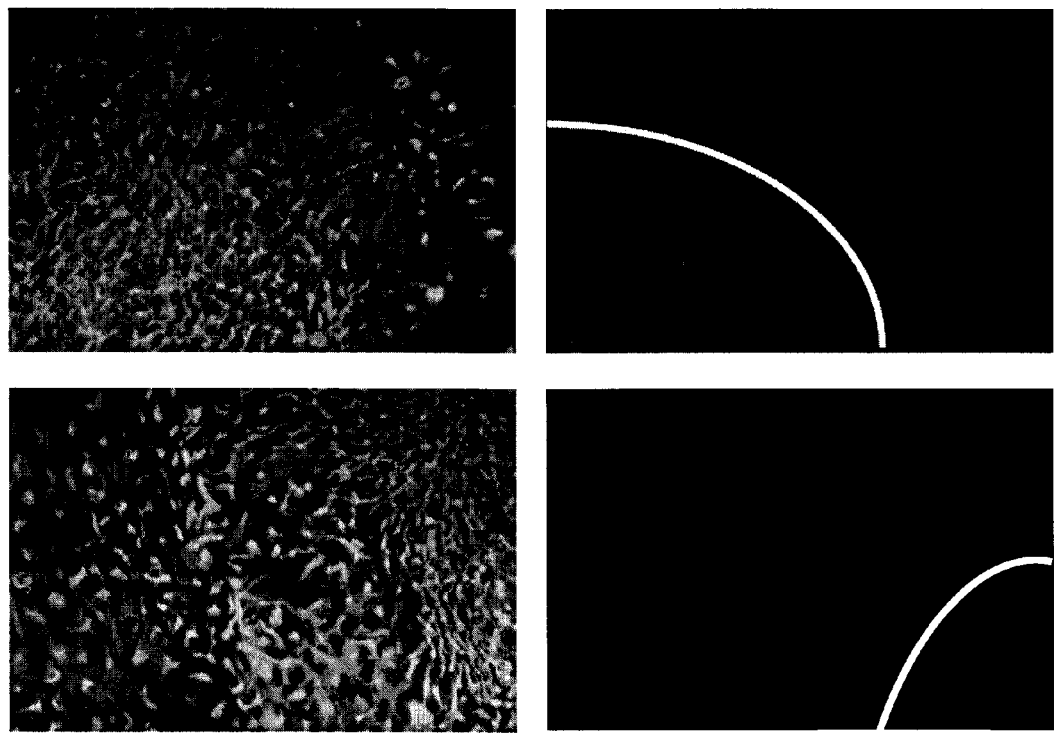
FIG. 11 shows attached EBs after 3 days. Immunocytochemical staining for Nestin (left column) and Sox1 (right column). The area of the picture where there is Sox1 expression is marked off (white line). EBs were formed either in mTeSR™ 1-F 270 mOsm/kg (upper row) or mTeSR™ 1-F 340 mOsm/kg (lower row). The area of cells expressing Sox1 is clearly larger in cells induced in mTeSR™ 1-F 270 mOsm/kg compared to cells induced in or mTeSR™ 1-F 340 mOsm/kg. Magnification 20×.
Figure 17:
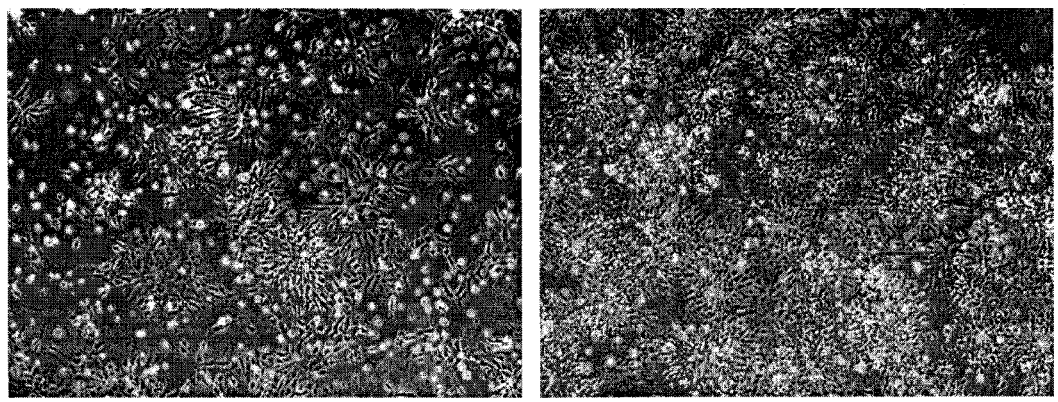
FIG. 17 shows neural progenitor cells were passaged and pictures were taken at 2 days after attachment (left) or 5 days after attachment (right). Magnification 10×.

Example 13. Five Day Suspension Culture and Plating of EBs in mTeSR™ 1-F with an Osmolality Range of 290 to 340 mOsm/kg to Induce Endodermal and Mesodermal Cell Lineages and Less Efficiently Ectodermal Cell Lineages Using the methods described in Examples 6 and 7 and media mTeSR™ 1-F 270, 290, 320 and 340 mOsm/kg, H1 hESC were used to form EBs and induce cells of the different germ layers. EBs were cultured and adhered as described by the methods in Example 11. In comparison to mTeSR™ 1-F 260-280 mOsm/kg used in the previous example, clearly morphological differences are observed with osmolalities higher than 280. At an osmolality of 290 mOsm/kg, fewer rosettes were observed as compared to the lower osmolalities. The cell morphologies that can be observed after attaching the EBs are shown in FIG. 10. FIG. 17 shows an immunocytochemical staining (see Example 17) for Nestin and Sox1 on cells induced in mTeSR™ 1-F 270 mOsm/kg and mTeSR™ 1-F 340 mOsm/kg. Whereas many rosettes were observed using media with the osmolality of 270 mOsm/kg, the other 3 osmolalities showed a decrease in rosette formation. Furthermore, Nestin and Sox1 expression did not overlap in medium mTeSR™ 1-F 340 mOsm/kg to the same extent as in medium mTeSR™ 1-F 270 mOsm/kg. Most likely the other cell lineages present in the attached EB colonies were of endodermal and mesodermal origin as evident by their flat and "cobblestone-like" cells as well as flat cells and cells with a spindle-like morphologies, as published before (Odorico et al., 2001; Ferreira et al., 2007, Gerrard et al., 2005) (see FIG. 10). It is possible that these mesodermal and endodermal progenitor cells express Nestin, a phenomenon that has been described before (Wiese et al., 2004). As shown in FIG. 11, these cells look flat compared to the Nestin/Sox1 double-positive cells.

Figure 12:
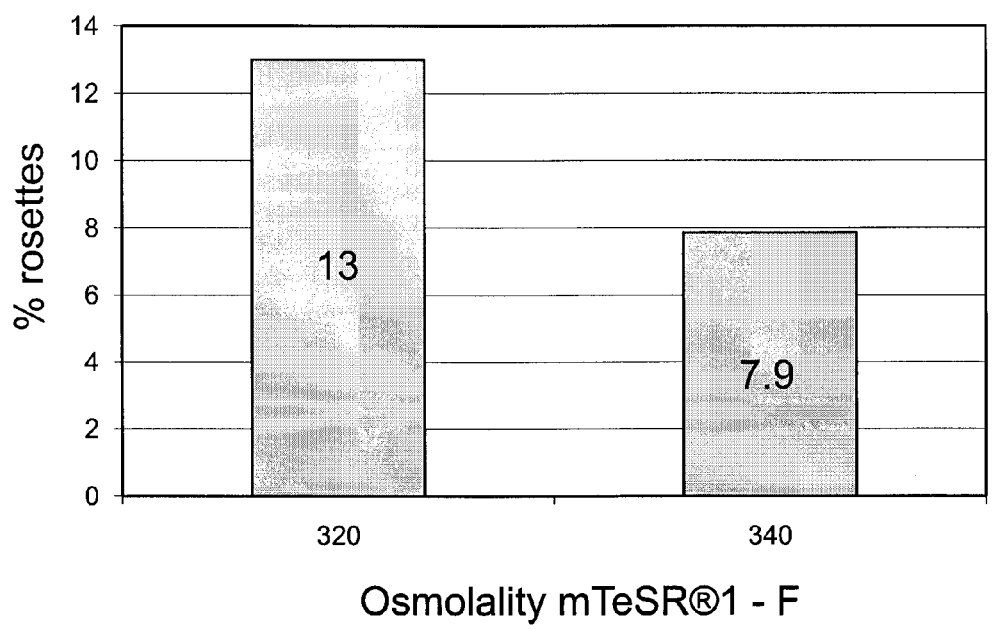
FIG. 12 shows the average rosettes counts of individual experiments where EBs were induced and cultured in mTeSR™ 1-F 320 mOsm/kg (13%) or mTeSR™ 1-F 340 mOsm/kg (7.9%).

Using the scoring criteria described in Example 12, the percentages of rosettes structures and therefore of ectoderm/neural progenitor cells was estimated and the percentages of experiments performed with mTeSR™ 1-F 320 and 340 mOsm/kg are shown in FIG. 12.

Example 14. Selective Detachment of Neural Rosette Colonies and Plating of Neural Progenitor Cells from Adherent EB-Cultures in mTeSR™ 1 260-280 mOsm/kg but not in mTeSR™ 1 340 mOsm/kg After a minimum of 3 days of culture in adherent conditions, with a cultivation time of 5-6 days, the colonies generated by mechanical trituration of EBs as described in Example 12, were chemically dissociated using optionally 1×PBS (Ca, Mg free), pH 7.4. An alternative chemical method may be used as well as a chemical method combined with the use of an enzyme. Also, the enzyme may be used alone or in combination with a mechanical method. Optionally, the enzyme is Accutase™.

Figure 13:
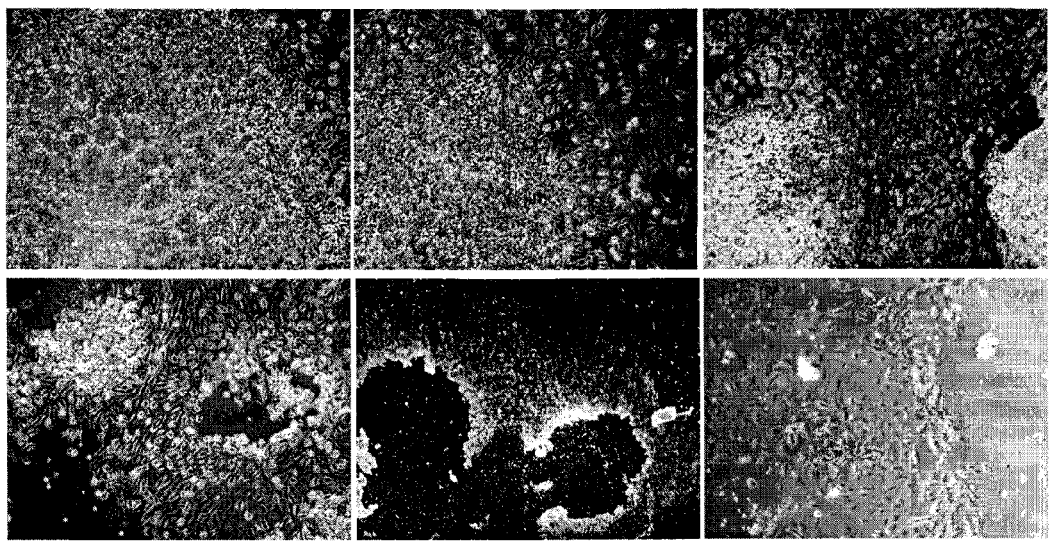
FIG. 13 shows pictures of cell morphologies during the selective neural progenitor dissociation procedure using 1×PBS (Ca, Mg free), pH 7.4. Upper row, left picture: rosette colonies before dissociation. Upper row, middle: during dissociation (20 min), upper row, right picture: during dissociation (40 min). Lower row, left picture: during dissociation (60 min), lower row, middle: after dissociation (when neural progenitor cells were lifted off by trituration (90 min), lower row, right: cells that remained on dish after trituration. Magnifications: all, except lower row left and middle: 10×; lower row left and middle: 2×.

The purpose was to obtain a single neural progenitor cell population that could be further propagated. This method was found to selectively allow for collection of neural progenitor cells. This is a novel attribute of 1×PBS (Ca, Mg free), pH 7.4 and has not been described before. Other cell types do not lift off the plate as efficiently and are not collected in the subsequent trituration step. FIG. 13 demonstrates the time-course of morphological changes/lifting off of the neural progenitor cells from the plate.

Figure 14:
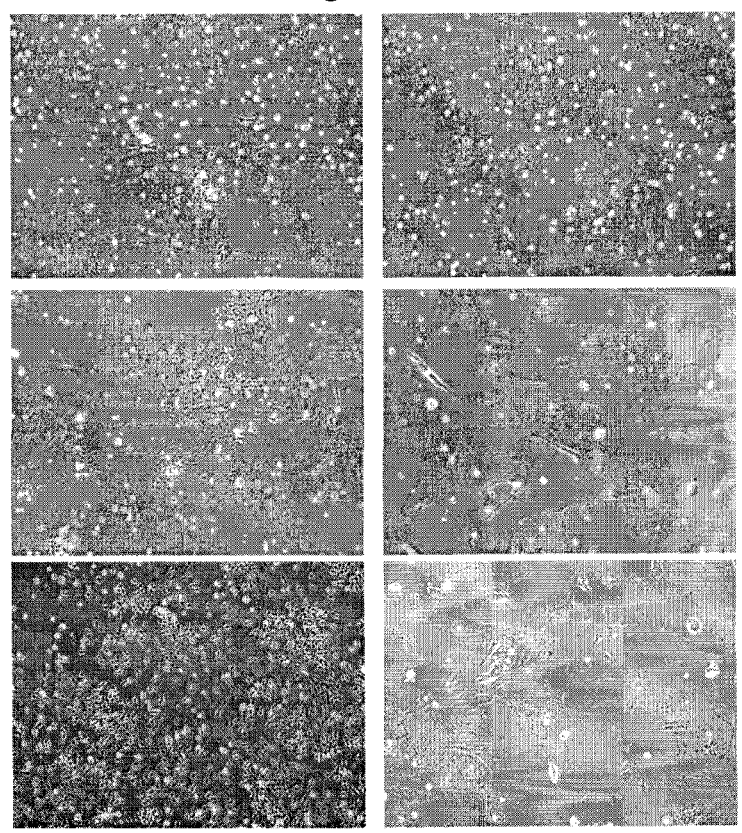
FIG. 14 shows neural progenitor cells plated after selective dissociation with 1×PBS (Ca, Mg free), pH 7.4 at day 3 (upper row), day 6 (middle row) and day 12 (lower row). Left column: mTeSR™ 1-F 270 mOsm/kg and right column: mTeSR™ 1-F 340 mOsm/kg. Magnification: left: 4×, right: 10×.
Figure 15:
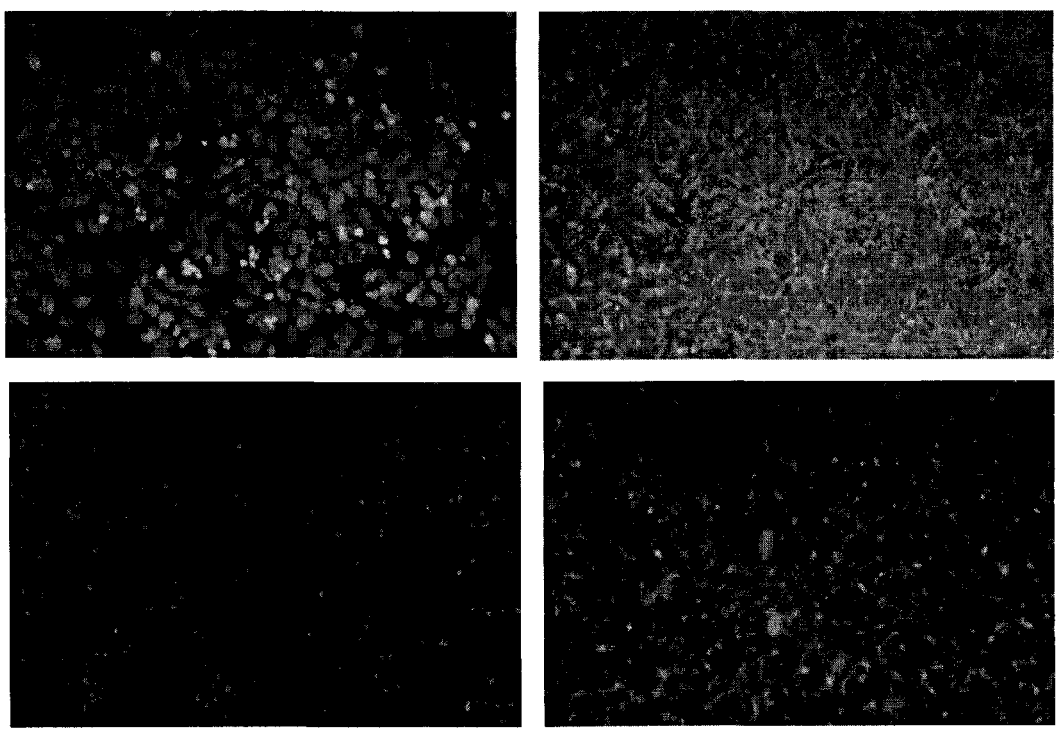
FIG. 15 shows neural progenitor cells 6 days after selective dissociation with PBS. Cells were plated and immunocytochemistry was performed using the Nestin antibody and the Sox1 antibody (right column). The left column represents the same cells stained with DAPI as nuclei-counterstaining. Cells were originally induced and grown in mTeSR™ 1-F 270 mOsm/kg (upper row) or mTeSR™ 1-F 340 mOsm/kg (lower row). Clearly, there are fewer cells stained with both antibodies present in the neural progenitor cells obtained in mTeSR™ 1-F 340 mOsm/kg. Magnification 20×.

The procedure includes a brief wash with 1×PBS (Ca, Mg free), pH 7.4 after aspirating the cell culture medium. Colonies were covered with 1 ml of 1×PBS (Ca, Mg free), pH 7.4 per single well of a 6-well dish. The dishes were incubated inside a sterile cell culture hood at room temperature for a minimum of 30 minutes, optionally 90 minutes up to a maximum of 2 hours. Colonies containing neural progenitor cells started peeling off of the plate after 60 minutes (see FIG. 13). The optimal time-point for harvesting the cells was determined by trying to triturate the cells gently (usually 90 minutes). If the cells didn't lift off the plate using mild trituration, the cells were further incubated with 1×PBS (Ca, Mg free), pH 7.4. Once the cells lifted off easily, they were further triturated (optionally 5-10×), which produced a nearly single cell suspension. Cells displaying a flat morphology and not being of neural fate, stayed attached to the plate. The cell suspension was transferred to a conical 15 mL tube and centrifuged at 300×g for 5 minutes. After resuspending the cells in 1 ml of mTeSR™ 1-F 270 mOsm/kg containing bFGF (10 ng/mL), the cells of a single 6-well were plated onto pre-coated poly-L-Ornithine/Laminin 6-well dishes (see Example 18) containing 3 glass slides (12 mm diameter) per well. A media change was performed every second day. Under these culture conditions the cells could be kept undifferentiated for at least 3 passages optionally more (see Example 16) and were also further processed for immunostaining to identify the neural progenitor cells using the procedure described in Example 16. The detachment with 1×PBS (Ca, Mg free), pH 7.4 is very efficient and selective for neural rosettes and eliminates the simultaneous harvesting of contaminating non-neural cells during the step. FIG. 14 shows plated neural progenitor cells after 3, 6 and 12 days of plating and FIG. 15 shows an immunocytochemical staining performed at day 6 after plating of the cells for the neural cell markers Nestin and Sox1.

Human ESCs that were initially subjected to medium mTeSR™ 1-F 270 mOsm/kg, and were dissociated into neural progenitor cells using 1× PBS (Ca, Mg free), pH 7.4, gave rise to typical rosette structures, which co-stained for Nestin and Sox1.

Neural progenitor cells co-expressing Sox1 and Nestin could not be obtained from attached EB colonies that were initially formed and cultured in mTeSR™ 1-F 340 mOsm/kg as described in Examples 6, 7 and 13.

To summarize the influence of media osmolality on germ layer induction and especially induction of ectodermal fate followed by selection of neural progenitor cells, Examples 12 and 13 clearly demonstrate that the osmolality of the medium used for EB formation and cultivation directs the germ layer fate undertaken by pluripotent human stem cells on their way to differentiating towards a mature cell type. Example 14 shows that those neural progenitor cells obtained in medium with an osmolality range of 260-280 mOsm/kg can be passaged selectively and cannot be obtained from EBs generated and grown in mTeSR™ 1-F 340 mOsm/kg, again underlining the effect of different osmolalities on cell fate determination.

Figure 16:
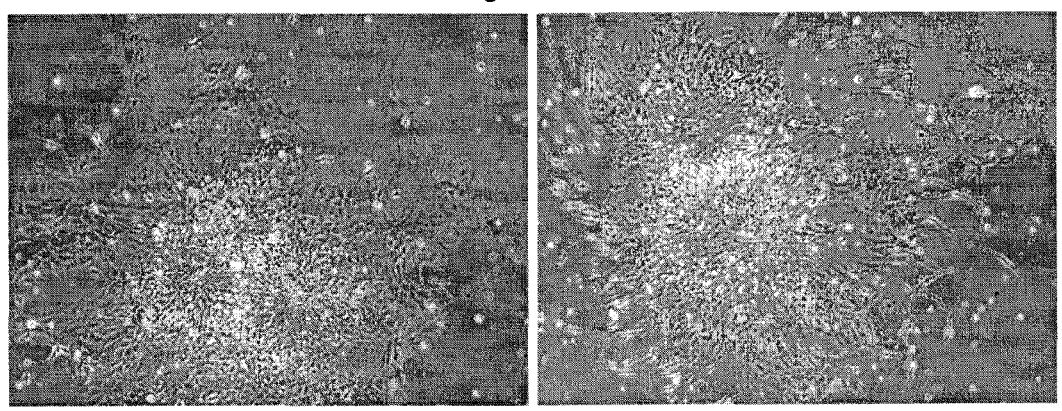
FIG. 16 shows manually selected rosette colonies from EBs formed, grown and attached in mTeSR™ 1-F 270 mOsm/kg, 2 days after selection. Magnification 10×.

Example 15. Selection of Neural Progenitor Cells from Neural Rosettes by a Mechanical Selection Procedure To obtain a highly pure population of neural progenitor cells, neural rosettes were manually isolated from attached EB colonies (as generated in Example 11). For this purpose, a bent 26-gauge needle attached to a syringe was used. Rosettes were isolated by cutting an area with many rosettes present from the Poly-L-ornithine/laminin matrix using the needle and removing them from the dish with a 200 μl pipette tip. They were transferred into a sterile 1 ml tube. After pooling of all excised rosette structures, they were mechanically disrupted with a 200 μl pipette tip and plated onto a poly-L-ornithine/laminin coated dish (Example 18). Rosettes isolated from 2-3 single 6-wells were plated into one 6-well. This procedure gave rise to a highly pure population of neural progenitor cells, which formed small clusters containing rosettes as shown in FIG. 16 one day after plating them down onto poly-L-ornithine/Laminin (see Example 18) coated dishes. The neural progenitor cells within these clusters could then be further passaged and maintained according to the method described in Example 16.

Example 16. Method to Passage Neural Progenitor Cells

Various methods to passage neural progenitor cells are available. The method used below works in a consistent manner to generate single cell suspensions of neural cells. When cultured neural progenitor cells from Example 14 or 15 above reached 80-90% confluency (after 3-4 days), neural progenitor cells were passaged by brief exposure to 0.5% trypsin-EDTA (STEMCELL TECHNOLOGIES INC. catalogue #07910). The passaging is performed every 3-4 days and outlined below. For this step, medium was aspirated and the cells were washed once with 1×PBS (Ca, Mg free), pH 7.4. After aspirating the PBS, 500-600 μl of 0.5% trypsin-EDTA was added to a 6-well of neural progenitor cells. The dish was incubated at 37° C. until cells started lifting off the dish or for a maximum time of 5 minutes. Trypsin was inactivated by adding an equal volume of medium or 1×PBS (Ca, Mg free), pH 7.4 containing 10% of fetal bovine serum (STEMCELL TECHNOLOGIES INC. catalogue #06902). Cells were carefully triturated using a 5 ml serological pipette. The cell suspension was centrifuged at 300×g for 5 minutes. The supernatant was aspirated and the cell pellet was gently tapped to dislodge the cells. 500 μl of fresh culture medium were added (mTeSR™ 1-F 270 mOsm/kg+10 ng/ml bFGF) and the cells were triturated 2-4 times using a 1000 μl pipette tip. Cells were split at a 1:3 to 1:6 ratio. Media changes were performed every second day. FIG. 17 shows passaged neural progenitor cells at passage 1, 2 days after plating.

Example 17. Identification by Immunocytochemistry Based on Marker Expression of Neural Progenitor Cells Induced and Grown in mTeSR™ 1-F 270 and 340 mOsm/kg Progenitor cells of ectodermal origin were induced to various extent as described in Examples 6, 7, 9, 11 and 13 using mTeSR™ 1-F 270 or 340 mOsm/kg. Disrupted EBs (see Example 11 and 13) were seeded onto 6-wells containing 3 glass coverslips (VWR microcoverglass, catalog #89015724) per well (coated with poly-L-ornithine/laminin). To assess the percentage of ectodermal and therefore neural progenitor cells, immunocytochemistry for neural markers was performed (FIG. 11). The presence of neural progenitor cells after selection and propagation (Example 14, 15 and 16; FIGS. 14 and 17 were also investigated. Optionally 2 days after the cells had been plated down, cells were washed once with 1×PBS (Ca, Mg free), pH 7.4 and the fixed with 4% paraformaldehyde for 20 minutes at room temperature. The coverslips were washed twice with 1×PBS (Ca, Mg free), pH 7.4 and were stored in 1×PBS (Ca, Mg free), pH 7.4 at 4° C. until immunocytochemistry was performed.

On the day of immunocytochemistry, cells were briefly rinsed with room temperature 1×PBS (Ca, Mg free), pH 7.4. Blocking solution consisting of 10% normal donkey serum (Jackson ImmunoResearch Laboratories, catalog #017000121) and 0.2% Triton X (Sigma, catalog #T9284) was applied for 1 hour at room temperature with gentle shaking. Subsequently, the primary antibody solution containing the antibody in the appropriate concentration (see below) and 2% normal donkey serum was added for one hour at room temperature.

Antibodies were directed against Sox1 (goat α-Sox1, 1:200, Neuromics, catalogue #GT15208) and Nestin (mouse α-Nestin, 1:3000, Millipore, catalog #MAB5326) to identify early embryonic ectoderm. After incubation with the primary antibody, cells were washed 3×15 minutes with 1× PBS (Ca, Mg free), pH 7.4 at room temperature with gentle shaking. Primary antibodies were detected using secondary antibodies generated in donkey directed against the species the primary antibodies were of origin, conjugated to FITC (α-mouse) (Jackson Immunoresearch Laboratories, catalog #715095150; 1:500) or Texas red (α-goat) (Jackson Immunoresearch Laboratories, catalog #705075003; 1:500); by a 30-minute incubation step. To wash away unspecific binding, the cells were washed 3× using 1×PBS (Ca, Mg free), pH 7.4. To mount the coverslips, they were briefly dipped in distilled water. One drop of mounting solution containing DAPI (Vector laboratories, catalog #H-1500) was applied to the coverslip and with the cells facing downwards, the coverslip was mounted on a glass slide (Corning microslides, catalog #2947). After complete drying of the mounted coverslip on the glass slide, the immunofluorescence was visualized under a fluorescent microscope using the appropriate filters for each fluorophore. The co-expression of Nestin and Sox1 was observed in cells containing neural rosettes, which were induced and cultured in mTeSR™ 1-F 270 mOsm/kg as shown in FIG. 8. FIG. 11 shows co-expression of Nestin and Sox1 in neural progenitor cells cultured in mTeSR™ 1-F 270 mOsm/kg as compared to mTeSR™ 1-F 340 mOsm/kg. Attached EB colonies and neural progenitor cells induced in mTeSR™ 1-F 340 mOsm/kg, showed overall less staining with the 2 markers.

Example 18. Coating of Dishes with Poly-L-Ornithine/Laminin

In all previously described examples where cells or EBs were allowed to attach to a culture vessel, an extracellular matrix or combination of matrices were prepared prior to culture. For example, plastic polystyrene cell culture dishes as well as glass coverslips localized in either single wells of a 24-well plate or as triplicate in single 6-wells, were coated optionally with poly-L-ornithine/laminin. Briefly, plastic culture dishes or coverslips were covered with poly-L-ornithine (Sigma, catalog #P4957) optionally over night at least for 2 hours at room temperature. Dishes were washed twice with room temperature 1×PBS (Ca, Mg free), pH 7.4. The third wash consisted of sterile distilled water or DMEM/F12. Laminin (Sigma, catalog #L2020) at a concentration of 5 μg/ml was dissolved in ice-cold DMEM/F12. After aspirating off the water or DMEM/F12 from the dishes, using an ice-cold serological pipette, the laminin solution was added.

1 ml was used for a single 6-well or 500 μl for a single 24-well. Plates were placed at 37° C. for optionally 12 hours, at least 2.5 hours. Before plating cells, the laminin solution was discarded and medium added.

Figure 18:
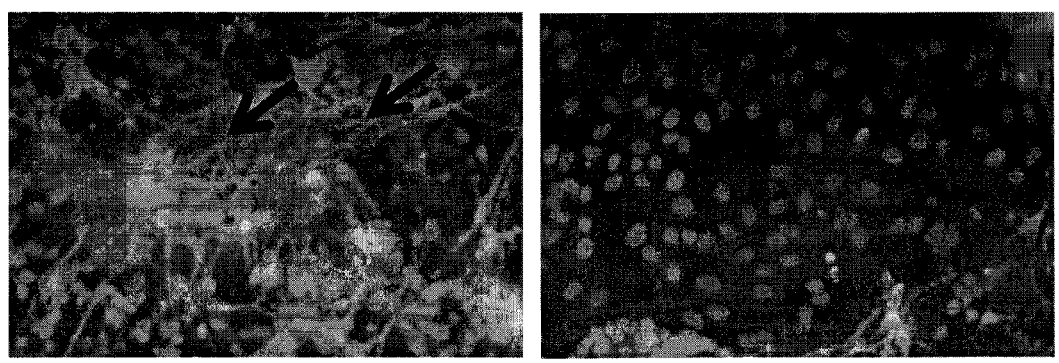
FIG. 18 shows neurons stained with anti TUJ1 antibody derived from neural progenitor cells cultured in mTeSR™ 1-F 270 mOsm/kg (left) but not in mTeSR™ 1-F 340 mOsm/kg (right). TUJ1 and Sox1 antibody staining is displayed with separate arrows. Sox1 is not expressed in neurons. Magnification 20×.

Example 19. Differentiation of Neural Progenitor Cells into Neurons and Their Detection Differentiation of neural progenitor cells was initiated by withdrawal of bFGF from the mTeSR™ 1-F 270 mOsm/kg medium and addition of factors such as but not limited to GDNF, cAMP. The cells were incubated with this medium for a minimum period of 5 days. Medium was changed every 2 days. FIG. 18 shows neurons stained (for immunocytochemical staining method see example 17) by the mature neuronal marker TUJ1. Neurons could only be derived from hESCs initially induced as EBs as described in Examples 7, 9 and 11 using mTeSR™ 1-F 270 mOsm/kg (left side of FIG. 18) and not from hESCs initially induced as EBs as described in Examples 7 and 13 using mTeSR™ 1-F 340 mOsm/kg (right side of FIG. 18).

Example 20. Culture of Human Pluripotent Stem Cells as Aggregates in Defined Serum-Free Medium on BD Matrigel™ Coating Human pluripotent cells were maintained on BD Matrigel™ coated dishes in defined serum-free medium. A detailed protocol can be found in manual #29106 "Maintenance of hESCs AND hiPSCs in mTeSR™ 1 and TeSR™ 2" by STEMCELL TECHNOLOGIES INC. for the maintenance of human pluripotent stem cells which includes the procedure for BD Matrigel™ coating. The procedure described in this example for passaging the cells was applied for human embryonic stem cell lines H1 and H9 and for the human induced pluripotent stem cell line 4D1. Cells were passaged when the colonies were large, beginning to merge, and had centers that are dense and phase-bright compared to their edges (see FIG. 1). Depending on the size and density of seeded aggregates, cultures were passaged 5-7 days after initial seeding.

Medium was aspirated from the stem cell culture and cells were rinsed with DMEM/F-12 (2 mL/well). 1 mL of dispase (STEMCELL TECHNOLOGIES INC. catalogue #07923) was added per well at a concentration of 1 mg/mL. The dish was placed at 37° C. for 7 minutes.

Once the colony edges appeared slightly folded back, dispase was removed, and each well was gently rinsed 2-3 times with 2 mL of DMEM/F-12 per well to dilute away any remaining dispase. 2 mL/well of DMEM/F-12 or mTeSR™ 1 was added to the well and colonies were scraped off with a cell scraper (e.g. Corning Catalog #3010) or a serological pipette tip.

The detached cell aggregates were transferred to a 15 mL conical tube and the well was rinsed with an additional 2 mL of DMEM/F-12 to collect any remaining aggregates. The rinsed media containing remaining cells was added to the same 15 mL tube.

The 15 mL tube containing the aggregates was centrifuged at 300×g for 5 minutes at room temperature (15-25° C.). The supernatant was aspirated. For each well of hESC aggregates collected in the 15 mL tube, 1-2 mL of mTeS®1 were added. The pellet was resuspended gently by pipetting up and down using a P1000 micropipette (1-2 times). Cells were maintained as aggregates. Using the "clump count" method the number of clumps was estimated. To enumerate clumps that are likely to attach and grow of the right size (~50-60 µm in diameter), a micrometer placed in the microscope eyepiece is used. To perform the clump count, 30 µL of DMEM/F-12 were aliquoted into 2 wells of a 96-well flat-bottom plate. A "+" was drawn centered on the bottom of these wells to serve as a counting grid. 5 µL of a freshly mixed clump suspension was added to each well. Clumps were counted in duplicate that were approximately 3500 µm$^2$ or greater. This corresponds to clumps with a diameter of approximately 60 µm. The total number of clumps per µl was estimated using the formula:

Total # of clumps per µl=x clumps counted/5 µL total volume of suspension

A defined number of clumps according to the size of the well or dish that is being seeded was plated. The volume of clump suspension (y) used to seed new dishes was calculated using the guide in Table 1 for appropriate seeding densities. For example (y) for a 6-well equals: 350/# clumps counted per µl.

Human pluripotent stem cell aggregates were plated with 2 mL of mTeSR™ 1 per new 6-well coated with BD Matrigel™. The plate was moved in several quick, short, back-and-forth and side-to-side motions to disperse cells evenly across the surface of the wells. The plate was placed in a 37° C. incubator. The protocol above was applied to H1, H9 and 4D1 cells and cells were used as consistent cell source for the examples described in this disclosure.

Figure 19:
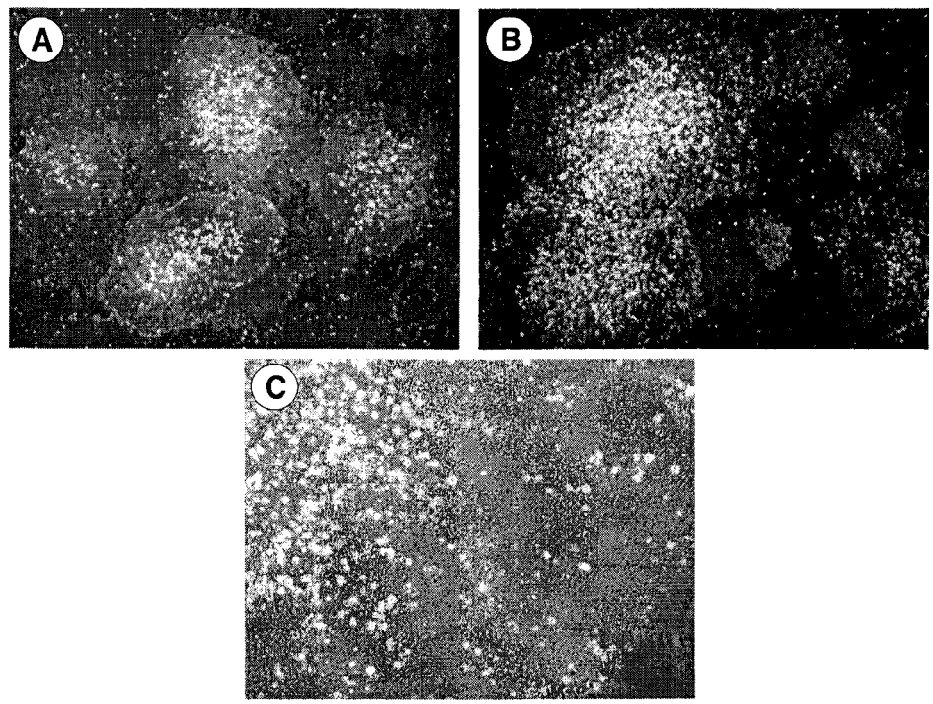
FIG. 19 shows human embryonic stem cell line H1 at day 5 of passage 39 (A) and human induced pluripotent stem cell line 4D1 at day 5 of passage 33 (B) cultured on BD Matrigel™. Magnification: 2× (A, B) and 10× (C).

FIG. 19 shows undifferentiated H1 hESCs (A) and 4D1 iPSCs (B) on day 5 of culture.

Example 21. Culture of Human Pluripotent Stem Cells as Single Cells in Defined Serum-Free Medium with BD Matrigel™ Coating Human pluripotent stem cells were maintained on BD Matrigel™ coated 6-well dishes in defined serum-free medium such as mTeSR™ 1. In this example, the human embryonic stem cell line H9 cells was cultured as single cells and these cells were used for Example 37. The time of passaging was determined based on the confluency of cell colonies. Cell colonies reached approximately 70% confluency (FIG. 20A) 5 to 6 days of culture after the previous passage.

To passage cells, medium was aspirated from the stem cell culture and cells were rinsed with DMEM/F-12 (2 mL/well). 1 mL of Accutase (STEMCELL TECHNOLOGIES INC. catalogue #07920) was added per well. The dish was placed at 37° C. for 8-10 minutes until all cells detached.

5 ml of DMEM/F-12 was added to the Accutase and cell aggregates were dissociated into a single cell suspension using a 5 mL serological pipette. Cells were transferred to a 15 mL conical tube and the well was rinsed with an additional 2 mL of DMEM/F-12 to collect any remaining cells. The rinsed media containing remaining cells was added to the same 15 mL tube.

Figure 20:
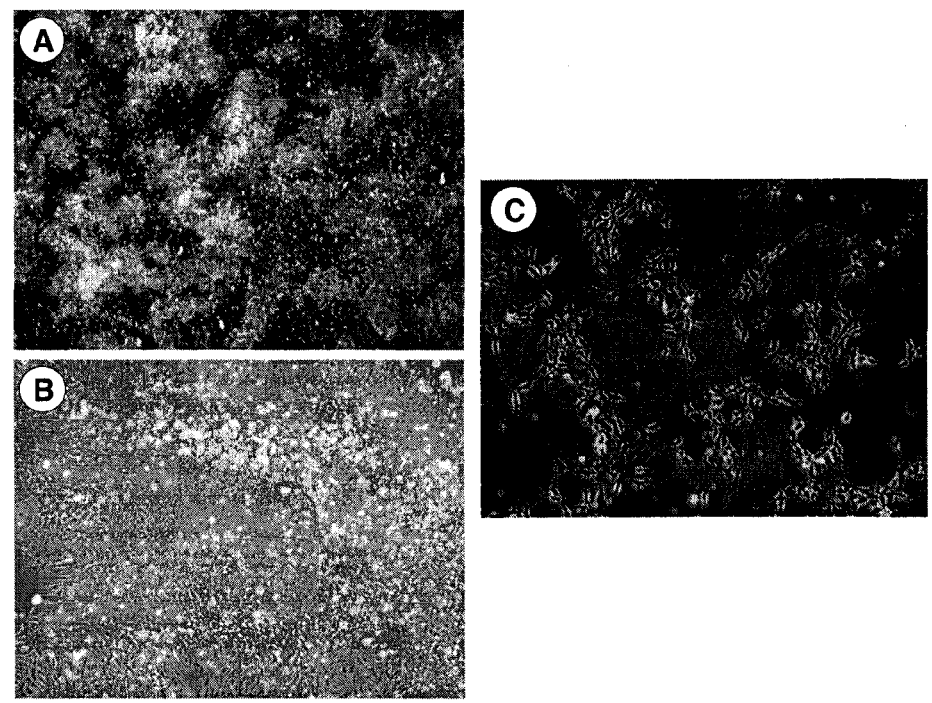
FIG. 20 shows human embryonic stem cell line colonies (H9) at approximately 70% confluency at day 5 of culture (A, B) after passage as single cell suspensions and one day after H9 were re-plated at a density of 2×10⁴ per cm² (C). Magnifications 2× (A), 10× (B and C).

The 15 mL tube containing the single cell suspension was centrifuged at 300×g for 5 minutes at room temperature (15-25° C.). The supernatant was aspirated. Stem cells collected from each well and then transferred to the 15 mL tube were routinely resuspended in 1-2 mL of mTeS®1. The pellet was resuspended gently by pipetting up and down using a P1000 micropipette (1-2 times). Viable cells were counted using standard techniques, by diluting a 10 µL sample of the cell suspension 1:10 in 90 µL of trypan blue (Invitrogen, catalog #15250061) and counting unstained cells on a haemocytometer. The number of cells per µl allows calculation of the volume of cells to be plated into fresh Matrigel™ coated 6-well dishes. Cells were plated either at a density of $3 \times 10^3$-$5 \times 10^3$ cells per cm$^2$ with Y27632 rock inhibitor (STEMCELL TECHNOLOGIES INC. catalogue #07171/2) at a final concentration of 10 µg/mL to enhance cell survival after plating (Watanabe et al, 2007) or without Y27632 at a density of $2 \times 10^4$-$5 \times 10^4$ per cm$^2$. FIG. 20(C) shows pluripotent stem cells (H9) plated at a density of $2 \times 10^4$ per cm$^2$ one day after plating.

Example 22. Morphological Assessment of Pluripotency of Human Pluripotent Stem Cell Lines Grown as Aggregates or Single Cells in mTeSR™ 1 on BD Matrigel™

For the successful induction of germ layers, a highly pure population of pluripotent stem cells was used. For the following examples, the human embryonic stem cell lines H1, H9 and the human induced pluripotent cell line 4D1 were used. The following criteria were employed to assess the morphology and quality of cells (described in technical manual #29106 by STEMCELL TECHNOLOGIES INC.): Undifferentiated human pluripotent stem cells, grew as compact, multi-cellular colonies, as shown in FIGS. 1 and 19. They exhibited a high nuclear-to-cytoplasm ratio and prominent nucleoli. These colonies were characterized by a distinct border. Healthy hESC (and iPSC) colonies were multilayered in the center, resulting in clusters of phase-bright cells when viewed under phase contrast. Differentiation was characterized by loss of border integrity, gross non-uniform cell morphology within the colony and the emergence of obvious alternate cell types. The percentage of colonies displaying differentiated cell types was estimated by observation of the colonies under the microscope (using 4× and 10× objectives). For efficient induction of germ layers, cultures that displayed less than 15% of differentiated colonies were used in the following examples with exception of Example 37 where cultures with 40-50% of differentiation were used.

The criteria to assess pluripotency was used for human pluripotent stem cells cultured as aggregates (Example 20) as well as cells cultured as single cells (Example 21).

Example 23. Media Formulations with Different Osmolality Ranges: Factor Free mTeSR™ 1 Medium at an Osmolality of 270 mOsm/kg The complete media formulation and method of preparation for modified TeSR (mTeSR™ 1, STEMCELL TECHNOLOGIES INC., catalogue #05850) is published in Ludwig et al, Nature Methods 3(8): 637, 2006. It is based on the original TeSR formulation published in Ludwig et al., Nature Biotechnology 24(2): 185, 2006, with the following modification: substitution of human serum albumin (HSA) with bovine serum albumin (BSA).

To manufacture the factor free mTeSR™ 1 (mTeSR™ 1-F) media, a 5× supplement was produced containing all of the mTeSR™ 1 reagents at 5-fold concentrations, with the exceptions of the following 5 factors: GABA, pipecolic acid, bFGF, TGFβ1, lithium chloride. The components for the media are shown in Table 2.

After mixing the components of the 5× supplement together, the pH was adjusted to 7.4 by adding 10N NaOH. The osmolality of the solution was measured using a standard osmometer. The initial osmolality of the 5× supplement was usually around 100 mOsm/kg, and salt (NaCl) was used to increase the osmolality while taking into account that the 5× supplement is combined with 400 ml of the base medium DMEM/F12 (Hyclone, catalog #SH30004) to obtain mTeSR™ 1-F. The amount of salt that had to be added to the 5× supplement was calculated using the following formula: To obtain an osmolality of 270 after mixing the 5× supplement and the basal medium:

[270−((0.8×300 mOsm)+(0.2×100 mOsm))]/2000× 58.44×1.05=0.30 g/L of NaCl

The x amount of NaCl was added to the 5× supplement to obtain mTeSR™ 1-F 270 mOsm/kg.

Example 24. Generating a Single Cell Suspension of Human Pluripotent Cells for EB Formation in AggreWell™ 800

The procedure to generate single cells from human pluripotent stem cells and using them in the AggreWell™ 800 protocol and device is described in technical manual 29146 (STEMCELL TECHNOLOGIES INC.). The human pluripotent stem cell lines that were dissociated into single cell suspensions and were used to set up EBs in AggreWell™ 800 in the following examples were human embryonic stem cell lines H1, H9 and induced pluripotent stem cell line 4D1. The details how to obtain a single cell suspension from pluripotent stem cells are described in Example 6. In this example, the medium used to resuspend the cells was mTeSR™ 1-F 270 mOsm/kg (see Example 23). Setting up EBs in AggreWell™ 800 is described in the following example.

Example 25. EB Formation from Human Pluripotent Stem Cells in mTeSR™ 1-F with an Osmolality of 270 mOsm/Kg Using a Microwell Device (AggreWell™ 800) and Subsequent Suspension Culture in the Same Medium Single cell suspensions of human pluripotent stem cells (in this example the human induced pluripotent stem cell line 4D1 was used) were obtained as described in Example 24. Here, EBs with a size of 2000 cells per EB were generated in AggreWell™ 800. In general, EBs ranging from sizes of 1000 cells to 20000 cells can be generated in AggreWell™ 800. The plate was prepared as described in Example 7. Compared to an AggreWell™ 400 well, a single well of on AggreWell™ 800 plate contains approximately 300 microwells. As shown in table 3, 600,000 cells needed to be added to each well of the plate to obtain EBs with 2,000 cells in AggreWell™ 800. The volume of the single cell suspension generated in Example 22 containing 600,000 cells was determined based on the cell counts obtained (for cell counting see Example 6). This volume was added to each well of the AggreWell™ 800 plate previously prepared (see Example 7). The medium used in this example was mTeSR™ 1-F with an osmolality of 270 mOsm/kg. The cell suspension was distributed into the ~300 microwells of an AggreWell™ 800 plate. Medium was added to a final volume of 2 mL per well. The AggreWell™ 800 plate was centrifuged at 100×g for 3 minutes to capture the cells in the microwells. Plates were incubated at 37° C. with 5% $CO_2$ and 95% humidity for 24 hours.

Figure 21:
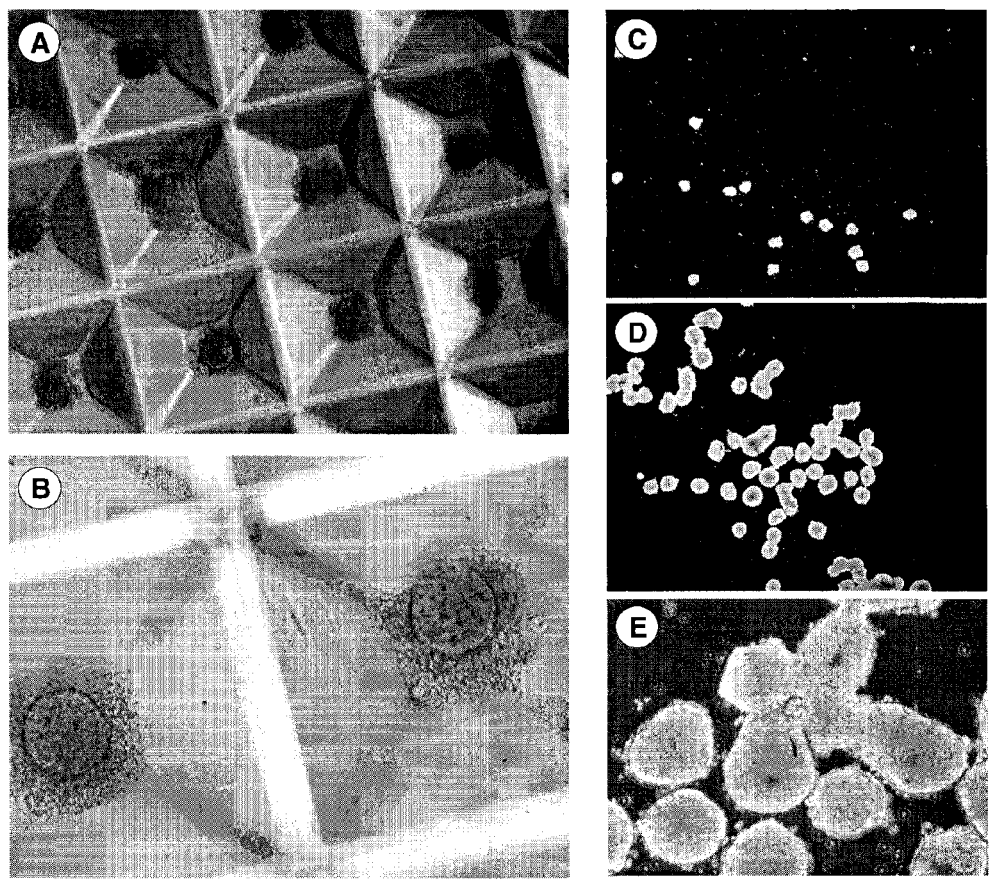
FIG. 21 shows EBs generated from 4D1 pluripotent stem cells inside the microwells of an AggreWell™ 800 plate after 24 hours and before harvest (A and B). EBs harvested from AggreWell™ 800 after 2 days (C) and 4 days (D and E) in suspension culture. Magnifications: 4× (A), 10× (B,E), 2× (C,D).

After 24 hours, EBs were harvested by gently pipetting up and down the medium in the AggreWell™ 800 microwells— 2-3 times with a 1 mL disposable pipette tip to dislodge most of the EBs. To harvest the EBs, the suspension was passed through an inverted 40 μm nylon cell strainer (Falcon) sitting on top of a 50 mL conical tube to remove single cells and debris. The AggreWell™ 800 surface was washed a further 5-10 times with 1 mL each of DMEM/F-12, pipetting across the entire surface to dislodge all aggregates. All washes were applied onto the cell strainer membrane. The cell strainer was turned upside down, holding it close over a low-adherence 6-well. EBs were washed of the membrane using mTeSR™ 1-F 270 mOsm/kg medium. Approximately 5 ml of medium were used to remove the EBs from the nylon membrane holding the strainer over a single well of a 6-well ultra-low adherence dish (STEMCELL TECHNOLOGIES INC., catalog #27145). EBs were incubated in a standard tissue culture incubator, at 37° C., 5% $CO_2$ and 95% humidity for a period of 5 days, with a media change every 2-3 days. For this purpose, the dish was tilted towards one side and using a 1000-μl pipette tip, approximately half the volume of the medium was removed without disturbing the EBs. Fresh medium was added up to 5 ml. FIG. 21 shows EBs generated from 4D1 pluripotent stem cells inside the microwells of an AggreWell™ 800 plate after 24 hours before harvest (4× and 10× magnification) and the released EBs after 2 days and 4 days in suspension culture at 2× and 10× magnification.

Figure 22:
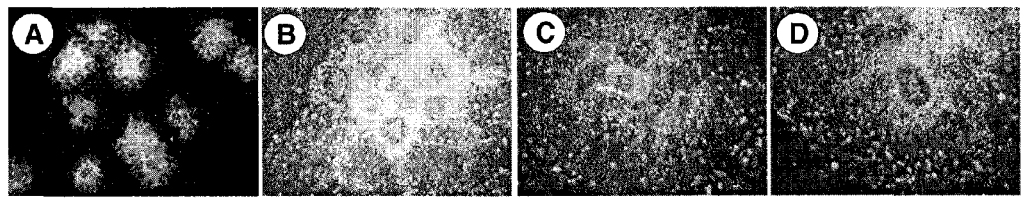
FIG. 22 shows representative images of neural rosettes observed in the EBs attached to poly-L-ornithine/laminin plates at day 3 (A-D). The attached EBs of ~2000 cells per EB shown here were previously generated from human induced stem cell line 4D1 using AggreWell™ 800. Magnifications: 2× (A), 10× (B-D).

Example 26. EB Formation from Human Pluripotent Stem Cells in mTeSR™ 1-F with an Osmolality of 270 mOsm/Kg Using a Microwell Device (AggreWell™ 800), Subsequent Suspension Culture Followed by Plating of EBs to Obtain Neural Ectoderm Single cell suspensions were obtained from human induced pluripotent stem cell line 4D1 as described in Example 24 and EBs were set up in AggreWell™ 800 in mTeSR™ 1-F with an osmolality of 270 mOsm/kg and were cultured in suspension culture as described in Example 25. EBs were plated after 5 days onto Poly-L-ornithine/Laminin coated 6-well plates (see Example 18 for coating of plates and Example 11 for the procedure for dissociation of EBs and subsequent plating the dissociated EBs). Three days after plating, the presence of ectoderm was assessed using the methods of Example 12. FIG. 22 shows neural rosettes in the attached plated EBs formed at a size of 2000 cells per EB from the human induced stem cell line 4D1.

Example 27. The Induction of Neural Ectoderm from Human Pluripotent Stem Cells in a Microwell Device (AggreWell™ 800) Containing mTeSR™ 1-F with an Osmolality of 270 mOsm/kg or mTeSR™ 1 with an Osmolality of 340 mOsm/kg Followed by Subsequent Culture and Plating of EBs in the Same Media Single cell suspensions were obtained from human induced pluripotent stem cell line 4D1 and human embryonic stem cell line H9 as described in Example 24. EBs were set up in AggreWell™ 800 as described in Example 25 with the exception of using two different media: mTeSR™ 1-F with an osmolality of 270 mOsm/kg and 340 mOsm/kg. EBs from 4D1 cells were set up in both media at a size of 2000 cells per EB using the calculations in Table 3. EBs from H9 cells were set up at a size of 5000 cells using the methods described in Examples 24 and 25 and calculations for EB size provided in Table 3 in both media: mTeSR™ 1-F with an osmolality of 270 mOsm/kg and 340 mOsm/kg. EBs were harvested from the microwell device after 24 hours as described in Example 25 with the difference to the protocol that a different technique was used to dislodge the EBs from the microwells for EBs containing 5000 cells per EB. To dislodge EBs larger than 3000 cells, large bore tips (e.g. Rainin Catalog #HR-1000 WS) or regular 1000 µl disposable pipette tips where the tip has been aseptically cut off to increase the bore size. In addition, to increase recovery of EBs from the AggreWell™ 800 wells, a regular 1000 µl disposable tip was used to dislodge the EBs and the wider (cut) tip was used to collect the EBs onto the cell strainer (see Example 25).

Figure 23:
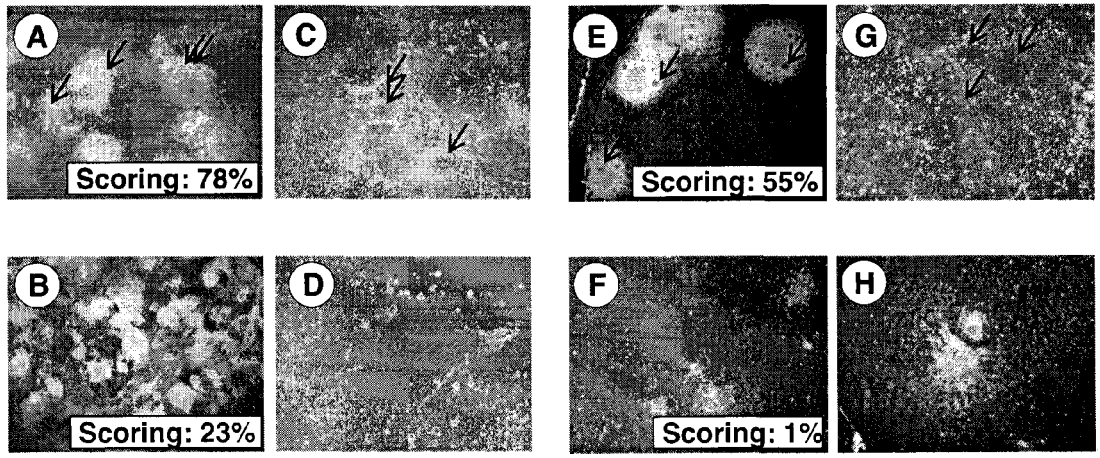
FIG. 23 shows neural rosettes (arrows for a few examples) observed in the EBs attached to poly-L-ornithine/laminin plates generated from cell lines 4D1 (A-D) and H9 (E-H). Attached EBs containing 2000 cells per EB (A-D) and 5000 cells per EB (E-H) cultured in mTeSR™ 1-F 270 mOsm/kg (A, B, E, F) or mTeSR™ 1-F 340 mOsm/kg (C, D, G, H). Scoring results are also indicated as % within the corresponding images. Magnifications 2× (A, C, E, G), 10× (B, D, F, H)

EBs were cultured in suspension culture as described in Example 25 and were plated after 5 days onto Poly-L-ornithine/Laminin coated 6-well plates (see Example 18 for coating of plates and Example 11 for plating the EBs down). 4 to 5 days after plating, the presence of ectoderm was assessed using the methods of Example 12. FIG. 23 shows neural rosettes in the attached plated EBs formed from both cell lines (H9 A-D, 4D1 E-H) in both media. To the experienced eye, there are clearly more neural rosettes present in medium mTeSR™ 1-F with an osmolality of 270 mOsm/kg compared to mTeSR™ 1-F with an osmolality of 340 mOsm/kg. Scoring of the neural rosettes was performed as described in Example 12 (4D1 attached EBs were scored at day 4, H9 attached EBs were scored at day 5) and shows higher percentages of neural rosette containing (colony displaying more than 50% of area covered by neural rosettes) colonies in mTeSR™ 1-F with an osmolality of 270 mOsm/kg compared to mTeSR™ 1-F with an osmolality of 340 mOsm/kg. The scoring results are also indicated in FIG. 23.

Example 28. Continual Culture of EBs of Different Sizes within Microwell Device (AggreWell™ 400) in mTeSR™ 1-F with an Osmolality of 270 mOsm/kg for 5 Days to Induce Ectoderm A single cell suspension from the human embryonic stem stem cell line H9 was obtained as described in Example 6. EBs were set up as described in Example 7 with the exception that only mTeSR™ 1-F with an osmolality of 270 mOsm/kg was used. Different sizes of EBs were formed: 500 cells, 1000 cells and 2000 cells. Single cell suspension volumes which were added to the AggreWell™ 400 wells were calculated according to cell counts and the numbers given in Table 3. In this example, instead of harvesting the EBs from the AggreWell™ 400 plate after 24 hours (see Example 9) the EBs were left in the microwells for up to 11 days. Medium was changed every day by removing approximately 1.5 mL of media from an individual AggreWell™ 400 well using a micropipettor outfitted with a disposable 1 mL tip. Pre-warmed (37° C.) fresh mTeSR™ 1-F 270 mOsm/kg medium was dispensed slowly into the well thereby making sure not to disturb the EBs in the microwells.

Figure 24:
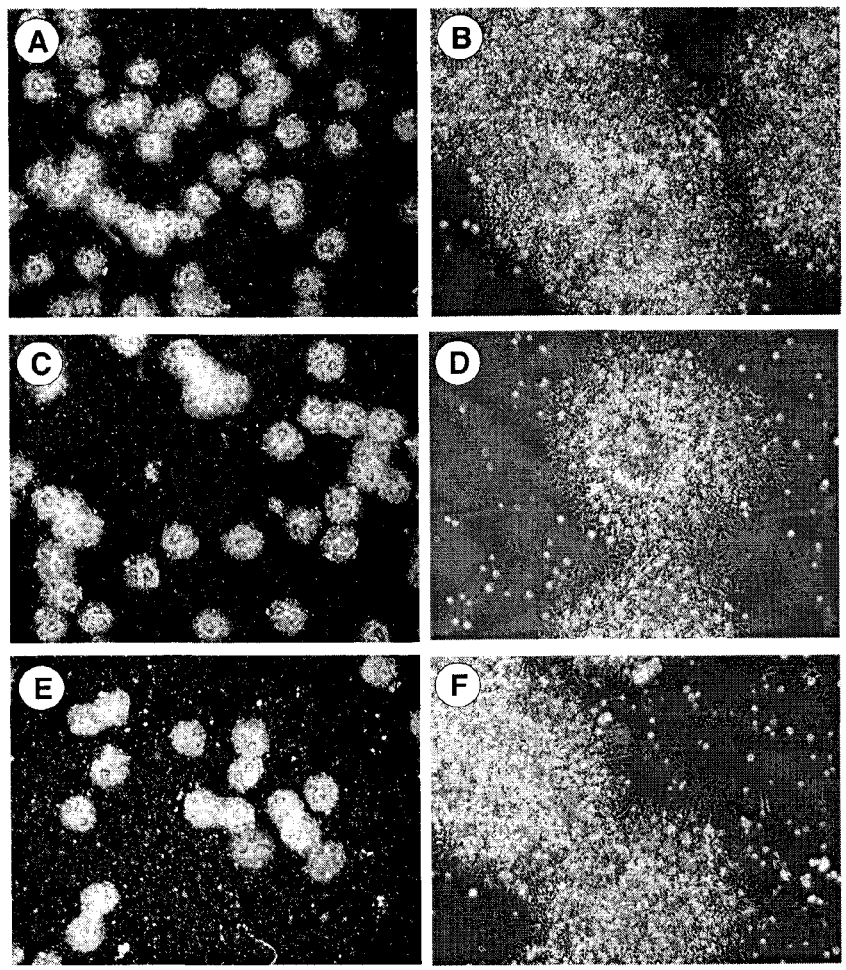
FIG. 24 shows attached EBs 1 day after plating of different sized EBs previously generated from H9 human embryonic stem cells. The different size of EBs are as follows: 500 cells per EB (A and B), 1000 cells per EB (C and D) and 2000 cells per EB (E and F). Magnifications 2× left (A, C and E), 10× right column (B, D and F).

Example 29. Induction of Neural Ectoderm from Human Pluripotent Stem Cells in mTeSR™ 1-F with an Osmolality of 270 mOsm/kg Using a Microwell Device (AggreWell™ 400) to Generate EB of Different Sizes, Culture of EBs within the Same Device and Plating of EBs As described in Example 27, EBs of various sizes (500, 1000 and 2000 cells per EB) were set up from the human embryonic stem cell line H9. EBs were cultured in the microwell device AggreWell™ 400 in mTeSR™ 1-F 270 mOsm/kg for 5 days. To release EBs in order to plate them down, the same methods described in Example 9 were used, with the exception that EBs were not plated onto ultra low adherence plates but instead directly onto 6-well plates coated with Poly-L-ornithine/Laminin (see Example 18). 2 mL of medium was used to wash the EBs from the cell strainer (Falcon) (see Example 9). The 6-well plates were agitated in a backward and forward manner to distribute the EBs evenly across the surface. Plates were placed into an incubator 37° C. with 5% $CO_2$ and 95% humidity for at least 2 days before morphological assessment. Morphological assessment of neural rosettes representing ectoderm was performed as described in Example 12. FIG. 24 shows attached EBs of various sizes (500 cells per EB (A,B), 1000 cells per EB (C,D), 2000 cells per EB (E,F)) 1 day after plating. To a person skilled in the art the neural rosettes are present to an extent of nearly 100% in all attached EBs.

Figure 25:
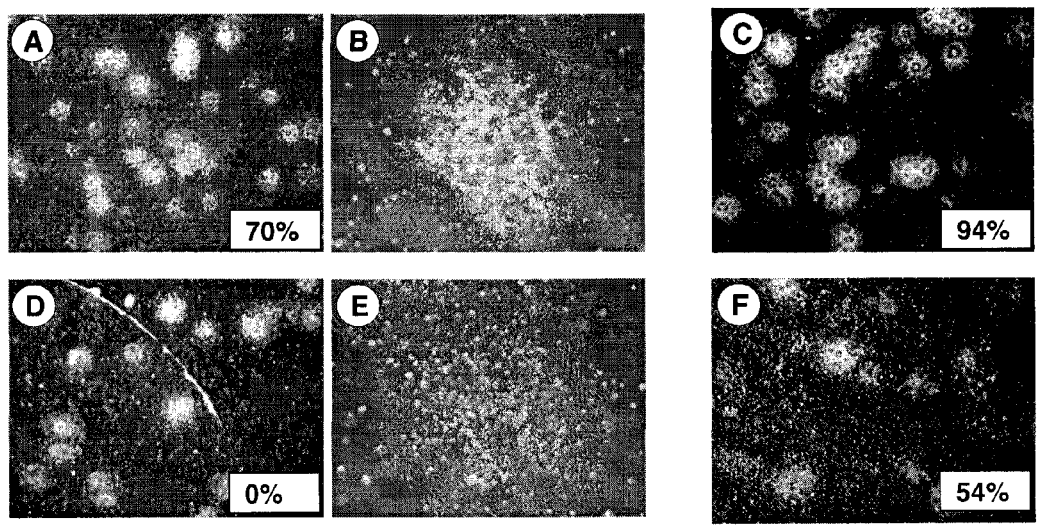
FIG. 25 shows the morphology at day 2 of EBs harvested from the microwell device and plated on poly-L-orthinine/laminin coated plates. The scoring results are indicated as % within the corresponding images. EBs generated in mTeSR™ 1-F 270 mOsm/kg (A, B and C) and EBs generated in mTeSR™ 1-F 340 mOsm/kg (D, E and F). EBs sizes tested were EBs of 2000 cells per EB (C and F) and 500 cells per EB (A, B, D and E). Magnification: 2× (A, C, D, F) and 10× (B,E).

Example 30. Highly Efficient Neural Ectoderm Induction of Human Pluripotent Stem Cells in mTeSR™ 1-F with an Osmolality of 270 mOsm/kg Compared to mTeSR™ 1-F with an Osmolality of 340 mOsm/kg with EB Formation and Continual Culture in a Microwell Device (AggreWell™ 400) and Subsequent Plating of EBs to Induce Ectoderm EBs were formed and cultured in AggreWell™ 400 from human embryonic stem cell line H9 as described in Example 7. Media used in this example were mTeSR™ 1-F with an osmolality of 270 and 340 mOsm/kg. Two different sizes of EBs were set up: 500 cells per EB and 2000 cells per EB. EBs were cultured in the microwell device for 5 days and then plated as described in Example 29. FIG. 25 shows the morphology of plated EBs at day 2 in both media at two different sizes as well as scoring results (colonies with >50% of area containing rosettes). The results indicated that the induction of neural ectoderm from human pluripotent stem cells in mTeSR™ 1-F with an osmolality of 270 mOsm/kg was more efficient than in mTeSR™ 1-F with an osmolality of 340 mOsm/kg.

Example 31. Continual Culture of EBs of Different Sizes within Microwell Device (AggreWell™ 800) in mTeSR™ 1-F with an Osmolality of 270 mOsm/kg for 5 Days to Induce Ectoderm A single cell suspension from the human embryonic stem stem cell line H9 was obtained as described in Example 24. EBs were set up as described in Example 25 with the exception that only mTeSR™ 1-F with an osmolality of 270 mOsm/kg was used. Different sizes of EBs were formed in AggreWell™ 800: 2000 cells, 5000 cells, 10000, 15000 and 20000 cells. Single cell suspension volumes, which were added to the AggreWell™ 800 wells were calculated according to cell counts and the numbers given in Table 3. In this example, instead of harvesting the EBs from the AggreWell™ 800 plate after 24 hours, the EBs were left in the microwells for up to 11 days. Medium was changed every day by removing approximately 1.5 mL of media from an individual AggreWell™ 800 well using a micropipettor outfitted with a disposable 1 mL tip. Pre-warmed (37° C.) fresh mTeSR™ 1-F 270 mOsm/kg medium was dispensed slowly into the well thereby making sure not to disturb the EBs in the microwells.

Figure 26:
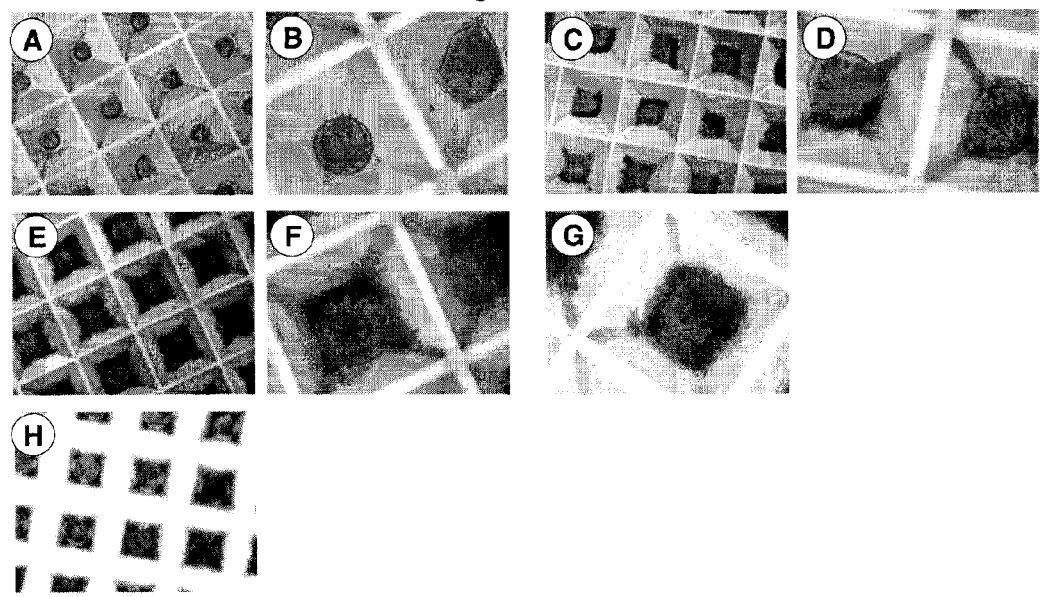
FIG. 26 shows EBs of various sizes inside the microwells of AggreWell™ 800 at day 5 before harvest and plating of the EBs. The following EB sizes are shown: EBs of a size of 2000 cells per EB (A and B), EBs of a size of 5000 cells per EB (C and D), EBs of a size of 10000 cells per EB (E and F), EBs of a size of 15000 cells per EB (G) and EBs of a size of 20000 cells per EB (H). Magnification: 4× (A, C, E, H), 10× (B, D, F, G)
Figure 27:
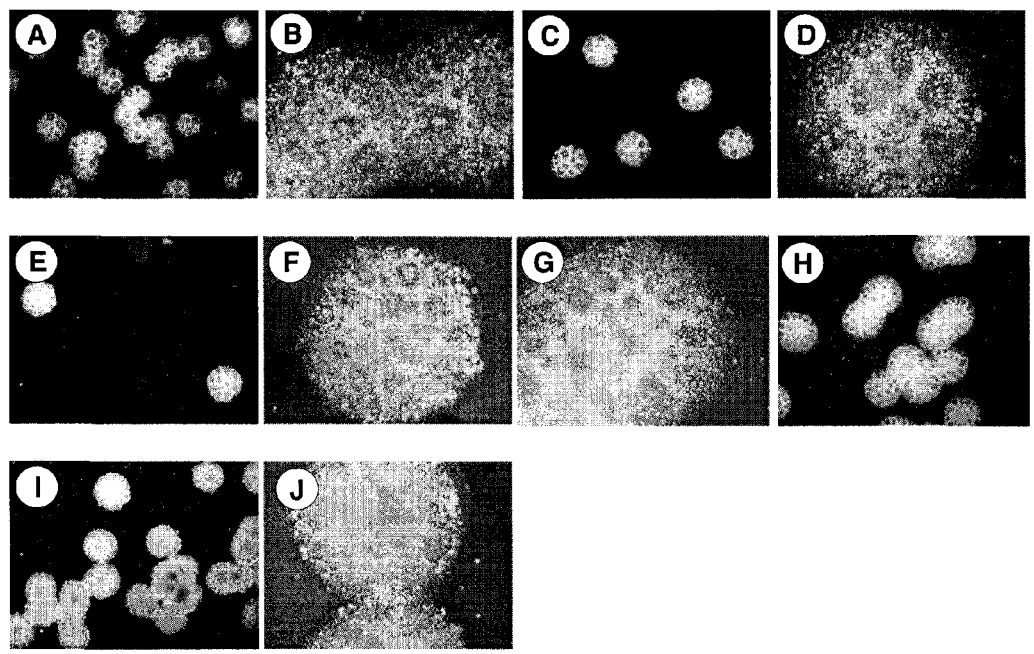
FIG. 27 shows EBs at various sizes harvested from the microwell device and after 1 one day of plating on poly-L-ornithine/laminin plates: The following EB sizes are shown: EBs of a size of 2000 cells per EB (A,B), 5000 cells per EB (C,D), 10000 cells per EB (E,F), 15000 cells per EB (G,H) and 20000 cells per EB (I,J). Magnification: 2× (A, C, E, G, I) and 10× (B, D, F, H, J).

Example 32. Induction of Neural Ectoderm from Human Pluripotent Stem Cells in mTeSR™ 1-F with an Osmolality of 270 mOsm/kg Using a Microwell Device (AggreWell™ 800) for EB Formation and Culture within the Same Device Followed by Plating of the EBs As described in Example 31, EBs of various sizes were set up from the human embryonic stem cell line H9. EBs were cultured in the microwell device AggreWell™ 800 in mTeSR™ 1-F 270 mOsm/kg for 5 days. To release EBs in order to plate them down, the same methods described in Example 27 were used for EBs larger than 3000 cells per EB, with the exception that EBs were not plated onto ultra low adherence plates but instead directly onto 6-well plates coated with Poly-L-ornithine/Laminin (see Example 18). 2 mL of medium was used to wash the EBs from the cell strainer (Falcon). The 6-well plates were agitated in a backward and forward manner to distribute the EBs evenly across the surface. Plates were placed into an incubator 37° C. with 5% $CO_2$ and 95% humidity for at least 2 days before assessing the cultures morphologically. Morphological assessment of neural rosettes representing ectoderm was performed as described in Example 12. FIG. 26 shows attached EBs of various sizes inside the microwells of AggreWell™ 800 at day 5 before releasing and plating the EBs. FIG. 27 shows EBs 1 day after plating. To the experienced eye the neural rosettes are present to an extent of nearly 100% showing that mTeSR™ 1-F 270 mOsm/kg can induce neural ectoderm at very high efficiency in AggreWell™ 800 when using different numbers of human pluripotent stem cells for EB formation as well as continuous culture inside the microwells.

Example 33. Highly Efficient Neural Ectoderm Induction of Human Pluripotent Stem Cells in mTeSR™ 1-F with an Osmolality of 270 mOsm/kg Compared to mTeSR™ 1-F with an Osmolality of 340 mOsm/kg with EB Formation and Culture in a Microwell Device (AggreWell™ 800)

Figure 28:
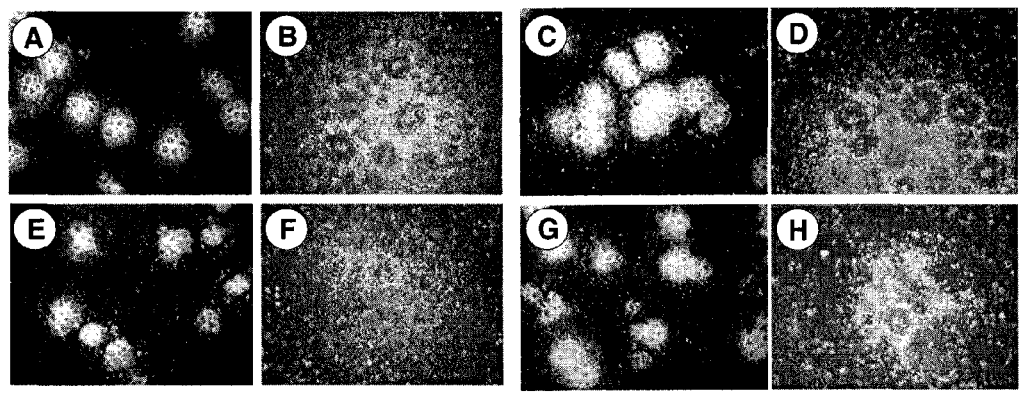
FIG. 28 shows the morphology of EBs generated in mTeSR™ 1-F 270 mOsm/kg (A-D) and mTeSR™ 1-F 340 mOsm/kg (E-H) and plated on poly-D-ornithine/laminin at day 2. The following EB sizes are shown: EBs of a size of 2000 cells per EB (A, B, E, F) and EBs of a size of 5000 cells per EB (C, D, G, H). Magnification: 2× (A, C, E, G) and 10× (B, D, F, H).

EBs were formed and cultured in AggreWell™ 800 from human embryonic stem cell line H9 as described in Example 31. Media used in this example were mTeSR™ 1-F with an osmolality of 270 and 340 mOsm/kg. Two different sizes of EBs were set up: 2000 cells per EB and 5000 cells per EB. EBs were cultured in the microwell device for 5 days and then plated as described in Example 31. FIG. 28 shows the morphology of plated EBs at day 2. The results indicated that the induction of neural ectoderm from human pluripotent stem cells in mTeSR™ 1-F with an osmolality of 270 mOsm/kg was more efficient than in mTeSR™ 1-F with an osmolality of 340 mOsm/kg.

Example 34. Media Formulations with Different Osmolality Ranges: Factor Free mTeSR™ 1 Medium with the Osmolalities 400 mOsm/kg and 450 mOsm/kg The complete media formulation and method of preparation for modified TeSR (mTeSR™ 1, STEMCELL TECHNOLOGIES INC., catalogue #05850) is published in Ludwig et al, Nature Methods 3(8): 637, 2006. It is based on the original TeSR formulation published in Ludwig et al., Nature Biotechnology 24(2): 185, 2006, with the following modification: substitution of human serum albumin (HSA) with bovine serum albumin (BSA).

To manufacture the factor free mTeSR™ 1 (mTeSR™ 1-F) media, a 5× supplement was produced containing all of the mTeSR™ 1 reagents at 5-fold concentrations, with the exceptions of the following 5 factors: GABA, pipecolic acid, bFGF, TGFβ1, lithium chloride. The components for the media are shown in Table 2.

After mixing the components of the 5× supplement together, the pH was adjusted to 7.4 by adding 10N NaOH. The osmolality of the solution was measured using a standard osmometer. The initial osmolality of the 5× supplement was usually around 100 mOsm/kg, and salt (NaCl) was used to increase the osmolality while taking into account that the 5× supplement is combined with 400 mL of the base medium DMEM/F12 (Hyclone, catalog #SH30004) to obtain mTeSR™ 1-F. The amount of salt that had to be added to the 5× supplement was calculated using the following formula: For example to obtain an osmolality of 400 after mixing the 5× supplement and the basal medium:

$$[400-((0.8\times300\ mOsm)+(0.2\times100\ mOsm))]/2000\times 58.44\times1.05=4.3\ g/L\ of\ NaCl$$

The x amount of NaCl was added to the 5× supplement. Two media with different osmolalities were prepared: 400 mOsm/kg and 450 mOsm/kg.

Example 35. Highly Efficient Neural Ectoderm Induction of Human Pluripotent Stem Cells in mTeSR™ 1-F with an Osmolality of 270 mOsm/kg Compared to mTeSR™ 1-F with an Osmolality Range of 320, 340, 400 and 450 mOsm/kg in AggreWell™ 400

Single cell suspensions were obtained from H9 hESCs described in Example 6. EBs were formed in AggreWell™ 400 as described in Example 7. Media used for EB setup were mTeSR™ 1-F with osmolalities of 270 (Example 23), 320, 340 (Example 5), 400 and 450 mOsm/kg (Example 34). Y27632 rock inhibitor was also added to the medium at a final concentration of 10 μg/mL to enhance cell survival during EB formation. EBs with a size of 2000 cells per EB were set up and either taken out after 24 hours (see Example 9) and cultured in suspension culture until plating by trituration (see Example 11) or left in the AggreWell™ plates for 5 days and then plated (see Example 29).

Figures 29, 30:
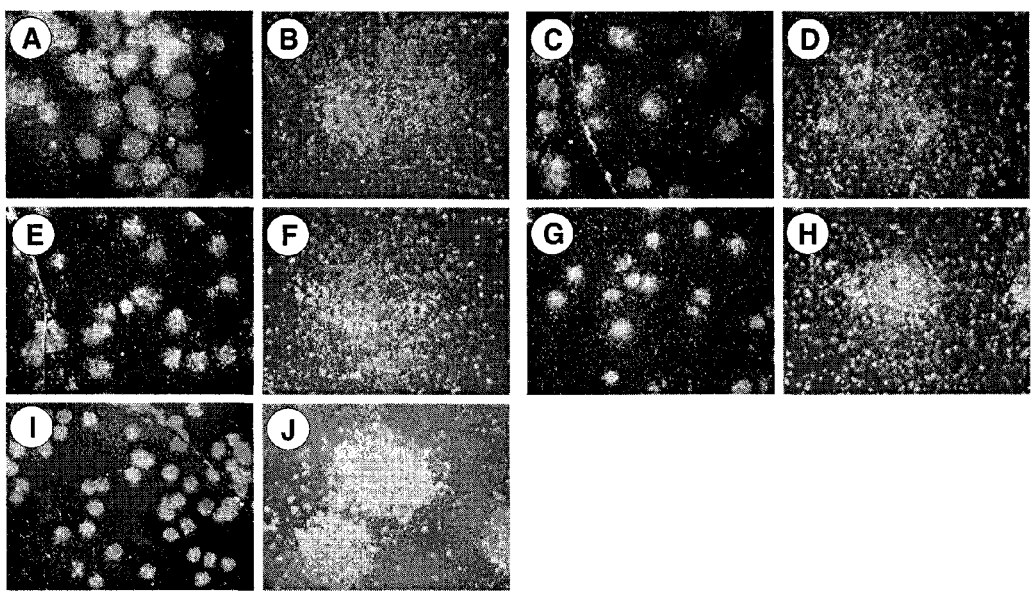
FIG. 29 shows attachment of EBs generated in media with different osmolalities and then plated on poly-L-ornithine/laminin coated plates in the same media after 2 days. Attached EBs which were previously generated in mTeSR™ 1-F 270 mOsm/kg (A,B), mTeSR™ 1-F 320 mOsm/kg (C,D), mTeSR™ 1-F 340 mOsm/kg (E,F), mTeSR™ 1-F 400 mOsm/kg (G,H) and mTeSR™ 1-F 450 mOsm/kg (I,J). Magnifications: left 2× (A, C, E, G, I), and 10× (B, D, F, H, J).
FIG. 30 shows the scoring results for attached EBs generated in media with different osmolalities (mTeSR™ 1-F 270 mOsm/kg; mTeSR™ 1-F 320 mOsm/kg, mTeSR™ 1-F 340 mOsm/kg and mTeSR™ 1-F 400 mOsm/kg) after 2 days. The cultures containing mTeSR™ 1-F 450 mOsm/kg were visually inspected for presence of rosettes on day 1.

FIG. 29 shows EB attachment after 2 days in the different media except in medium mTeSR™ 1-F 450 mOsm/kg. The EBs formed in this medium are shown at day 1. The percentage of rosettes was highest (100%) in medium with the osmolality of 270, with a drop at 320 and 340 and no rosettes formation observed in 400 and 450 mOsm/kg. Note that at an osmolality higher than 340, cell detachment and cell death was observed after plating and no morphologically distinct cell types could be identified. FIG. 30 shows the scoring results of these two experiments. Colonies with >50% of area containing rosettes were counted as well as all colonies. The ratio as well as the resulting percentage of rosette containing colonies is shown. Visual inspection of the 450 mOsm/kg condition on day 1 did not reveal any rosettes.

Example 36. Highly Efficient Neural Ectoderm Induction of Human Pluripotent Stem Cells Maintained as Single Cell Cultures in mTeSR™ 1-F with an Osmolality of 270 mOsm/kg Compared to mTeSR™ 1-F with an Osmolality of 340 mOsm/kg with EB Formation and Culture in a Microwell Device (AggreWell™ 800)

Figure 31:
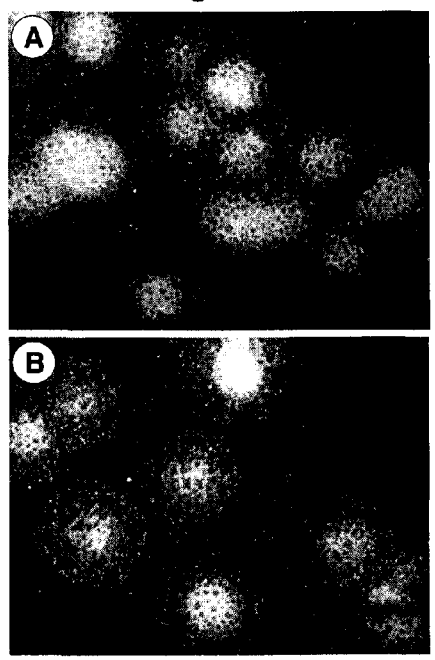
FIG. 31 shows EBs 3 days after attachment. EBs were previously generated from human embryonic stem cell line H9, which had been passaged as single cell suspensions for 4 passages (p51-p55) in mTeSR™ 1-F 270 mOsm/kg (A) or mTeSR™ 1-F 340 mOsm/kg (B). Magnification 2×.

The human embryonic stem cell line H9 was passaged as single cells in culture for 4 passages between passage 51 to passage 55 (p51 to p55) as described in Example 21. Single cell suspensions of H9 obtained at passage 55 as described in Example 24 for EB formation in AggreWell™ 800. EBs were formed and harvested as described in Examples 31 and 32. FIG. 31 shows that neural rosettes are more efficiently formed in mTeSR™ 1-F 270 mOsm/kg (A) compared to mTeSR™ 1-F 340 mOsm/kg (B). This shows that medium with an osmolality of 270 mOsm/kg can efficiently induce neural ectoderm in human pluripotent stem cells cultured either as aggregates or single cells.

Figure 32:
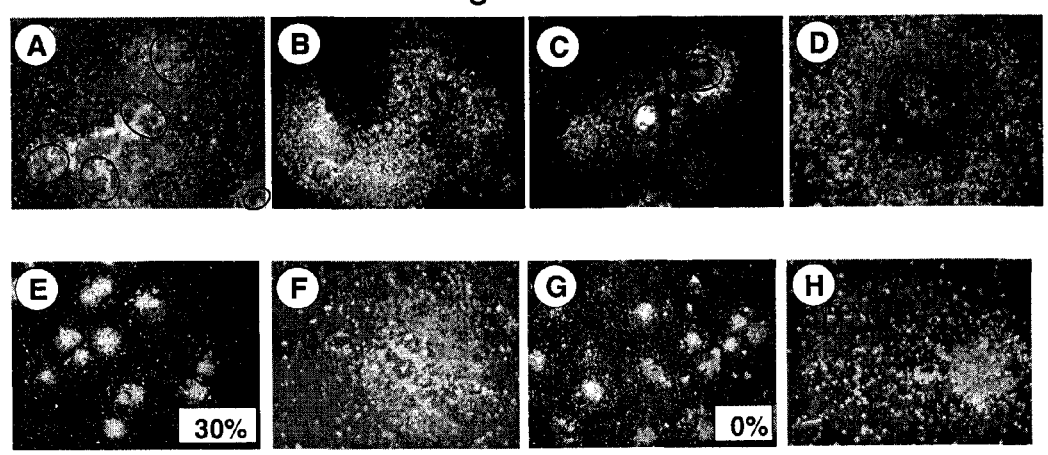
FIG. 32 shows H9 cells at 5 days of passage 52 prior to EB formation (A-D). Circled areas indicate differentiated areas of the colonies at low magnification (A,C) and the same areas at high magnification (B,D). EBs previously formed in mTeSR™ 1-F 270 mOsm/kg are shown here 2 days after attachment on poly-L-ornithine/laminin coated plates (E,F). Scoring results are indicated as % within the corresponding images. EBs previously formed in mTeSR™®1-F 340 mOsm/kg are shown here 2 days after attachment on poly-D-ornithine/laminin coated plates (G,H). Magnifications: 2× (A, C, E, G) and 10× (B, D, F, H).

Example 37. Efficient Induction of Neural Ectoderm Using the Microwell Device (AggreWell™ 800) Containing mTeSR™ 1-F 270 mOsm/kg Compared to mTeSR™ 1-F 340 mOsm/kg from Human Pluripotent Stem Cell Cultures Displaying High Percentages of Differentiation EBs were formed from H9 cell cultures which displayed between 40 and 50% of differentiation. Cells were morphologically accessed for differentiation as described in Example 22. FIG. 32 shows H9 cells at passage 52 (H9p52) at day 5 of culture after passaging and before EB set up (A-D). Differentiated areas are circled. Single cells for EB formation were obtained as described in Example 24 and EBs were formed in AggreWell™ 800 as described in Example 25. EBs were cultured and plated as described in Examples 31 and 32. Morphological assessment of neural rosettes was performed 2 days after plating as described in Example 12. FIG. 32 also shows morphology of EBs at day 2 after plating as well as scoring results (colonies with >50% area containing rosettes) (E-H, EBs set up in mTeSR™ 1-F 270 mOsm/kg (E,F); EBs set up in mTeSR™ 1-F 340 mOsm/kg (G,H). The results indicated that the induction of neural ectoderm from human pluripotent stem cells in mTeSR™ 1-F with an osmolality of 270 mOsm/kg was more efficient than in mTeSR™ 1-F with an osmolality of 340 mOsm/kg even if the percentage of pluripotent cells in the starting population is less than 85%, which is the percentage of colonies containing undifferentiated cells used as a cut-off for all other examples described in this disclosure.

Figure 33:
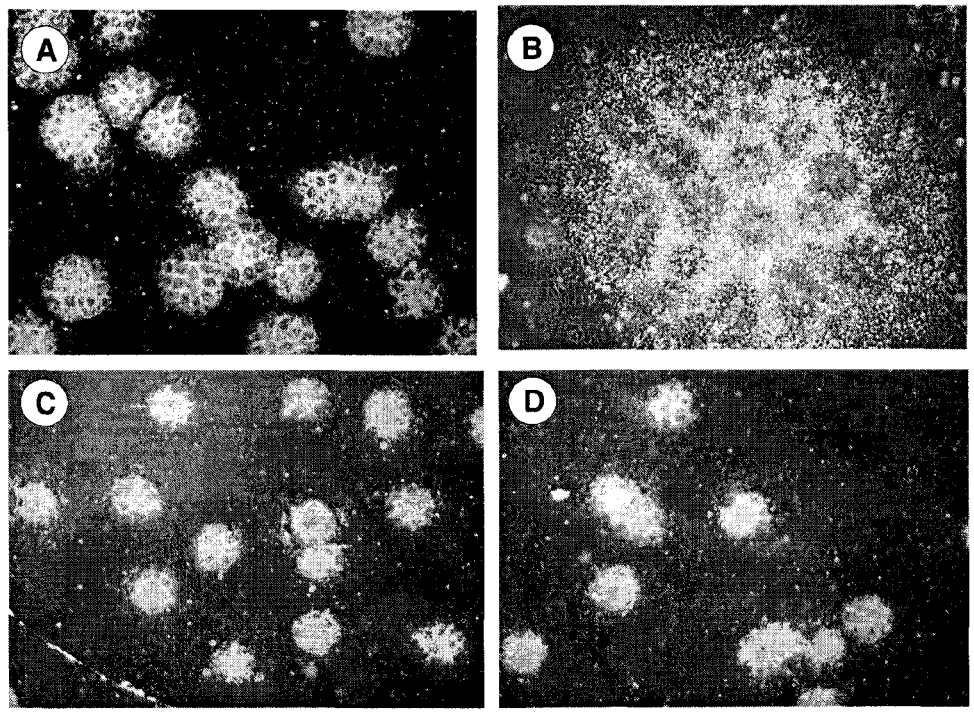
FIG. 33 shows attached EBs generated from hESC line H7 p38 1 day after plating. EBs containing 5000 cells per EB were generated in mTeSR™ 1-F 270 mOsm/kg (A, B) or in mTeSR™ 1-F 340 mOsm/kg (C, D). Magnifications 2× (A, C, D), 10× (B).

Example 38. Efficient Induction of Neural Ectoderm from Human Embryonic Stem Cell Line H7 Using the Microwell Device (AggreWell™ 800) Containing mTeSR™ 1-F 270 mOsm/kg Compared to mTeSR™ 1-F 340 mOsm/kg The hESC line H7 was cultured and passaged as described in Example 20. EBs were formed and cultured from p38 cells in AggreWell™ 800 using mTeSR™ 1-F 270 mOsm/kg or mTeSR™ 1-F 340 mOsm/kg as described in Example 30 with the exception that 5000 cells per EB were used. EBs were released from the microwells and plated as described in Example 31. FIG. 33 shows attached EBs 1 day after they have been plated. Morphological assessment for the presence of neural ectoderm was carried out as described in Example 12. More neural rosettes are present when EBs were formed and cultured in mTeSR™ 1-F 270 mOsm/kg compared to mTeSR™ 1-F 340 mOsm/kg.

Figure 34:
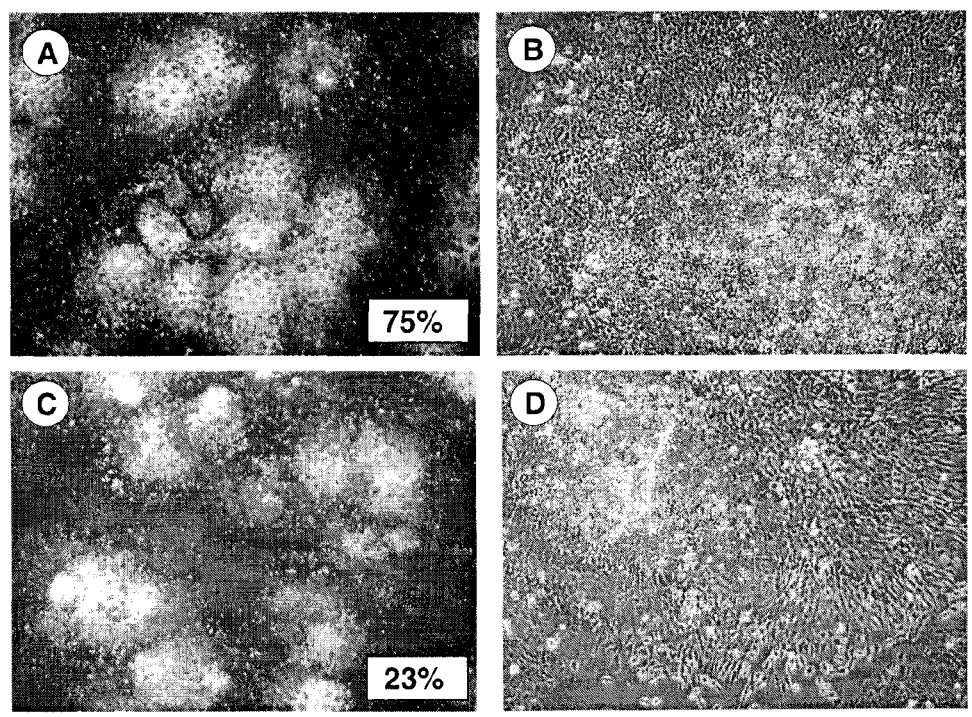
FIG. 34 shows attached EBs generated from hESC line H9 p44 2 days after plating. EBs containing 2000 cells per EB were generated in Knockout™-D-MEM 270 mOsm/kg (A, B) or in Knockout™-D-MEM 340 mOsm/kg (C, D). Scoring results are indicated as "%" within the corresponding images. Magnifications 2× (A, C), 10× (B, D).

Example 39. Efficient Induction of Neural Ectoderm from Human Pluripotent Stem Cell Cultures in Knockout™ D-MEM 270 mOsm/kg Compared to Knockout™ D-MEM 340 mOsm/kg Using the Microwell Device AggreWell™ 400 for Both EB Formation and Culture EBs were formed and cultured in AggreWell™ 400 from human embryonic stem cell line H9 (p44) as described in Example 28. Media used in this example were Knockout™-D-MEM (Invitrogen Cat. No. 10829-018) with an osmolality of either 270 or 340 mOsm/kg adjusted using sodium chloride as described in Examples 5 and 22 (the standard osmolality of Knockout™-D-MEM is approximately 265 mOsm/kg). EBs comprising 2000 cells per EB were formed in Knockout™-D-MEM 270 mOsm/kg and Knockout™-D-MEM 340 mOsm/kg. EBs were cultured in the AggreWell™ 400 for 5 days and then collected and plated as described in Example 29. FIG. 34 shows the morphology of plated EBs at day 2. Morphological assessment of the plated EBs by identification of rosette structures showed that the induction of neural ectoderm from human pluripotent stem cells cultured in Knockout™-D-MEM with an osmolality of 270 mOsm/kg was more efficient compared to Knockout™-D-MEM with an osmolality of 340 mOsm/kg. Scoring for neural rosettes was performed as described in Example 12 at day 6 and the percentages are indicated in FIG. 34. The results indicated that Knockout™-D-MEM with an osmolality of 270 mOsm/kg is more potent at inducing neural rosettes compared to Knockout™-D-MEM with an osmolality of 340 mOsm/kg. Therefore an osmolality of 270 mOsm/kg adjusted even in an alternate media formulation such as Knockout™-D-MEM supported efficient neural ectoderm induction from human pluripotent stem cells.

Figure 35:
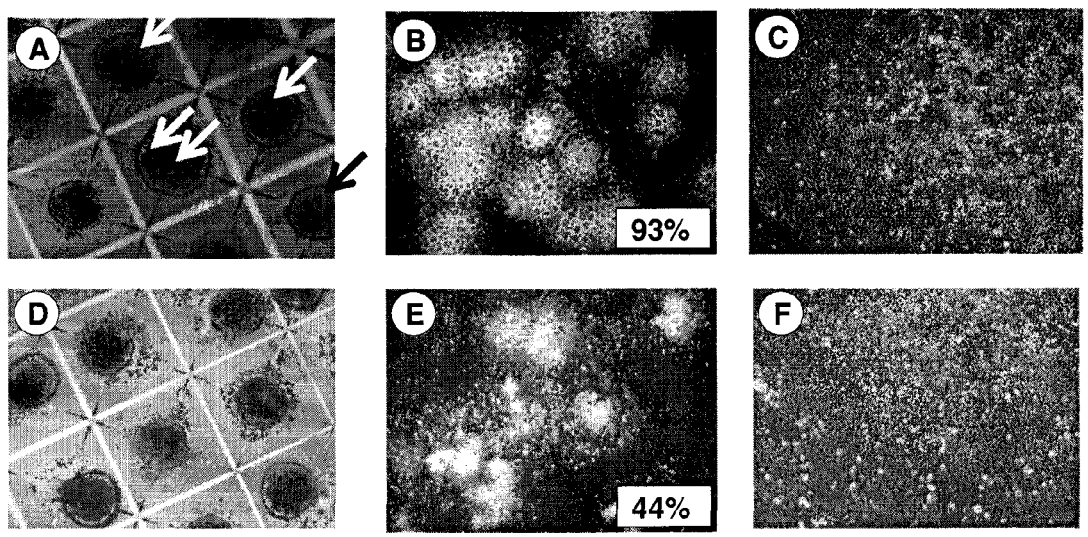
FIG. 35 shows EBs with a size of 2000 cells per EB generated from hESC line H9 p44 at day 5 within the microwells of AggreWell™ 400 just before releasing and plating of the EBs (A, D). B, C, E, F show attached EBs 2 days after plating. EBs were generated in Neurobasal™ 270 mOsm/kg (A, B, C) or in Neurobasal™ 340 mOsm/kg (D, E, F). Scoring results are indicated as "%" within the corresponding images. Magnifications 2× (B, E), 4× (A, D) and 10× (C, F).

Example 40. Efficient Induction of Neural Ectoderm from Human Pluripotent Stem Cell Cultures Cultured in Neurobasal™ Medium at an Osmolality of 270 mOsm/kg Compared to Neurobasal™ Medium at an Osmolality of 340 mOsm/kg Using AggreWell™ 400 for EB Formation and Culture EBs were formed and cultured in AggreWell™ 400 from human embryonic stem cell line H9 (p44) as described in Example 28. The media used in this example were Neurobasal™ medium (Invitrogen Cat. No. 21103049) with an osmolality of 270 or 340 mOsm/kg that was adjusted using sodium chloride as described in Examples 5 and 22 (the standard osmolality of Neurobasal™ medium is approximately 220 mOsm/kg). EBs comprising 2000 cells per EB were set-up in Neurobasal™ medium 270 mOsm/kg and Neurobasal™ medium 340 mOsm/kg. EBs were cultured in the microwell device for 5 days and then plated as described in Example 29. FIG. 35 shows the morphology of EBs inside the microwells of an AggreWell™ 400 plate on day 5 and EBs 2 days after they have been harvested and plated. Inside the microwells as well as in attached EBs, more rosettes are visible in Neurobasal™ medium 270 mOsm/kg than in Neurobasal™ medium 340 mOsm/kg. The results showed that the induction of neural ectoderm from human pluripotent stem cells in Neurobasal™ with an osmolality of 270 mOsm/kg was more efficient than in Neurobasal™ with an osmolality of 340 mOsm/kg. Scoring of rosettes was performed on day 6 after plating as described in Example 12 and reveals higher percentages of neural rosettes for Neurobasal™ with an osmolality of 270 mOsm/kg. Therefore other media formulations with an osmolality of 270 mOsm/kg are also useful to efficiently induce neural ectoderm.

Example 41. Superior Induction of Neural Ectoderm from Human Pluripotent Stem Cells in mTeSR™ 1-F with an Osmolality of 270 mOsm/kg Compared to mTeSR™ 1-F with an Osmolality of 340 mOsm/kg Prepared with 2 Different Lots of Bovine Serum Albumin (BSA)

Figure 36:
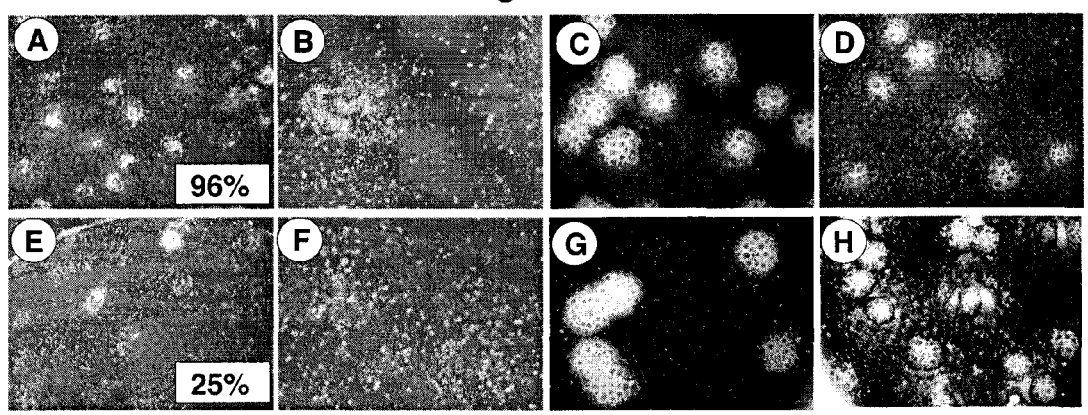
FIG. 36 shows attached EBs containing 500 (A, B, E, F), 2000 (C, D) and 5000 cells per EB (G, H) generated from hESC line H9 p41, p45 and p44 respectively, 3 days after plating. EBs were generated in mTeSR™ 1-F 270 mOsm/kg (BSA lot 2) (C, G), mTeSR™ 1-F 270 mOsm/kg (BSA lot 3) (A, B), mTeSR™ 1-F 340 mOsm/kg (BSA lot 2) (D, H) or in mTeSR™ 1-F 340 mOsm/kg (BSA lot 3) (E, F). Scoring results are indicated as "%" within the corresponding images. Magnification 2×.

Different lots of BSA lots were sourced and used to prepare the media formulations mTeSR™ 1-F 270 mOsm/kg and 340 mOsm/kg for the induction of neural ectoderm. As described in Examples 28 and 30, EBs containing 500, 2000 and 5000 cells per EB were generated from the human embryonic stem cell line H9 (p41, p45 and p44 respectively) using either AggreWell™ 400 or AggreWell™ 800. EBs were cultured in AggreWell™ 400 (500 cells/EB) or AggreWell™ 800 (2000 and 5000 cells/EB) in mTeSR™ 1-F (BSA lot 2 or lot 3) 270 mOsm/kg or mTeSR™ 1-F (BSA lot 2 or lot 3) 340 mOsm/kg for 5 days. EBs were released and plated using the same methods described in Examples 29 and 31. Morphological assessment by identifying neural rosettes was performed as described in Example 12. FIG. 36 shows attached EBs 3 days after plating. To a person skilled in the art it becomes obvious that there are higher quantities of rosettes formed in mTeSR™ 1-F (BSA lot 2 or lot 3) 270 mOsm/kg compared to mTeSR™ 1-F (BSA lot 2 or lot 3) 340 mOsm/kg and with rosettes being more morphologically distinguishable in the low osmolality medium. Furthermore, scoring of attached EBs on day 3 cultured in mTeSR™ 1-F 270 mOsm/kg containing BSA lot 3 reveals a higher percentage of neural rosettes compared to mTeSR™ 1-F 340 mOsm/kg containing BSA lot 3. Therefore media with an osmolality of 270 mOsm/kg induces efficient neural induction and rosette formation.

Figure 37:
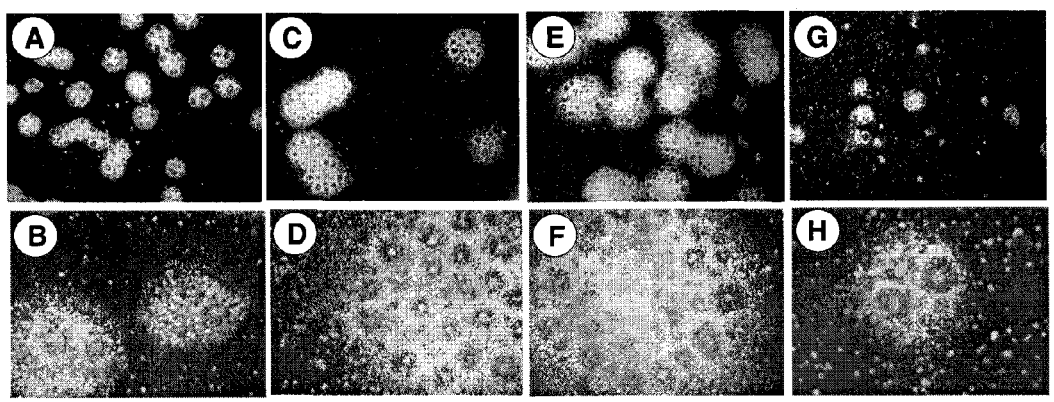
FIG. 37 shows attached EBs containing 2000 (A, B), 5000 (C, D) and 10000 cells per EB (E, F) generated from hESC line H9 p44 and p53, 2 days after plating. G, H show attached EBs containing 2000 cells each generated from the hESC line H1 p59. All EBs were generated in mTeSR™ 1-F 270 mOsm/kg (BSA lot 2). Magnification 2× (A, C, E, G), 10× (B, D, F, H)

Example 42. Efficient and Consistent Induction of Neural Ectoderm from Human Pluripotent Stem Cells in mTeSR™ 1-F with an Osmolality of 270 mOsm/kg Containing BSA Lot 2 Using Either AggreWell™ 400 or 800 to Generate and Culture EBs of Various Sizes As described in Example 30, EBs of different sizes (2000, 5000 and 10000 cells/EB) were formed in AggreWell™ 800 from the human embryonic stem cell line H9 (p44 and p53). Also EBs containing 2000 cells were formed in AggreWell™ 400 from human ESC line H1p59 as described in Example 28. EBs were cultured for 5 days in these AggreWell™ microwell devices in mTeSR™ 1-F (containing BSA lot 2) with an osmolality of 270 mOsm/kg. EBs were released for subsequent plating according to methods described in Examples 29 and 31. Morphological assessment by presence of neural rosettes representing ectoderm was performed as described in Example 12. Virtually 100% of rosettes were present in attached EB cultures. FIG. 37 shows attached EBs of different sizes 2 days after plating. These results clearly indicated that the induction of neural ectoderm in EBs that are formed and cultured in either AggreWell™ 800 or AggreWell™ 400 containing mTeSR™ 1-F with an osmolality of 270 mOsm/kg containing BSA lot 2 is highly efficient and consistent (n=20 experiments).

Figure 38:
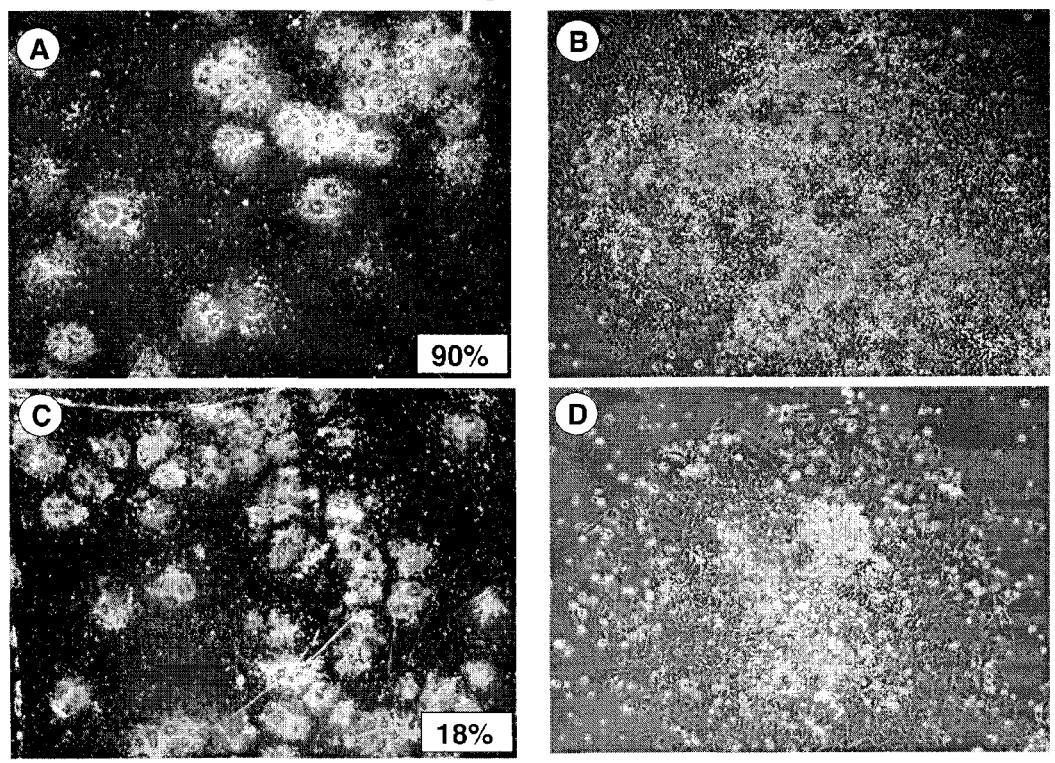
FIG. 38 shows attached EBs generated from hESC line H9 p52 2 days after plating. EBs containing 2000 cells per EB were generated in mTeSR™ 1-F 270 mOsm/kg (A, B) or in mTeSR™ 1-F 340 mOsm/kg (C, D). Scoring results are indicated as "%" within the corresponding images. Magnification 2× (A, C), 10× (B, D)

Example 43. Greater Efficiency in Induction of Neural Ectoderm from Human Pluripotent Stem Cells Cultured in TeSR™ 2 Using mTeSR™ 1-F 270 mOsm/Kg Compared to mTeSR™ 1-F 340 mOsm/Kg with Use of AggreWell™ 400 to Generate and Culture EBs As described in Example 28, EBs containing 2000 cells per EB were formed in AggreWell™ 400 from the human embryonic stem cell line H9 (p52) previously cultured and maintained in TeSR™ 2 (STEMCELL TECHNOLOGIES INC. catalog number 05860). EBs were formed in AggreWell™ 400 containing mTeSR™ 1-F with an osmolality of 270 mOsm/kg or 340 mOsm/kg and cultured for 5 days within the microwells. The method to release EBs and plate EBs is as in Example 29. Morphological assessment by presence of neural rosettes representing ectoderm was performed as described in Example 12. FIG. 38 shows attached EBs 2 days after attachment. Cells cultured in the medium with lower osmolality (270 mOsm/kg) produced more rosettes than cells cultured in the medium with high osmolality (340 mOsm/kg). Neural rosettes were also scored at day 2 and percentages are given in FIG. 38. EBs plated in medium with an osmolality of 270 mOsm/kg contained 90% rosettes compared to 18% rosettes in EBs plated in medium with osmolality of 340 mOsm/kg.

Figure 39:
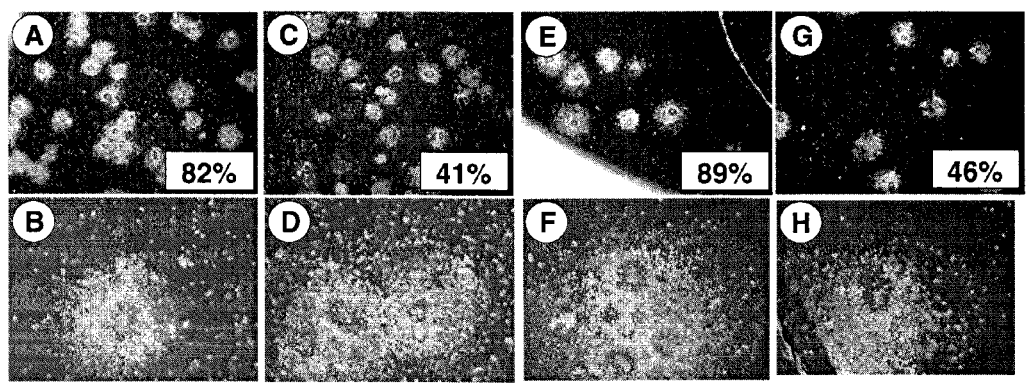
FIG. 39 shows attached EBs generated from hESC line H9 p64 2 days after plating. EBs containing 2000 cells per EB were generated in mTeSR™ 1-F 270 mOsm/kg (BSA lot 2) (A, B, E, F) or in mTeSR™ 1-F 340 mOsm/kg (C, D, G, H) using either AggreWell™ 400 (A-D) or AggreWell™ 800 (E-H). Scoring results are indicated as "%" within the corresponding images. Magnification 2× (A, C, E, G), 10× (B, D, F, H).

Example 44. Induction of Neural Ectoderm from TeSR™ 2 Cultured Human Pluripotent Stem Cells in mTeSR™ 1-F with an Osmolality of 270 mOsm/kg Compared to mTeSR™ 1-F with an Osmolality of 340 mOsm/kg (Both Media Containing BSA Lot 2) Using AggreWell™ 400 and AggreWell™ 800 to Generate and Culture EBs In this example, the human embryonic stem cell line H9 (p64) which had been previously cultured and maintained in TeSR™ 2 (STEMCELL TECHNOLOGIES INC. catalog number 05860) was used to generate EBs. EBs containing 2000 cells per EB were formed in AggreWell™ 400 in mTeSR™ 1-F (BSA lot 2) with an osmolality of 270 mOsm/kg or mTeSR™ 1-F (BSA lot 2) 340 mOsm/kg and cultured in the device for 5 days as described in Example 28. EBs with a size of 2000 cells per EB were also formed in AggreWell™ 800 EBs in both media described above and cultured in the device for 5 days as described in Example 30. The method to release and plate EBs is as described in Examples 29 and 31. Morphological assessment by presence of neural rosettes representing ectoderm was performed as described in Example 12. FIG. 39 shows attached EBs after they were released from either AggreWell™ 400 or AggreWell™ 800 and plated for 2 days. EBs were also scored for neural rosettes at day 2 and percentages are given in FIG. 39. EBs formed in the 270 mOsm/kg medium in either AggreWell™ 400 or AggreWell™ 800 contained rosettes in a range of 82-89%, EBs formed in 340 mOsm/kg medium in either AggreWell™ 400 or AggreWell™ 800 contained rosettes in a range of 41-46%. The results confirmed that osmolality of 270 mOsm/kg efficiently supports neural ectoderm induction.

Figure 40:
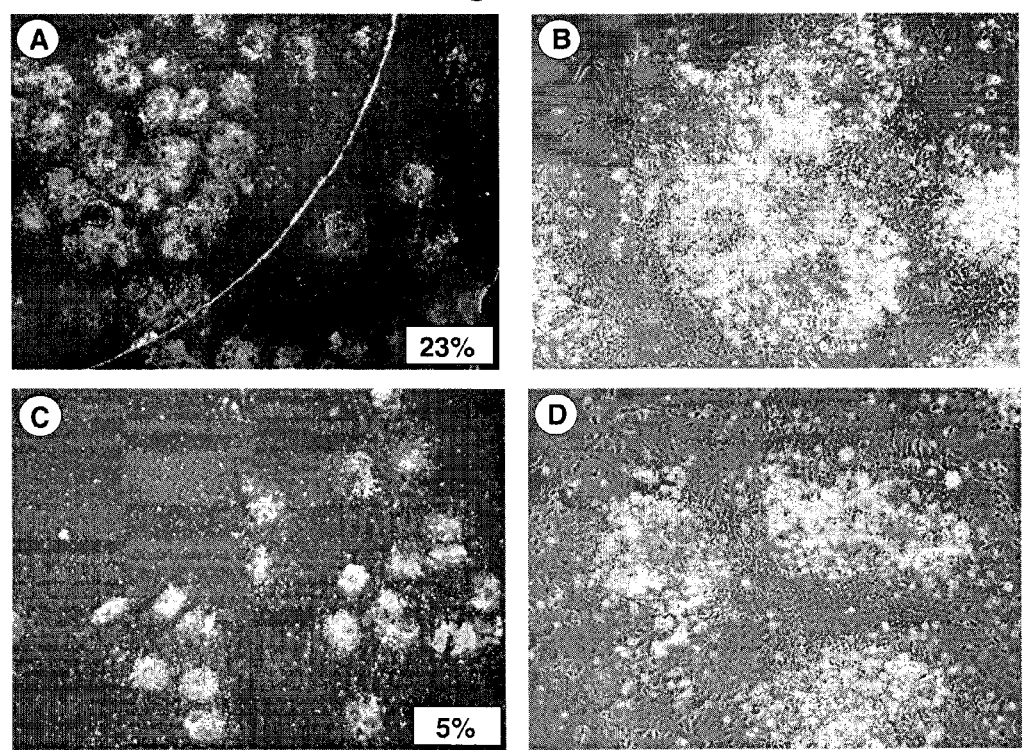
FIG. 40 shows attached EBs containing 2000 cells per EB generated from hESC line H9 p52 2 days after plating. EBs were generated in TeSR™ 2-F 270 mOsm/kg (containing HSA) (A, B) or in TeSR™ 2-F 340 mOsm/kg (containing HSA) (C, D). Scoring results are indicated as "%" within the corresponding images. Magnification 2× (A, C), 10× (B,D).

Example 45. Highly Efficient Induction of Neural Ectoderm from TeSR™ 2 Cultured Human Pluripotent Stem Cells Using AggreWell™ 400 to Generate and Culture EBs in TeSR™ 2-F (Containing HSA) with an Osmolality of 270 mOsm/kg Compared to TeSR™ 2-F (Containing HSA) with an Osmolality of 340 mOsm/kg In this example, the human embryonic stem cell line H9 (p52) which had been previously cultured and maintained in TeSR™ 2 (STEMCELL TECHNOLOGIES INC. catalog number 05860) was used to form EBs. EBs containing 2000 cells per EB were formed in AggreWell™ 400 in TeSR™ 2-F (containing HSA) with an osmolality of 270 mOsm/kg or 340 mOsm/kg and cultured in the microwells for 5 days as described in Example 28. The method to release and plate EBs is described in Example 29. Morphological assessment by presence of neural rosettes representing ectoderm was performed as described in Example 12. FIG. 40 shows attached EBs 2 days after attachment. The lower osmolality medium (TeSR™ 2-F (containing HSA) 270 mOsm/kg)

contains more rosettes than the high osmolality medium (TeSR™ 2-F (containing HSA) 340 mOsm/kg). EBs were also scored at day 2 and percentages are given in FIG. 40. EBs set up in the lower osmolality (270 mOsm/kg) medium contain 23% rosettes, EBs set up in the higher osmolality (340 mOsm/kg) contain 5% rosettes.

In summary, the results showed that human pluripotent stem cells previously cultured and maintained in animal protein free medium (containing HSA) can also give rise to neural rosettes when cultured in mTeSR™ 1-F with an osmolality of 270 mOsm/kg or in TeSR™ 2-F with an osmolality of 270 mOsm/kg).

Figure 41:
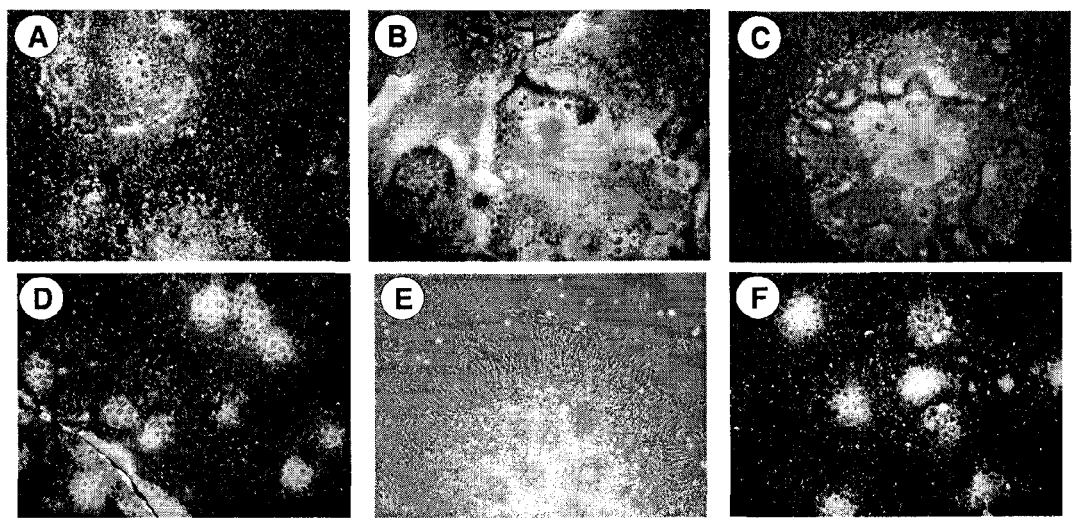
FIG. 41 shows attached EBs generated from hESC line H9 p52 6 days after culture in suspension culture (ULA dishes) followed by plating on coated dishes. EBs were generated in mTeSR™ 1-F 270 mOsm/kg (A), mTeSR™ 1-F 270 mOsm/kg supplemented with 20 ng/mL bFGF (B) or mTeSR™ 1-F 270 mOsm/kg supplemented with 20 ng/mL bFGF, 1% B27 and 1% N2A (C). D-F show attached EBs at 4 days after plating. These EBs were cultured in AggreWell™ 800 plates for 5 days prior to plating in either mTeSR™ 1-F 270 mOsm/kg supplemented with 1% N2A (D), mTeSR™ 1-F 270 mOsm/kg supplemented with 100 ng/mL FGF8 and 200 ng/mL SHH (E) or mTeSR™ 1-F 270 mOsm/kg supplemented with 1% B27 (F). Magnification 2× (A, B, C, D, F), 10× (E).

Example 46. Assessment of Induction of Neural Ectoderm in mTeSR™ 1-F Osmolality 270 mOsm/kg Compared to mTeSR™ 1-F Osmolality 340 mOsm/kg Containing Additional Supplements EBs were formed from the hESC line H9 in AggreWell™ 400 or AggreWell™ 800 plates in mTeSR™ 1-F osmolality 270 mOsm/kg using protocols described in Example 9 and released after 24 hours as described in Example 11. Alternatively, they were formed and cultured inside the microwells of an AggreWell™ 800 plate in mTeSR™ 1-F with an osmolality 270 mOsm/kg as described in Example 30 and released as described in Example 31. Supplements were added to the medium during EB formation in the initial 24 hours of formation as well as to the ULA culture for 5 days or were added to the media changes when cells were cultured inside the microwells of an AggreWell™ 800 plate for 5 days. FIG. 41 shows EBs from ULA culture 6 days after they have been attached, formed and cultured in mTeSR™ 1-F with an osmolality 270 mOsm/kg and 20 ng/ml bFGF or 20 ng/ml bFGF and 1% B27 (Invitrogen, catalog number 0080085SA), 1% N2A (STEMCELL TECHNOLOGIES INC. catalog number 07152). The same figure shows EBs 4 days after attachment formed in mTeSR™ 1-F osmolality 270 mOsm/kg and cultured within the AggreWell™ 800 microwells for 5 days supplemented with 1% N2A, 100 ng/ml Fgf8/200 ng/ml shh or 1% B27. Other supplements used in this experiment (data not shown) were 2% and 5% BSA, 1% non essential amino acids (NEAA) (Invitrogen catalog number 11140050), Fgf8 (100 ng/ml) and shh (200 ng/ml) or 300 ng/ml Noggin (STEMCELL TECHNOLOGIES INC. catalog number 02525). Additional supplements include but are not limited to: SM1 (STEMCELL TECHNOLOGIES INC. Catalog number 05711), ascorbic acid, retinoic acid, cAMP, BDNF, forskolin, NeuroCult® Proliferation Supplements (STEMCELL TECHNOLOGIES INC. catalog number 05701), N2B (STEMCELL TECHNOLOGIES INC. catalog number 07156), Insulin-Transferin-Selenium (ITS) and other additives appropriate for neural progenitor cell expansion and differentiation.

Figure 42:
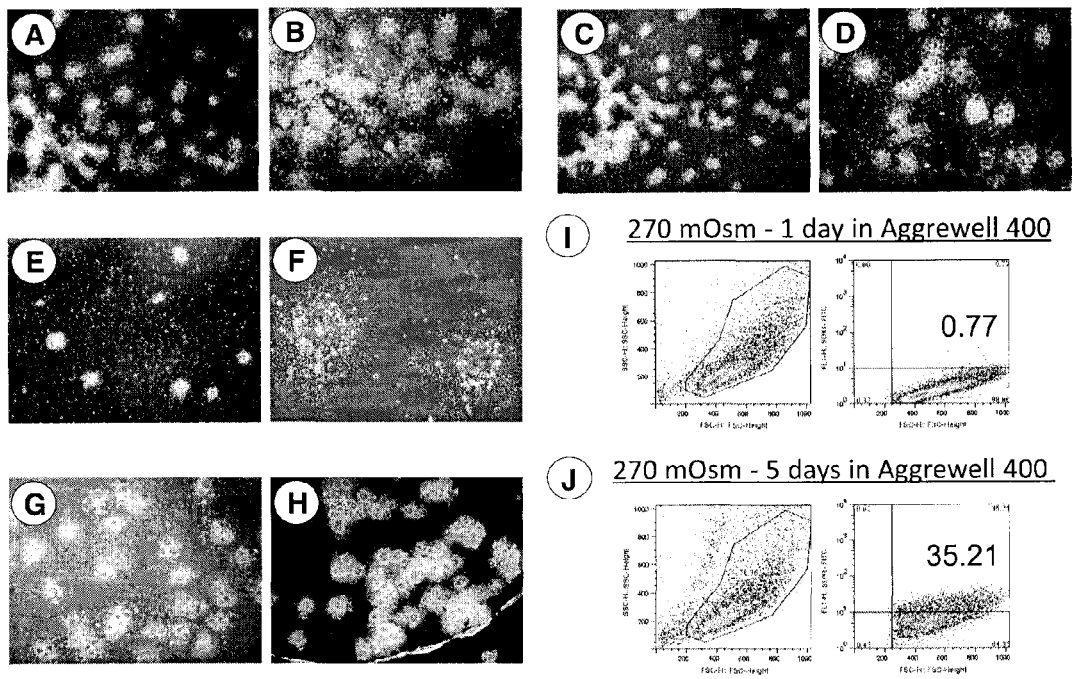
FIG. 42 shows attached EBs generated from hESC line H9 p36 and p42 at different days after plating. EBs containing 2000 cells per EB were generated in mTeSR™ 1-F 270 mOsm/kg. EBs shown in (A) were plated at day 1 after EB formation and are shown at day 3 after plating (a total of 4 days in culture). EBs shown in (B) were plated at day 1 after EB formation and are shown at day 5 after plating (a total of 6 days in culture). EBs shown in (C) were plated at day 2 after EB formation and are shown at day 1 after plating (a total of 3 days in culture). EBs shown in (D) were plated at day 2 after EB formation and are shown at day 5 after plating (a total of 7 days in culture). EBs shown in (E, F) were plated at day 3 after EB formation and are shown at day 3 after plating (a total of 6 days in culture). EBs shown in (G) were plated at day 4 after EB formation and are shown at day 2 after plating (a total of 6 days in culture). EBs shown in (H) were plated at day 5 after EB formation and are shown at day 2 after plating (a total of 7 days in culture). (I) shows a FACS plot of attached EBs plated at day 1 (0.77% positive cells) stained with antibodies for the neural marker Sox1. (J) shows a FACS plot of Sox1 positive cells of EBs plated at day 5 (35.21% positive cells; the left plots in both (I and J) represent the gating for live cells). Magnification 2× (A-E, G, H), 10× (F).
Figure 43:
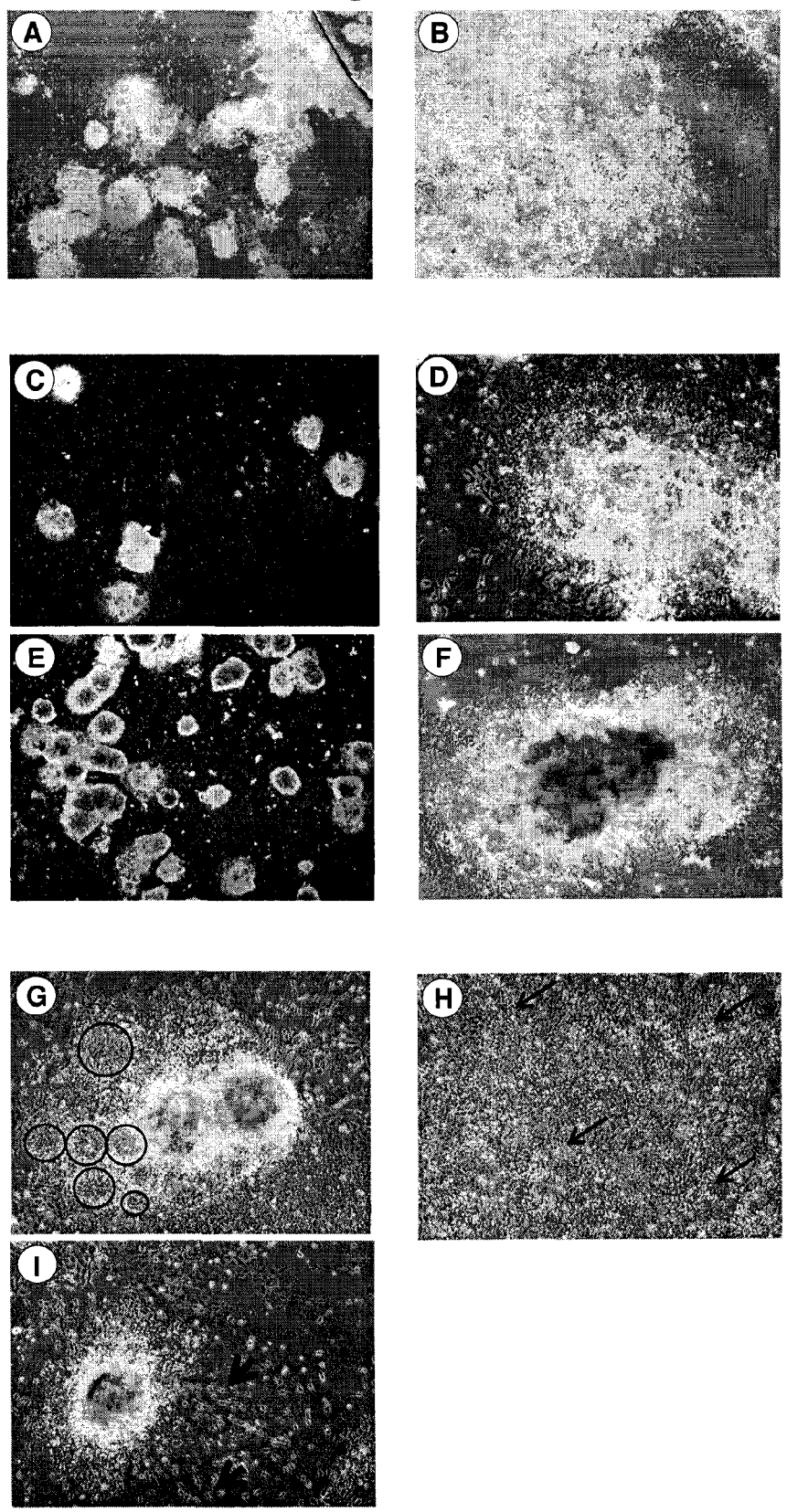
FIG. 43 shows attached EBs generated from hESC line H9 p36 and p42 at different days after plating. EBs containing 2000 cells per EB were generated in mTeSR™ 1-F 270 mOsm/kg. EBs shown in (A, B) were plated at day 7 after EB formation and are shown at day 2 after plating (a total of 9 days in culture). EBs shown in (C, D) were plated at day 8 after EB formation and are shown at day 2 after plating (a total of 10 days in culture). EBs shown in (E, F) were plated at day 11 after EB formation and are shown at day 2 after plating (a total of 13 days in culture). EBs shown in (G, H, I) were plated at day 11 after EB formation and are shown at day 5 after plating (a total of 16 days in culture). Circles in (G) mark rosettes structures, thin arrows in (H) mark neural progenitor cells and thick arrows in (I) mark mature neurons. Magnification 2× (A, C, E), 10× (B, D, F, G, H, I).

Example 47. Efficient Induction of Neural Ectoderm in EBs Generated in mTeSR™ 1-F Osmolality 270 mOsm/Kg Using AggreWell™ 800 and Plated at Different Time Points As described in Example 30, EBs containing 2000 cells/EB were formed in AggreWell™ 800 from the human embryonic stem cell line H9 (p36 and p42). EBs were cultured in these AggreWell™ microwell devices in mTeSR™ 1-F with an osmolality of 270 mOsm/kg. EBs were released for subsequent plating according to methods described in Example 31 with the exception that EBs were harvested from the microwells at different time points (day 2, 3, 4, 5, 7, 8, 9 and 11). Morphological assessment by presence of neural rosettes representing ectoderm was performed as described in Example 12. FIGS. 42 and 43 show attached EBs released and plated at different time points, 1 to 5 days after plating. The attached EBs show a high content of neural rosettes when plated as early as day 1 after initial formation in AggreWell™ 800 3 days after plating (in total 4 days) or plated at day 2 and 1 day after plating (in total 3 days of induction in mTeSR™ 1-F 270 mOsm/kg). A mixture of rosettes of various sizes (circle in FIG. 43), single cell layer neural progenitor cells (thin arrow in FIG. 43) and mature neurons (thick arrow in FIG. 43) can be still identified in EBs plated as late as day 11 and analyzed 5 days after plating (in total 16 days after EB formation). This example shows that neural rosettes are induced as early as within 2 days in the AggreWell™ 800 plates and become obvious as early as 1 day after plating. When EBs are kept in the AggreWell™ 800 plates for 24 hours and are plated afterwards, then the plated EBs show rosettes within 3 days after plating of the EBs. EBs cultured in AggreWell™ 800 for up to 11 days, harvested and then cultured for 5 days (for a total of 16 days of culture in mTeSR™ 1-F 270 mOsm/kg), generated rosettes which contained neural cells with morphologies indicative of different stages of commitment to the neural fate (i. e. early neural progenitor cells were present in rosettes, single cell neural progenitor cells with bipolar morphology growing out from the rosettes and neurons with axonal projections) which can be identified by a person skilled in the art. Experiments were also performed for culturing EBs in the AggreWell™ 800 device containing mTeSR™ 1-F 270 mOsm/kg for a total of 6, 7, 9, 10 and 12 days. Furthermore, attached EB cultures were analyzed by flow cytometry analyses to determine the percentage of Sox1 positive neural progenitor cells (NPCs) in attached EBs plated after 1 or 5 days of culture within the AggreWell™ 800 microwells. The FACS plot in FIG. 42 shows that 35.21% of Sox1 positive cells were detected in attached EBs at 5 days compared to 0.77% Sox1 positive in EBs attached for 1 day.

Figure 44:
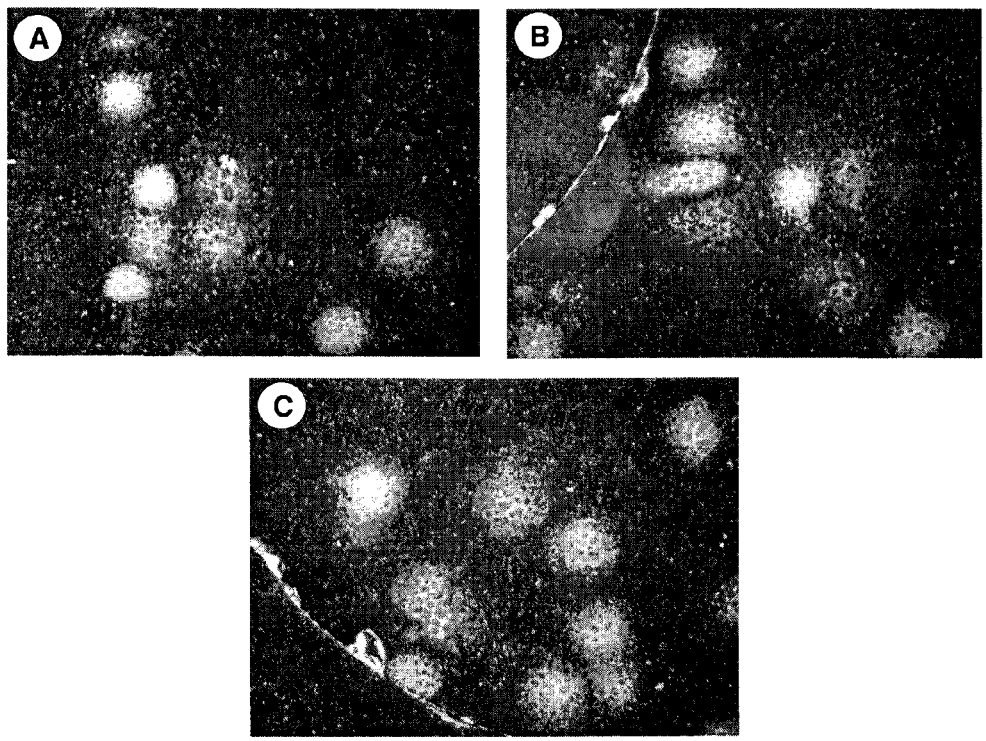
FIG. 44 shows attached EBs generated from hESC line H9 p38 3 days after plating on different surfaces. EBs containing 2000 cells per EB were generated in mTeSR™ 1-F 270 mOsm/kg. (A) shows EBs that were plated on dishes coated with Poly-L-ornithine and 1 μg/mL of laminin. (B) shows EBs that were plated on dishes coated with Poly-L-ornithine and 10 μg/mL of laminin. (C) shows EBs that were plated on dishes coated with Poly-L-ornithine and 20 μg/mL of laminin. Magnification 2×.

Example 48. Efficient Neural Ectoderm Induction in EBs Formed and Cultured in mTeSR™ 1-F with an Osmolality of 270 mOsm/kg in AggreWell™ and Plated onto Different Surfaces EBs which contained 2000 cells per EB were formed from hESC line H9 p38 in AggreWell™ 800 as described in Example 30. EBs were released from AggreWell™ and plated onto Poly-L-ornithine/Laminin coated dishes as described in Example 31. Plates were coated as described in Example 18 with the exception that various concentrations of laminin were used: 1, 10 and 20 µg/mL. FIG. 44 shows EBs 3 days after attachment. 100% neural rosette formation is present in all conditions. Therefore, different concentrations of laminin allowed EB attachment at comparable efficiency.

Figure 45:
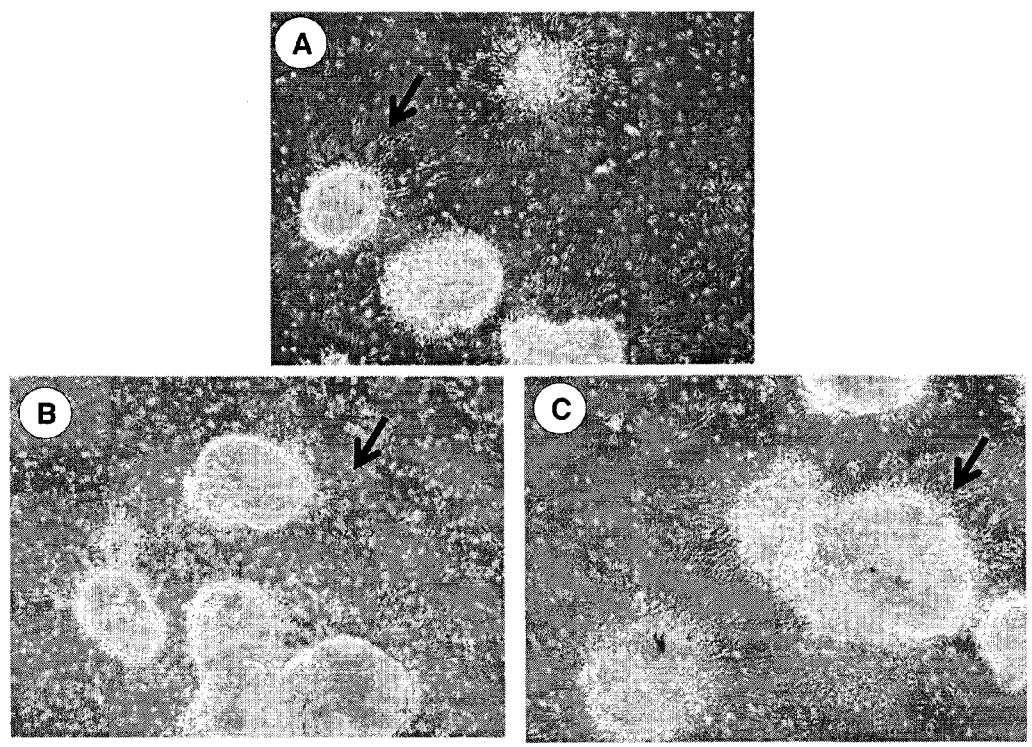
FIG. 45 shows neurospheres at day 1 after suspension culture for 5 days in ultra low adherence (ULA) dishes plates. Neurospheres were generated from attached EBs initially formed in mTeSR™ 1-F with an osmolality of 270 mOsm/kg alone (A) or in mTeSR™ 1-F with an osmolality of 270 mOsm/kg supplemented with 1% B27 (B) or in mTeSR™ 1-F with an osmolality of 270 mOsm/kg supplemented with 1% N2A (C). Arrows point towards neurons growing out and extending axons from the attached neurosphere.
Figure 46:
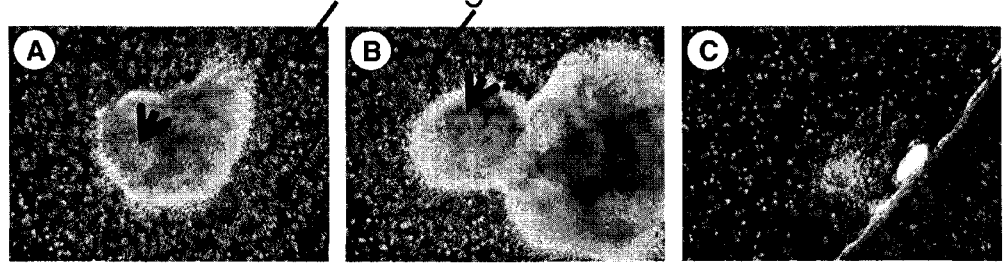
FIG. 46 shows attached EBs at day 6 after plating. EBs were formed in mTeSR™ 1-F with an osmolality of 260 mOsm/kg (A-C) or mTeSR™ 1-F with an osmolality of 270 mOsm/kg (D-F) and were cultured for 13 days inside AggreWell™ 800. Neural rosettes are indicated with thick arrows and neurons with thin arrows in A-F. Magnification 10× (A, B, C, E, F), 4× (D).
Figure 46:
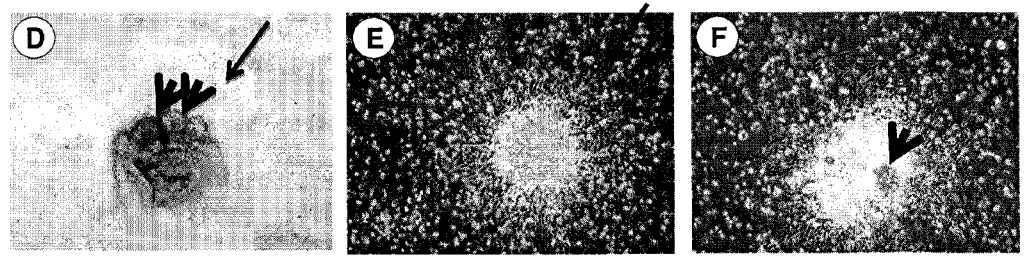

Example 49. Culture of EBs Previously Formed in mTeSR™ 1-F with an Osmolality of 260 mOsm/kg or 270 mOsm/kg in Subsequent Neurosphere Suspension Cultures Leads to Highly Efficient Induction of Neural Rosettes and Neuronal Outgrowth after Plating EBs were formed from H9 p51 hESCs in mTeSR™ 1-F with an osmolality of 260 mOsm/kg or 270 mOsm/kg in AggreWell™ 400 according to Example 9 and EBs were released from the microwells according to Example 11. As described in Example 51, attached EBs were dissociated with 1 mg/ml Dispase and re-plated. The next day many clumps of cells were present which had rounded up into aggregates or "neurospheres". These neurospheres were transferred into Ultra Low Adherent (ULA) plates using a serological 5-mL pipette and cultured in the same medium they were previously cultured in (i. e. mTeSR™ 1-F with an osmolality of 260 mOsm/kg or 270 mOsm/kg) for 5 days. Neurospheres were then collected and plated onto Poly-L-ornithine/Laminin coated dishes (see Example 18). FIG. 45 shows neurospheres at day 1 after plating showing attached neurospheres formed in mTeSR™ 1-F with an osmolality of 270 mOsm/kg alone or containing 1% B27 (Invitrogen, catalog number 0080085SA) and/or 1% N2A (STEMCELL TECHNOLOGIES INC. catalog number 07152). Neurons (arrows), which extended projections, were observed in all 3 media. Other supplements (as described in Example 46) have also been used for the neurosphere culture medium. Alternatively, EBs kept in ULA culture in mTeSR™ 1-F with an osmolality of 260 mOsm/kg or 270 mOsm/kg for 13 days, harvested and plated for 6 days generated neural rosettes (thick arrows) and neurons (thin arrows) as shown in FIG. 46.

This example shows that culture of EBs formed in low osmolality media: mTeSR™ 1-F with an osmolality of 260 mOsm/kg or 270 mOsm/kg as neurospheres (after an initial passage and then transferred to ULA dishes) or culture of EBs for extended culture periods in ULA dishes leads to neuronal populations including rosettes and neurons.

Figure 47:
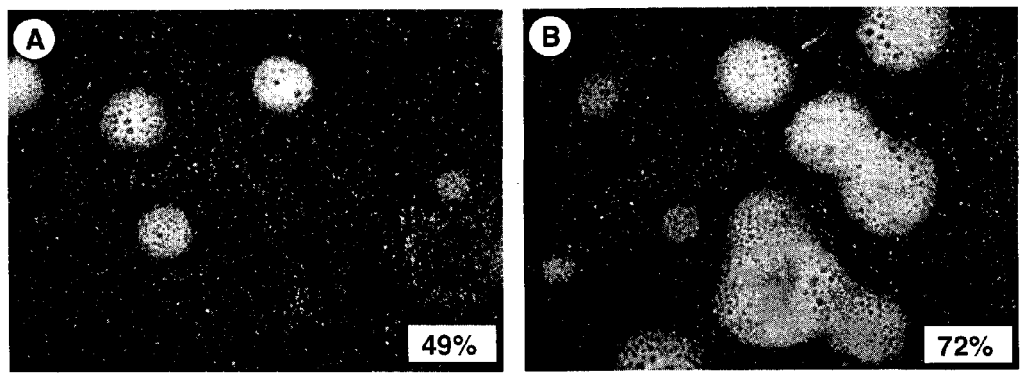
FIG. 47 shows attached EBs generated from hESC line H9 p47 4 days after plating. hESCs were either cultured in hESC maintenance medium until EB formation (A) or were pre-conditioned for 24 hours in mTeSR™ 1-F 320 mOsm/kg (B). Then, EBs were generated in mTeSR™ 1-F 270 mOsm/kg and cultured in suspension culture (ULA dishes) for 5 days after which they were allowed to attach. Scoring results are indicated as "%" within the corresponding images. Magnification 2×.

Example 50. Pre-Conditioning of hPSC Cultures with mTeSR™ 1-F with an Osmolality of 270 mOsm/kg Prior to EB Formation in a Microwell Device Increase Efficiency of Neural Induction in mTeSR™ 1-F with an Osmolality of 320 mOsm In this example hPSC lines were cultured in mTeSR® as described. Here, the hESC line H9 at passage 47 was used. Prior to EB formation the culture medium was changed to mTeSR™ 1-F with an osmolality of 320 mOsm/kg and cells were cultured for 24 hours. This step was performed to increase the efficiency of neural ectoderm formation particularly in the protocol described in Example 9. All EBs were formed in mTeSR™ 1-F with an osmolality of 270 mOsm/kg. Neural induction is assessed by neural rosette formation as described in example 12. EBs were formed from pre-conditioned H9 cells in AggreWell™ 400 as described in Example 9 and were released after 24 hours to be cultured in ULA plates for 5 days (as described in Example 11). FIG. 47 shows EBs 4 days after they were plated and allowed to attach onto Poly-L-ornithine/Laminin. Neural rosette percentages increased from 49% in non-conditioned medium (mTeSR™ 1) (left picture) to 72% when hESCs were pre-conditioned in mTeSR™ 1-F with an osmolality of 320 mOsm/kg (right picture).

Example 51. Methods to Dissociate Attached EBs and Obtain Neural Progenitor Cells (NPCs)

Figure 48:
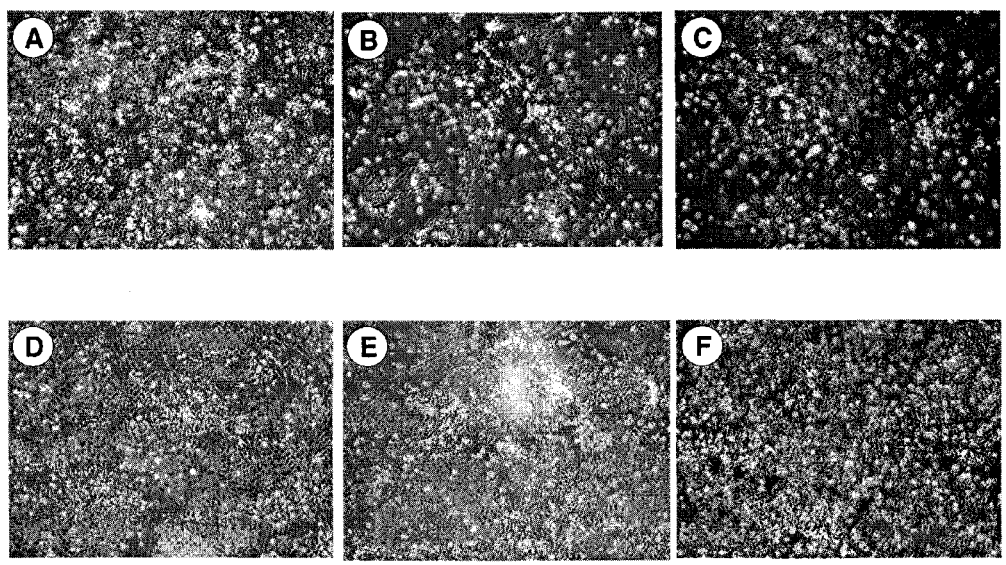
FIG. 48 shows neural progenitor cells (NPCs), which were obtained from attached EBs which were dissociated by different methods. EBs had been previously generated from hESCs line H9 p47 in AggreWell™ 400 and mTeSR™ 1-F with an osmolality of 270 mOsm/kg. They were cultured in suspension culture (ULA dishes) for 5 days prior to plating of the EBs. NPCs shown in (A) were derived from attached EBs using cell dissociation buffer enzyme-free PBS based, 0.02% EDTA solution (B), 1 mg/mL Dispase (C), Accutase™ (D), Neurocult® Chemical Dissociation Kit (Mouse) (E) or 0.05% trypsin-EDTA (F). Magnification 10×.
Figure 49:
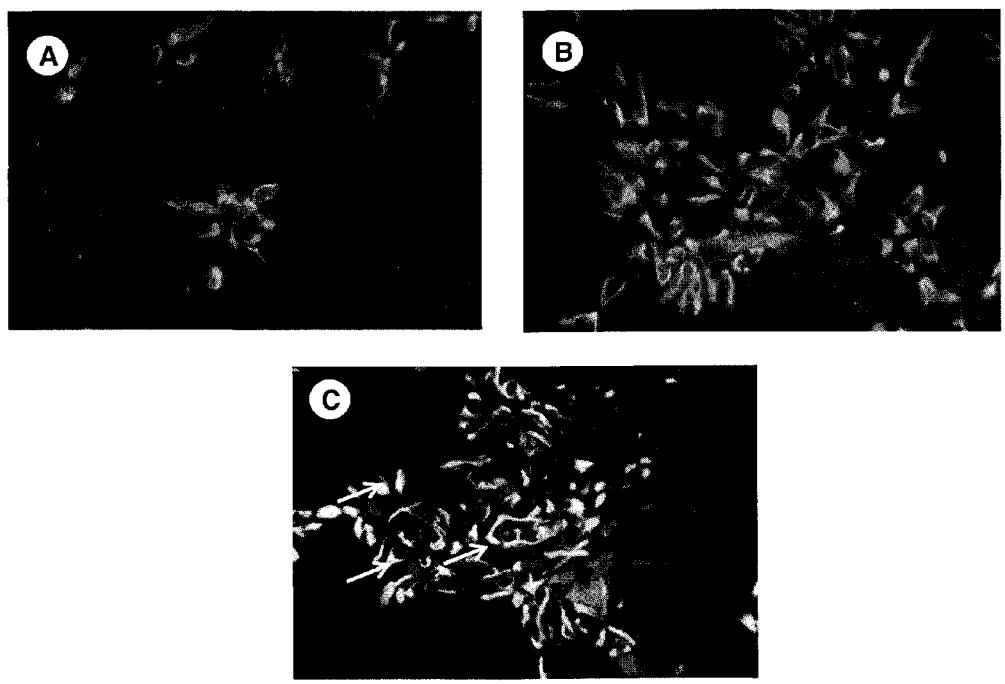
FIG. 49 shows neural progenitor cells (NPCs), which were obtained from attached EBs which were dissociated using different dissociation methods at 3 days after plating and stained using immunocytochemistry (ICC) for NPC marker Sox1 (stains the nucleus of the cell) and Nestin (stains the cytoplasm of the cell; arrows in (C). NPCs in (A) have been derived from attached EBs dissociated using Accutase™. NPCs shown in (B) have been derived from attached EBs dissociated using HBSS. NPCs shown in (C) have been derived from EBs dissociated using D-PBS without Ca++ and Mg++. Magnification 20×.

As described in Example 9, EBs containing 2000 cells per EB were formed in AggreWell™ 400 from the human embryonic stem cell line H9 p47 in mTeSR™ 1-F with an osmolality of 270 mOsm/kg. EBs were released after 24 hours, cultured in ULA dishes and plated after 5 days of culture onto Poly-L-ornithine/Laminin as described in Example 11. Seven to 8 days after plating, the attached EBs were dissociated using various dissociation agents: cell dissociation buffer enzyme-free PBS based (Gibco, catalog number 13151-014), EDTA (0.02%), Dispase 1 mg/ml (STEMCELL TECHNOLOGIES INC., catalog number 07923), Accutase (STEMCELL TECHNOLOGIES INC., catalog number 07920), Neurocult® Chemical Dissociation Kit (Mouse) (STEMCELL TECHNOLOGIES INC., catalog number 05707) and Trypsin (0.05%) (Sigma, check). Attached EBs were dissociated in cell dissociation buffer enzyme-free PBS based (Gibco, catalog number 13151-014) at room temperature for 0.5 to 1 hour. The same incubation procedure was applied using 0.02% EDTA solution. After the incubation, cells were dissociated by trituration in the solutions (approx. 10 times using a P-1000 pipette tip). The culture dish was washed once with 1 mL of DMEM/F-12 with 15 mM HEPES (STEMCELL TECHNOLOGIES INC., catalog number 36254) and cells were centrifuged as described in Example 14. The supernatant was discarded and the cell pellet was dissociated with 2 mL of mTeSR™ 1-F with an osmolality of 270 mOsm/kg and plated on Poly-L-ornithine/laminin or matrigel (or other) coated 6-well plates. Cells were plated in various densities, and in this example a 1 to 1 split was performed. For dissociation with Dispase, 1 mL of a 1 mg/ml solution of Dispase was added to the attached EB cultures after the removal of induction medium (mTeSR™ 1-F with an osmolality of 270 mOsm/kg) from the culture. Plates were placed in a 37° C. incubator and cultures were observed until attached EB colonies started detaching from the plate. This step usually took between 10 and 40 minutes. Dispase was removed and the cells were washed 3 times with DMEM-F12. Trituration and centrifugation steps are described above and in Example 14. Accutase was added to the cells after the induction medium was discarded and cells were incubated until all the cells detached from the plate (usually 5-10 minutes) as per standard protocols. 5 mL of DMEM-F12 were added to the cells to inactivate the Accutase and cells were dissociated gently 1-2 times using a P-1000 pipette tip. Centrifugation and dissociation of the pellet as well as plating are described above. The Neurocult® Chemical Dissociation Kit (Mouse) was used as described on http://www.stemcell.com/en/Products/All-Products/NeuroCult-Chemical-Dissociation-Kit-Mouse.aspx (Manual: Chemical Dissociation of Neurospheres Derived from Adult and Embryonic Mouse CNS using the NeuroCult® Chemical Dissociation Kit—2009). Dissociated cells were centrifuged, the cell pellet dissociated as well as the cells plated as described above and in Example 14. For trypsin dissociation, trypsin was used at a concentration of 0.05% to dissociate attached EB cultures. After the culture medium was aspirated, cells were incubated with pre-warmed (to 37° C.) Trypsin at 37° C. for 1-2 minutes or until they started detaching from the dish. Trypsin was deactivated by addition of 1-2 mL of 10% ES-Cult® Fetal Bovine Serum for Neural Differentiation (STEMCELL TECHNOLOGIES INC., catalog number 06955) in D-PBS Without Ca++ and Mg++ (STEMCELL TECHNOLOGIES INC., catalog number 37350). Trituration, centrifugation and plating steps are described above. FIG. 48 shows NPCs dissociated using the various described reagents 4-6 days after plating. FIG. 49 shows NPCs 3 days after re-plating, which had been dissociated with either Accutase (this example), HBSS (Example 52) or PBS (Example 14), that were stained for the NPC marker Nestin and Sox1. Note that NPCs were also plated at different densities. This Example shows that attached EBs can be dissociated with various reagents and the resulting suspension containing NPCs are comparable to each other in term of morphology and marker staining.

Figure 50:
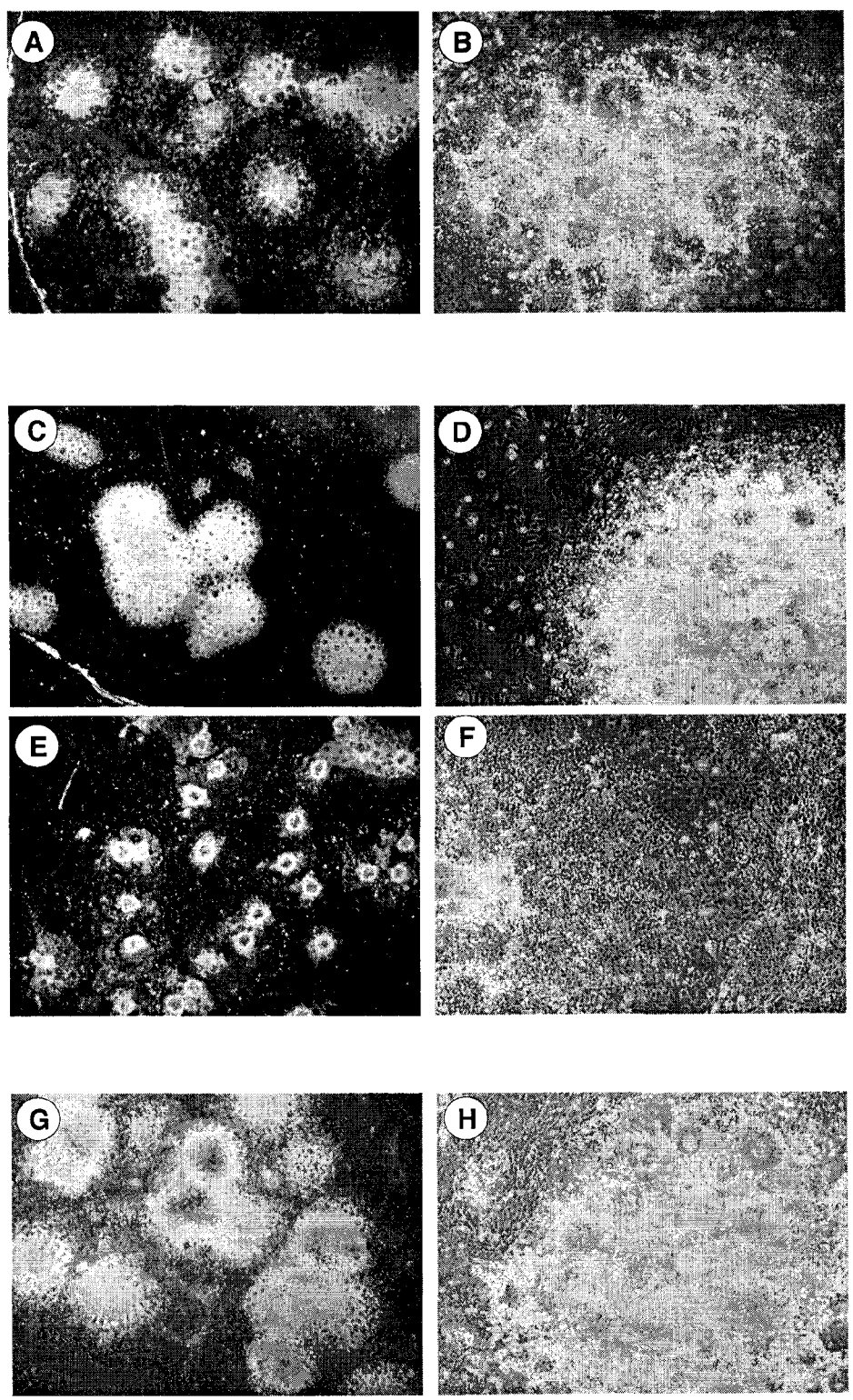
FIG. 50 shows attached EBs containing 2000, 5000 and 10000 cells/EB generated from hESC lines H7 and H9 (passages 38 or 35, 36, 41, 45, respectively) at different days after plating. EBs were also released from AggreWell™ 800 plates at different time points. Attached EBs (5000 cells/EB at initial formation) shown in (A, B) were released and plated on day 5 and the picture is representative of the cell morphology at day 7 after plating. Attached EBs (10000 cells/EB at initial formation) shown in (C, D) were released and plated on day 5 and the picture is representative of the cell morphology at day 7 after plating. Attached EBs (2000 cells/EB at initial formation) shown in (E, F) were released and plated on day 11 and the picture is representative of the cell morphology at day 5 after plating. Attached EBs (10000 cells/EB at initial formation) shown in (G, H) were released and plated on day 6 and the picture is representative of the cell morphology at day 8 after plating. Magnification 2× (A, C, E, G), 10× (B, D, F, H).
Figure 51:
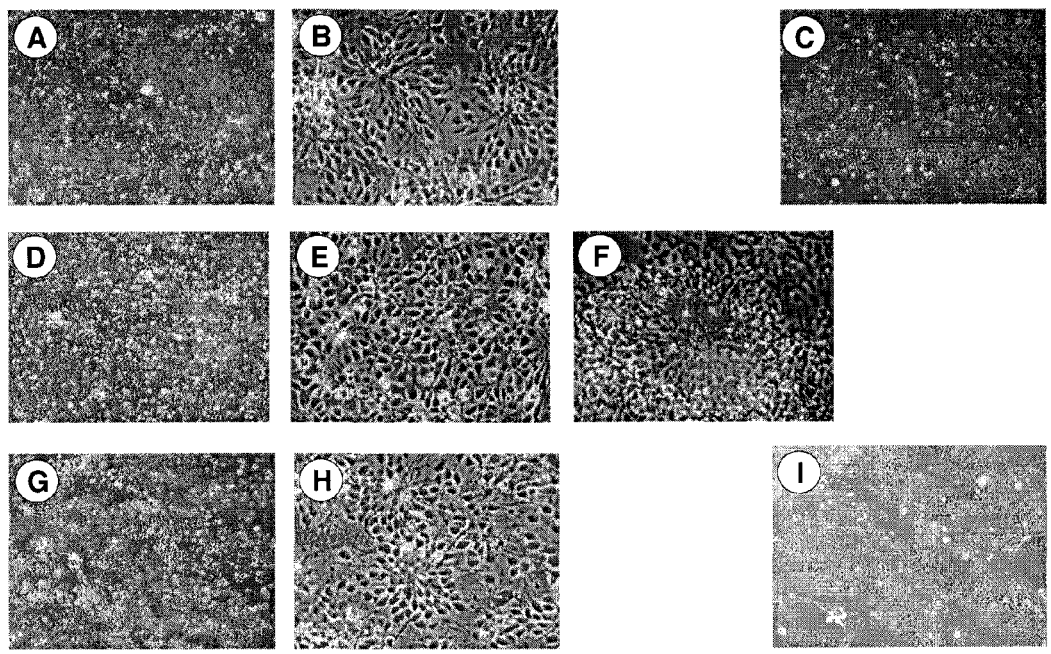
FIG. 51 shows NPC 5 (A, B) or 6 days (C-I) after plating from dissociated attached EBs (described in FIG. 50). EBs were previously released at different days from AggreWell™ 800 plates. NPCs shown in (A, B) were dissociated on day 5 after attachment of EBs (2000 cells/EB) which were released from AggreWell™ 800 on day 8. NPCs shown in (C) were dissociated on day 8 after attachment of EBs (10000 cells/EB), which were released from AggreWell™ 800 on day 6. NPCs shown in (D, E, F) were dissociated on day 7 after attachment of EBs (5000 cells/EB), which were released from AggreWell™ 800 on day 5. NPCs shown in (G, H) were dissociated on day 7 after attachment of EBs (10000 cells/EB), which were released from AggreWell™ 800 on day 5. NPCs shown in (I) were dissociated on day 6 after attachment of EBs (5000 cells/EB), which were released from AggreWell™ 800 on day 5. Magnification 20× (A, D, G), 40× (B, C, E, F, H, I).
Figure 52:
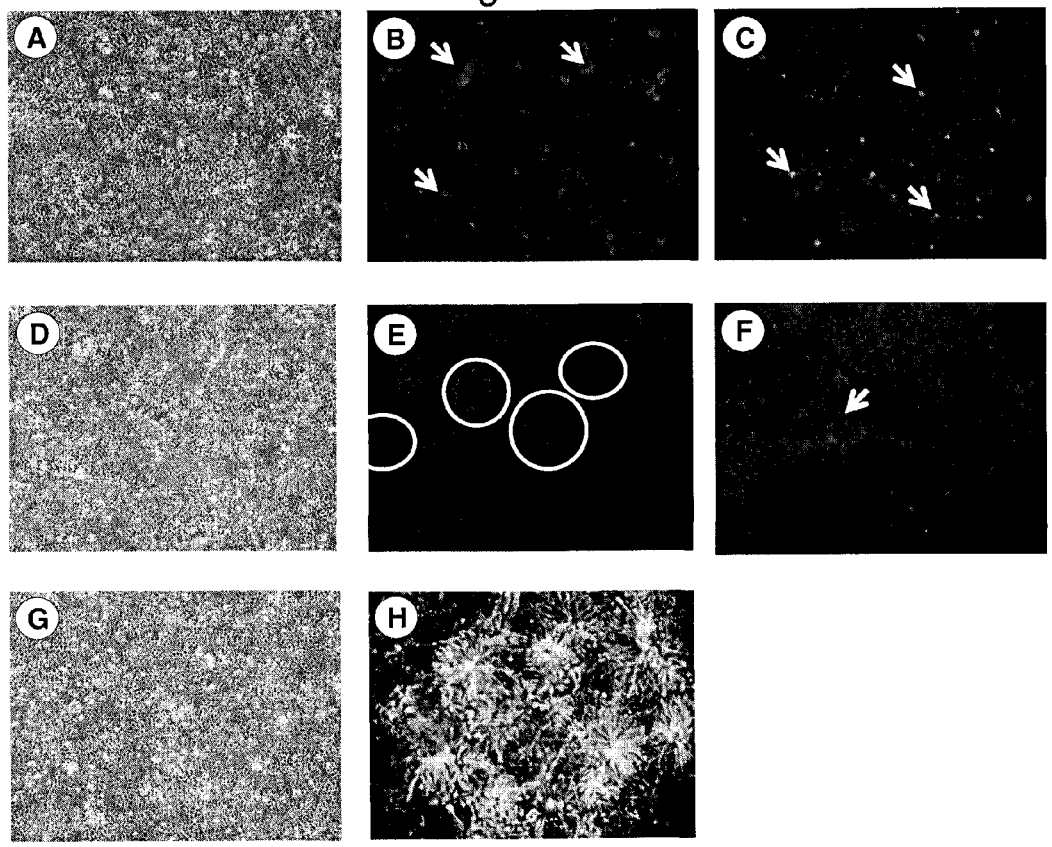
FIG. 52 shows NPC 4 days after they isolated from dissociated attached EBs and plated (represented in FIG. 50). EBs were released from AggreWell™ 800 plates at different days. NPCs shown in (A) were isolated on day 11 after attachment of EBs (2000 cells/EB), which were released from AggreWell™ 800 on day 7. (B) shows an immunocytochemical (ICC) staining of the same NPCs for the neuronal marker PSA-NCAM (arrows point towards positively stained lumina of rosette structures). (C) shows an ICC staining of the same NPCs for the neuronal rosette marker ZO-1, staining the lumen of the rosette specifically (arrows). NPCs shown in (D) were isolated on day 9 after attachment of EBs (2000 cells/EB), which were released from AggreWell™ 800 on day 9. (E) shows an ICC staining of the same NPCs for the neuronal marker Sox1 (circles mark some of the rosette structures present). (F) shows an ICC staining of the same NPCs for the neuronal marker Nestin (Nestin stains the cytoplasm as marked here by an arrow, all cells are positive). NPCs shown in (G) were isolated on day 7 after attachment of EBs (2000 cells/EB), which were released from AggreWell™ 800 on day 11. (H) shows an ICC staining of the same NPCs for the neuronal marker Nestin (all cells are positive). All stained cells are counter-stained in blue using DAPI. Magnification 10× (A, D, G), 20× (B, C, E, F, H).
Figures 53, 54:
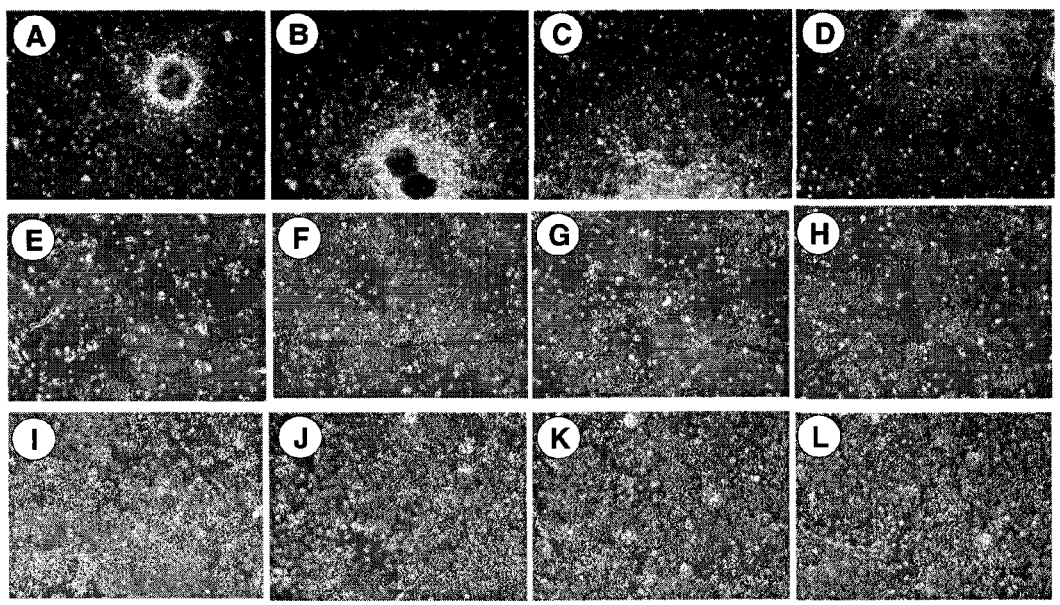
FIG. 53 shows a chart, which summarizes the results from FIGS. 50-52 including a list of the age of NPCs at the end of passage 2 and the source of NPCs: 1. The day EBs were released from their microwell, 2. The day NPCs were isolated from attached EBs (shown in FIG. 50), 3. The total number of days at dissociation of attached EBs (shown in FIG. 50), 4. The number of cells per EB and 5. The day the picture of NPCs (shown in FIG. 51 or 52) was taken total, which equals the number of days in culture.
FIG. 54 shows attached EBs and the isolated NPCs, generated from hESC line H9 p65. EBs were formed in AggreWell™ 800 plates at a size of 2000 cells per EB. EBs were cultured in the plates for 12 days until they were released. (A-D) show attached EBs at day 4 after plating. (E-H) show NPCs 3 days after they have been isolated from attached EBs and were plated on 1, 5, 10 and 20 μg/ml laminin (E-H, respectively). (I-L) show the same NPCs 7 days after plating. Magnification 10×.

Example 52. Efficient Isolation of Neural Progenitor Cells from Neural Rosettes within Attached EBs of Different Sizes Plated at Different Time Points As described in Example 30, EBs containing 2000, 5000 and 10000 cells/EB were formed in AggreWell™ 800 from the human embryonic stem cell lines H7 and H9 (passages 38 or 35, 36, 41, 45, respectively). EBs were cultured for 5 days within AggreWell™ microwell devices in mTeSR™ 1-F with an osmolality of 270 mOsm/kg. EBs were released for subsequent plating according to methods described in Example 31 with the exception that EBs were harvested from the microwells at different time points (day 5, 6, 7, 9 and 11). FIG. 50 shows attached EBs (various sizes) at different time points (at day 5, 6 and 11) after releasing them from AggreWell™ 800 plates shown on the day the attached EBs were dissociated to obtain NPCs (only representative examples are shown). Neural rosettes were present in all conditions. NPCs were selectively isolated from attached EBs using the method described in Example 14 with the exception that in this example Hanks' Balanced Salt Solution (HBSS), calcium and magnesium free ($Ca^{2+}$ and $Mg^{2+}$) (Sigma catalog number C1419) was used. The cells were incubated for 0.5-2 hours at room temperature after the induction medium (mTeSR™ 1-F with an osmolality of 270 mOsm/kg) was discarded. Cells were dissociated and centrifuged as described in Example 14. The supernatant was removed and the cell pellet was dissociated with 2 mL of mTeSR™ 1-F with an osmolality of 270 mOsm/kg. NPCs were re-plated at various densities onto Poly-L-ornithine/Laminin (for coating procedure see Example 18). FIG. 51 shows isolated re-plated NPCs, at days 5 or 6 of culture, which were isolated from EBs plated at different time-points and also dissociated at different time-points. FIG. 52 shows NPCs 4 days after re-plating and also contains pictures of immunocytochemically (for method see Example 17) stained cells for markers of NPCs (PSA-NCAM, SOX1 and Nestin, as well as ZO-1, a tight junction protein and marker for the lumen of rosettes). For clarity, the table in FIG. 53 summarizes the individual experiments: the first column indicates the day the EBs were released from the AggreWell™ 800 plate. The second column indicates the day the attached EBs were dissociated, the third column indicates the number of days in total since formation of EBs in AggreWell™ and mTeSR™ 1-F 270 mOsm/kg, the fourth column indicates the size of the EB and the fifth column indicates the day the picture was taken with the total number of days the NPCs were in culture.

Figure 55:
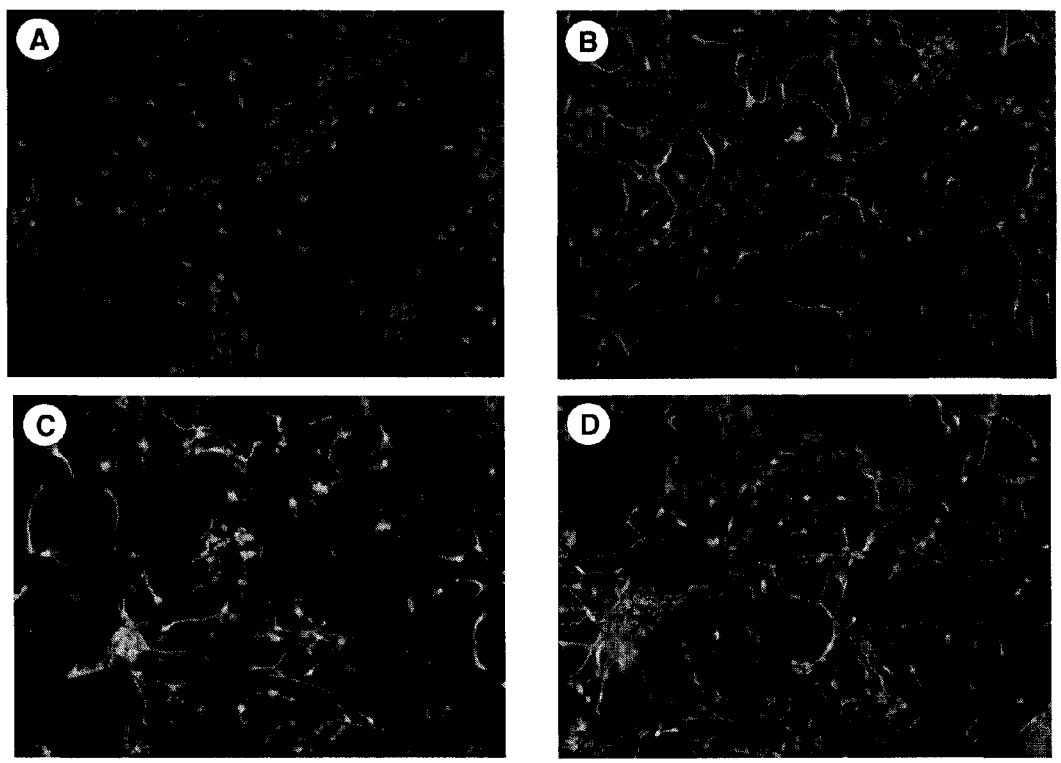
FIG. 55 shows NPCs shown in FIG. 54 stained with an antibody against TUJ-1 on day 3 when plated on 10 μg/ml laminin or 20 μg/ml laminin and on day 7 when plated on 1 μg/ml laminin or 5 μg/ml laminin (neurons can be identified by their bright appearance and the axons they are extending). Cells are counter-stained in blue using DAPI. Magnification 20×.

Example 53. Efficient Isolation of Neural Progenitor Cells from Neural Rosettes within Attached EBs and Culture of These Cells on Different Concentrations of Laminin As described in Example 30, EBs containing 2000 cells/EB were formed in AggreWell™ 800 from the human embryonic stem cell line H9 (p65) EBs were cultured for 12 days in these AggreWell™ microwell devices in mTeSR™ 1-F with an osmolality of 270 mOsm/kg. EBs were released for subsequent plating according to methods described in Example 31 with the modification that EBs were plated on day 12. Neural progenitor cells were isolated from attached EBs at day 4 after plating according to the methods described in Example 51. In this example trypsin at a concentration of 0.05% was used. Cells were re-plated into a 6-cm well coated either with Poly-L-ornithine or 4 different concentrations of laminin. Coating was performed as described in Example 18 with the modification of the laminin concentrations. FIG. 54 shows attached EBs at day 4 after plating (upper row). The middle row shows NPCs 3 days after they have been isolated from attached EBs plated on 1, 5, 10 and 20 µg/ml laminin (from left to right). The lower row shows the same cells 7 days after plating. FIG. 55 shows an immunocytochemical staining of NPCs on day 3 on 10 and 20 µg/ml laminin and on day 7 on 1 and 5 µg/ml laminin. The staining was performed as described in Example 17 and cells were stained for TUJ-1, a neuronal marker to determine the effect of concentration of laminin on number of neurons. This example shows that NPCs can be re-plated on various concentrations of laminin with no influence on morphology or marker expression of attached neural/neuronal cells.

Figure 56:
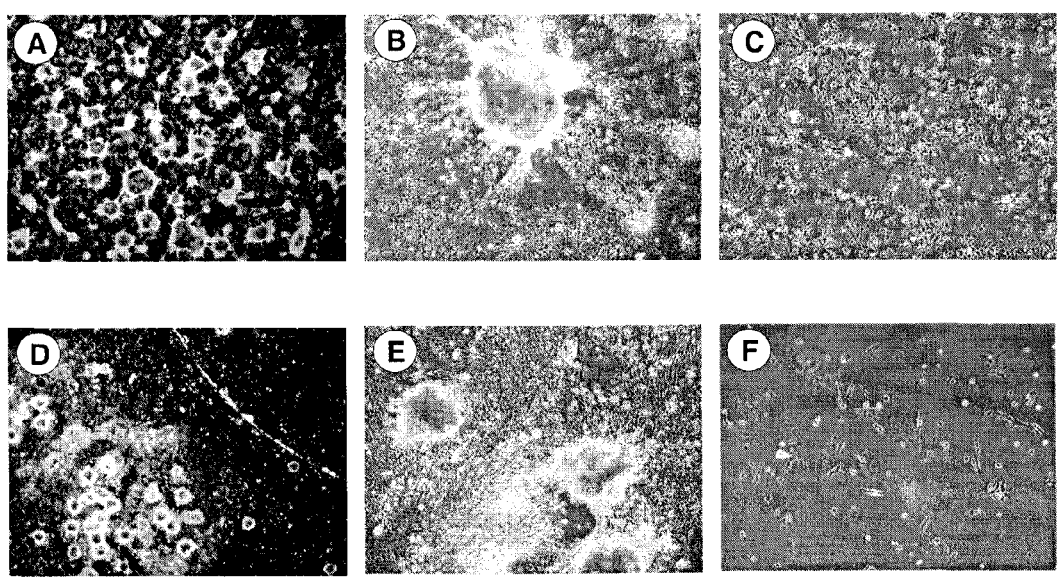
FIG. 56 shows attached EBs and the isolated NPCs generated from hESC line H9. EBs were generated in AggreWell™ 800 and were released and plated at day 11. The pictures of the attached EBs were taken at day 11 after attachment (A, B, D, E). NPCs were derived from these attached EBs and are shown on day 3 after plating (C, F). mTeSR™ 1-F 270 mOsm/kg (A-C) or mTeSR™ 1-F 340 mOsm/kg (D-F) were used for the formation of EBs, culture of the attached EBs and subsequent culture of NPCs. Magnification 2× (A, B, D, E), 10× (C, F).
Figure 57:
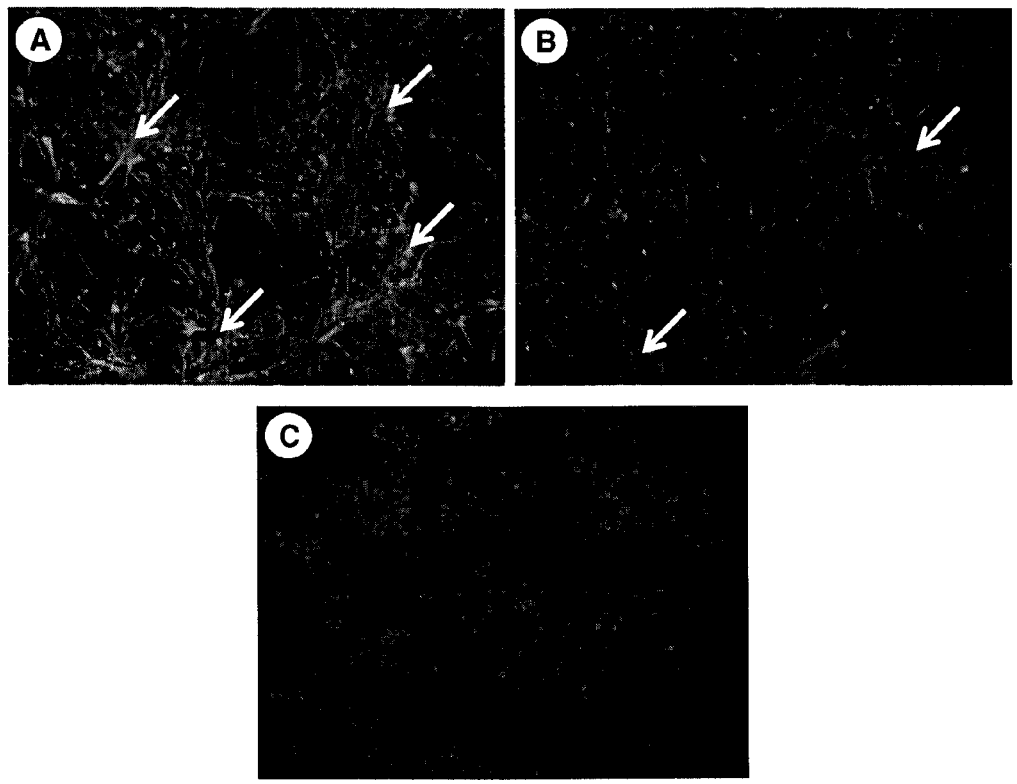
FIG. 57 shows NPCs described in FIG. 56 stained with antibodies against the neural marker Nestin, the neuronal marker TUJ1 (A, B) and the neural marker Sox1 (C). Arrows in (A) and (B) mark regions with high density of Nestin positive cells (less in (B)). Many cells express Sox1. Magnification 20×.

Example 54. Efficient Dissociation and Isolation of Neurons and Neural Progenitor Cells from EBs Generated and Cultured for 22 Days in mTeSR™ 1-F Osmolality 270 mOsm/kg or 340 mOsm/kg EBs containing 2000 cells/EB were formed in AggreWell™ 800 from the human embryonic stem cell line H9 as described in Example 30 using mTeSR™ 1-F with an osmolality of 270 mOsm/kg or 340 mOsm/kg. EBs were released from the microwell plates at day 11 of culture and plated onto Poly-L-ornithine/Laminin coated dishes as described in Example 31. Neural progenitor cells were isolated from attached EBs at day 11 after plating according to the methods described in Example 53. FIGS. 56 and 57 show the attached EBs at day 11 after plating. There are not only NPCs present in the cultures but also mature neurons growing out from the attached EB structures formed and cultured in mTeSR™ 1-F with an osmolality of 270 mOsm/kg. There are only few NPCs and neurons observed in EBs formed and grown in mTeSR™ 1-F with an osmolality of 340 mOsm/kg. NPCs could only be generated from dissociated EBs grown in mTeSR™ 1-F with an osmolality of 270 mOsm/kg and not from mTeSR™ 1-F with an osmolality of 340 mOsm/kg. Immunocytochemistry (see Example 17) of re-plated cells at day 3 shows a mixture of NPCs and neurons as determined by Nestin and Sox1 or TUJ-1 expression respectively.

Figure 58:
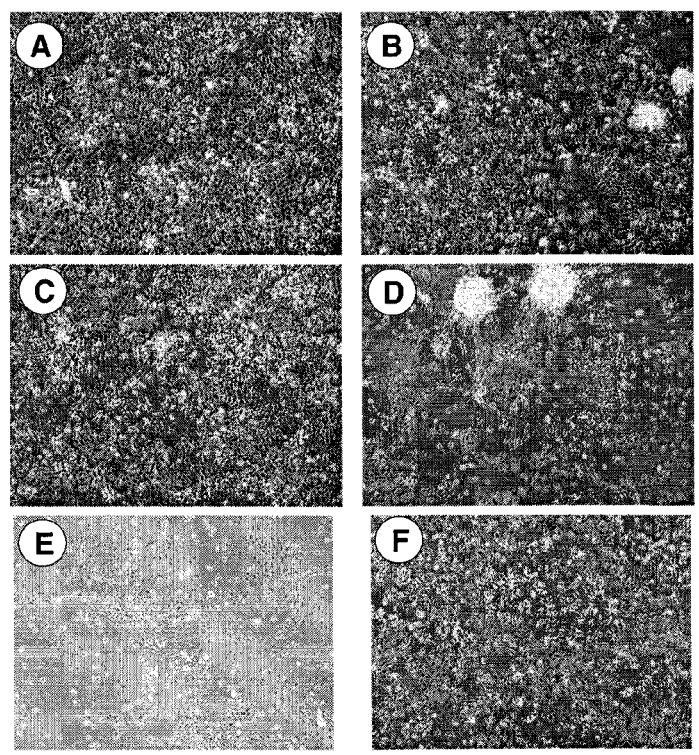
FIG. 58 shows NPCs derived from hESC line H9 p36 and p41. EBs were formed at different sizes (2000, 5000 and 10000 cells/EB) in AggreWell™ 800 and released on day 5 or 7. NPCs were isolated from attached EBs at day 11 (for the 2000 cells/EB) or at day 7 (5000 and 10000 cells/EB). (A) shows NPCs isolated from EBs previously cultured in AggreWell for 7 days (2000 cells/EB), grown as attached EB-cultures for 11 days and then treated with HBSS on day 4 of culture. (B) shows NPCs on day 6 isolated from attached EBs at day 7 using HBSS; these EBs (10000 cells/EB) were previously cultured in AggreWell for 5 days. C) shows passage 2 NPCs on day 3 of culture after dissociation using HBSS of cells from (A). These NPCs were plated onto Poly-L-ornithine/laminin coated dishes. (D) shows passage 2 NPCs on day 1 of culture after dissociation using TrypIE of cells from (B). These NPCs were plated onto matrigel coated dishes. E) shows passage 3 NPCs on day 3 of culture after a dissociation using Trypsin of cells from (C). These NPCs were plated onto Poly-L-ornithine/laminin coated dishes. (F) shows passage 3 NPCs on day 4 of culture after dissociation using TrypIE of cells from (D). These NPCs were plated onto Poly-L-ornithine/laminin coated dishes. Magnification 10×.
Figure 59:
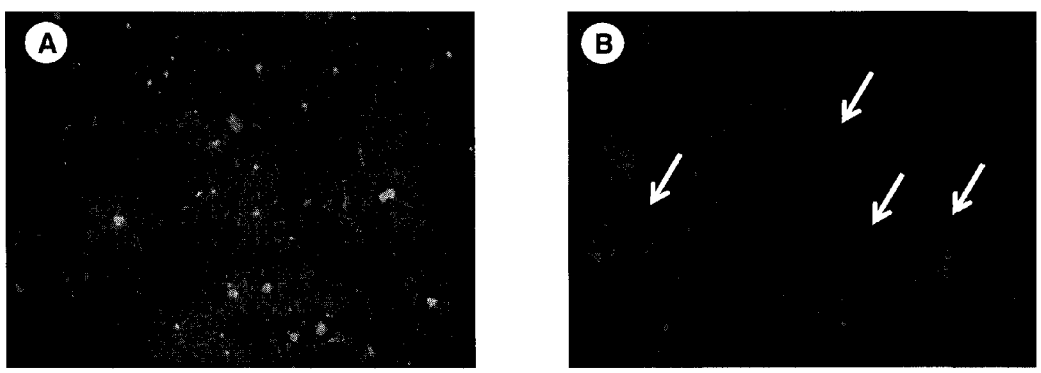
FIG. 59 summarizes the results described in FIG. 58. (A) shows NPCs on day 5 of passage 1 stained for the neural marker musashi and with the rosette-marker ZO-1 (all cells are musashi positive, ZO-1 stains the lumen of the prominent rosette structures). (B) shows NPCs on day 6 of passage 1 (p1d6) stained for the neuronal marker TUJ-1 (arrows mark some axonal structures). Magnification 20×.

Example 55. Propagation of Neural Progenitor Cells for Several Passages Testing Different Dissociation Reagents and Surface Coatings EBs containing 2000 or 10000 cells/EB were formed in AggreWell™ 800 from the human embryonic stem cell line H9 (p 36 and 41) as described in Example 30 using mTeSR™ 1-F with an osmolality of 270 mOsm/kg. EBs were released from the microwell plates and plated onto Poly-L-ornithine/Laminin coated dishes as described in Example 31. EBs containing 2000 cells were released from AggreWell at day 7 and EBs containing 5000 or 10000 cells were released on day 5 of culture in AggreWell. Neural progenitor cells were isolated from attached EBs at day 11 (for the 2000 cells/EB) or at day 7 (5000 and 10000 cells/EB) after plating according to the methods described in Example 52. FIG. 58 shows NPCs on day 4 (2000 cells/EB) or 6 (10000 cells/EB) of culture on Poly-L-ornithine/Laminin coated dishes (passage 1=P1). These NPCs were dissociated with either HBSS or TrypIE (Sigma, catalog number) and resulting cells were re-plated as secondary cultures on Poly-L-ornithine/Laminin or matrigel coated dishes (for 2000 or 10000 cells per EB respectively). The HBSS dissociation was performed by incubating the NPCs between 0.5 and 1 hour at room temperature and cell detachment was observed. The cells were triturated gently 5-10 times in the HBSS solution using a P-1000 pipette tip. Cells were centrifuged and the cell pellet dissociated as described in Example 52. For detaching NPCs using TrypIE, the methods of Examples 51 and 53 were used. FIG. 58 shows the passage 2=P2 cells on day 3 (2000 cells/EB) or day 1 (10000/cells per EB) which were plated at a density of $1.3 \times 10^5$ cells/cm$^2$. Cells were treated at passage 3 (P3) with Trypsin (2000 cells/EB) (see Examples 51 and 53) or TrypIE (10000 cells/EB) on day 3 or 2 respectively. FIG. 58 shows P3 cells on day 3 or 4 respectively which are a total of 29 or 24 days post induction. The table in FIG. 59 summarizes the different time-points the splits were performed on cells originating from 2000 or 10000 cell containing EBs. Immunocytochemical staining (for method see Example 17) was performed for neural progenitor markers, showing Musashi, a neuronal precursor cell marker and ZO-1 expression, which is a marker for the lumen of the rosette (FIG. 59). NPCs are shown on p1d5 cells stained for Musashi and ZO-1 (originating from 2000 cells/EB). Rosettes can also be seen in p1d6 cells originating from 10000 cells/EB as shown by DAPI-cell staining. Mature neurons are mixed in with the NPCs (here shown with the marker TUJ-1). The results were obtained from cells cultured in mTeSR™ 1-F with an osmolality of 270 mOsm/kg but NPCs can also be cultured in mTeSR™ 1-F with an osmolality of 270 mOsm/kg supplemented with bFGF (10-20 ng/mL), EGF (10-20 ng/mL), B27 (1-2×) or N2A (1×).

This example shows that various dissociation agents can be used to dissociate NPCs for sub-culture over 3 passages and that these NPCs can be replated on different matrices.

Therefore neural rosette structures obtained by mechanical isolation and resulting NPCs re-plated as described in Example 15 or by any of the described dissociation methods in Examples 51 and 55 can be used to dissociate NPCs for further propagation over multiple passages. In summary, the previous 5 examples show that NPCs can be isolated from EBs harvested at different times from AggreWell™ 800, attached EBs displaying rosettes at different time-points and when attached EBs are cultured for different days. EBs can either be cultured in the AggreWell™ microwells for 24 hours or then released to be cultured in ULA plates or they can be left inside the microwells for up to 12 days. Also various sizes of EBs can be formed and NPCs can be isolated from those EBs with similar efficiencies. Furthermore, various dissociation reagents can be used to isolate NPCs and NPCs can be re-plated on different concentrations of laminin as well as on different surfaces. NPCs can be isolated during a time frame of 3 to 11 days after plating the EBs (this equals 11 to 22 days in total) and can be passaged several times without losing their ability to propagate as NPCs as well as spontaneously differentiate into neurons and astrocytes, see Example 57 and FIG. 66.

Figure 60:
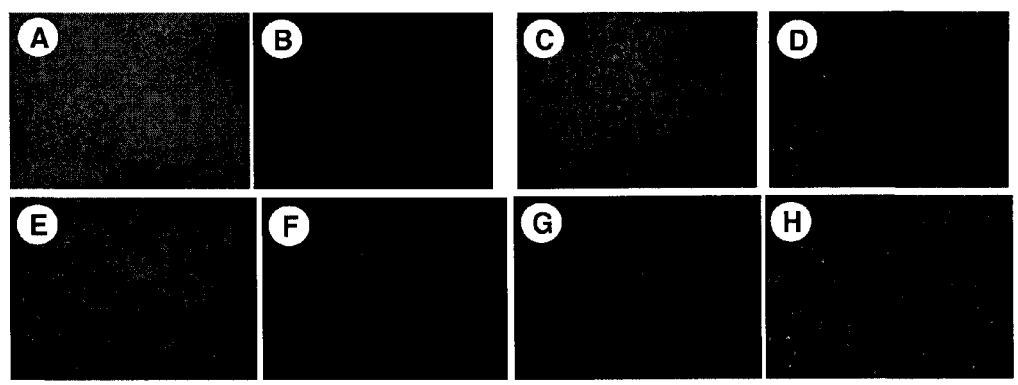
FIG. 60 shows attached EBs stained for the neural markers Pax6 (A, E) and Sox1 (B, F). (C, G) represent overlays of the two markers and (D, H) show DAPI-counter-stain of the cells. EBs containing 500 cells/EB were formed from hESC line H9 p63 in AggreWell™ 400 and were released and plated after 5 days. The induction medium mTeSR™ 1-F 270 mOsm/kg was used for the culture of attached EBs shown in (A-D) while mTeSR™ 1-F 340 mOsm/kg was used for the culture of attached EBs shown in (D-H). It can be seen from (A, C and D) compared to (E, G and H) that cells derived from EBs formed and cultured in mTeSR™ 1-F 270 mOsm/kg express more of the neural marker Pax6 and Sox1. Magnification 10×.
Figure 61:
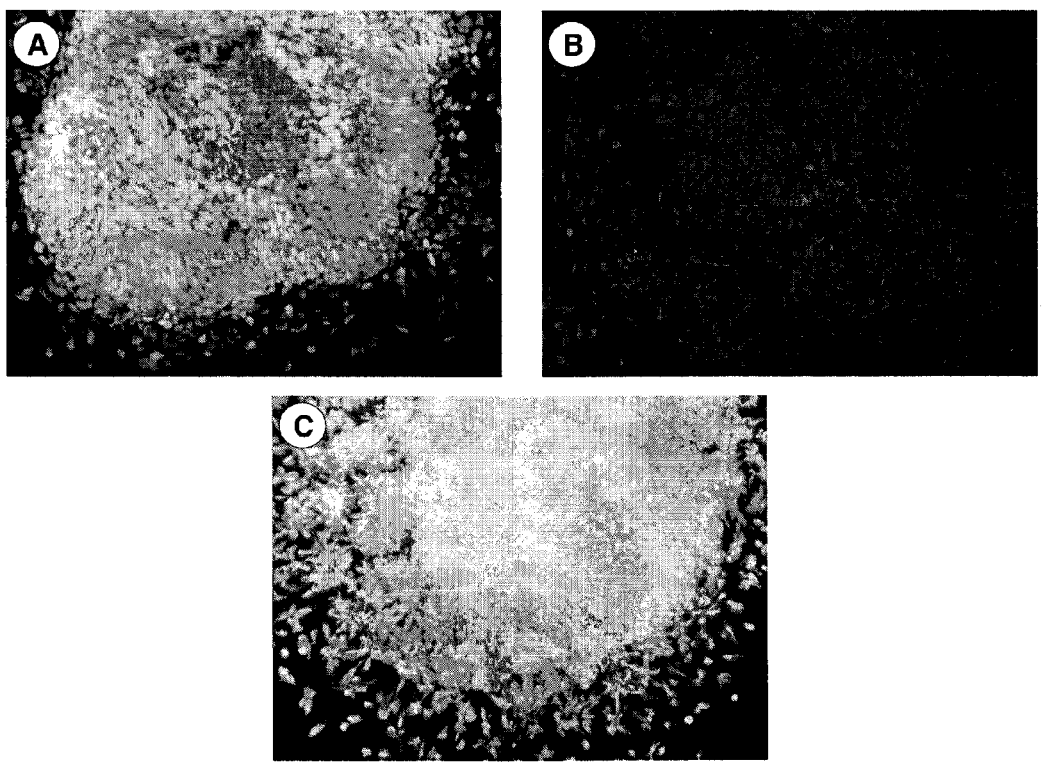
FIG. 61 shows attached EBs from various experiments and at different days after plating co-stained for the neural markers Pax6 and Sox1 (A), Sox1 and Nestin (B) and Sox1 and Nestin (C) to demonstrate abundance of neural progenitor cells. All cells co-express all 3 marker combinations, respectively. Magnification 10×.
Figure 62:
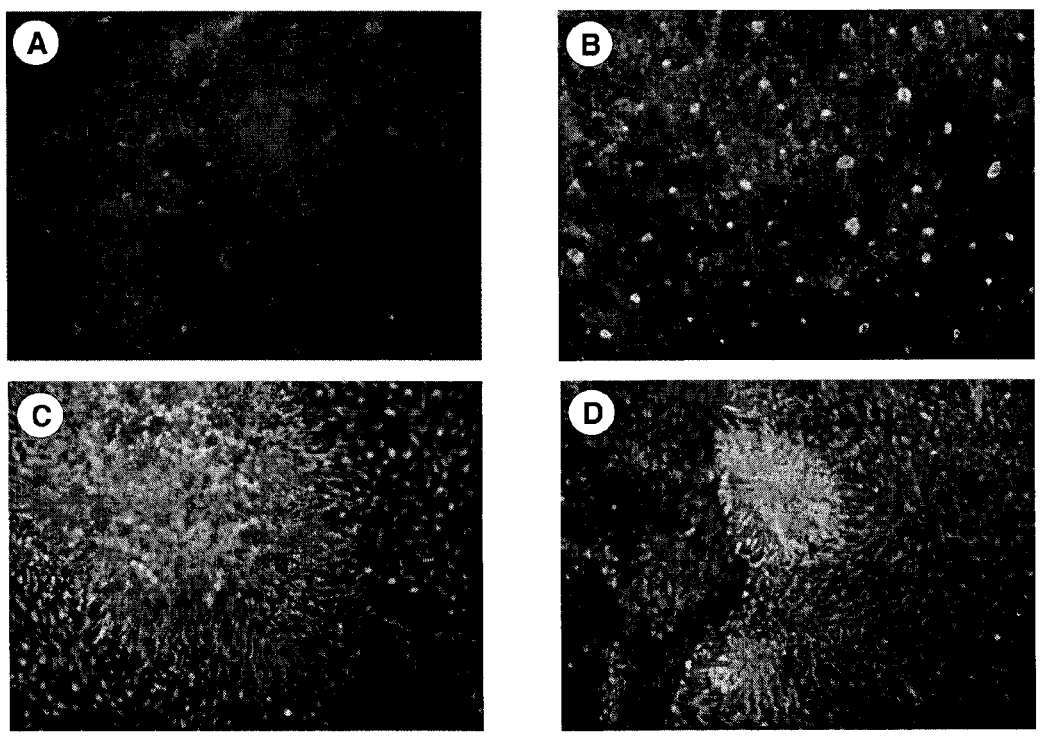
FIG. 62 shows attached EBs from various experiments and at different days after plating co-stained for the neural markers Pax6 and the rosette marker ZO-1 (A), the neural marker Sox1 and the rosette marker ZO-1 (B) as well as the radial glia marker BLBP and the neural marker Nestin (C, D). All cells are double-positive in (A) and (B) and rosette structures in (C) and (D), are double-positive for Nestin and BLBP appearing bright in the picture. Magnification 10× (A, B), 20× (C, D).
Figure 63:
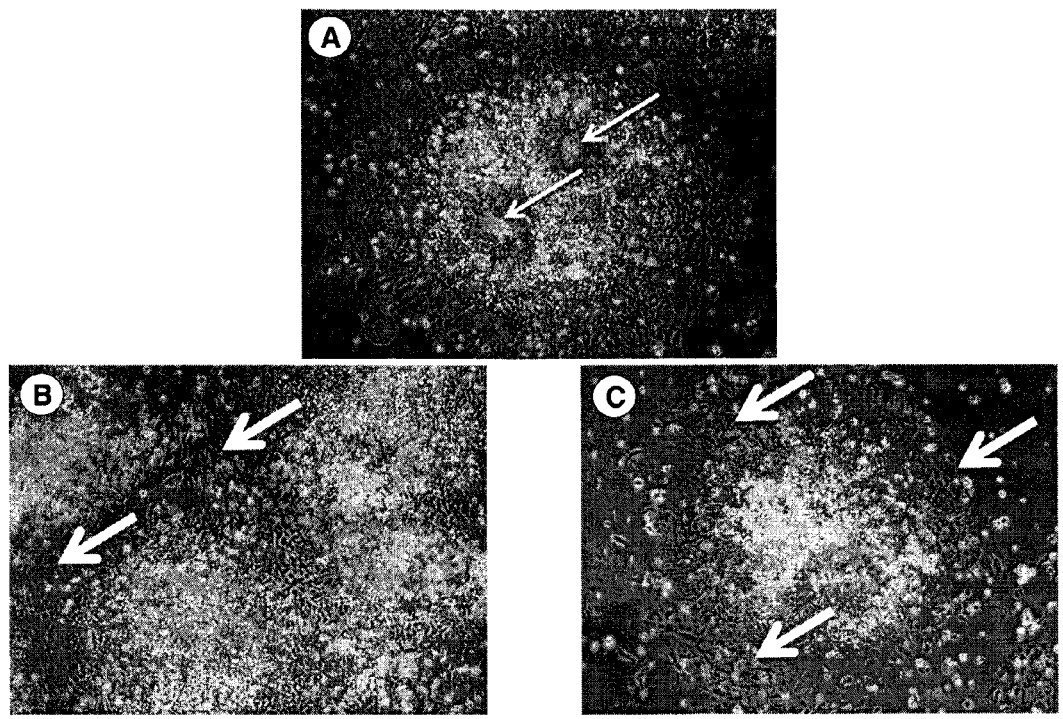
FIG. 63 shows attached EBs 2 days after plating. EBs were generated from hESC line H9 p51 in mTeSR™ 1-F 270 mOsm/kg (A) or mTeSR™ 1-F 340 mOsm/kg (B, C). Narrow arrows in (A) point towards neural rosettes. Broad arrows in (B and C) point towards flat cells surrounding attached EBs. Note that no neural rosettes are present in these illustrations. Magnification 10×.
Figure 64:
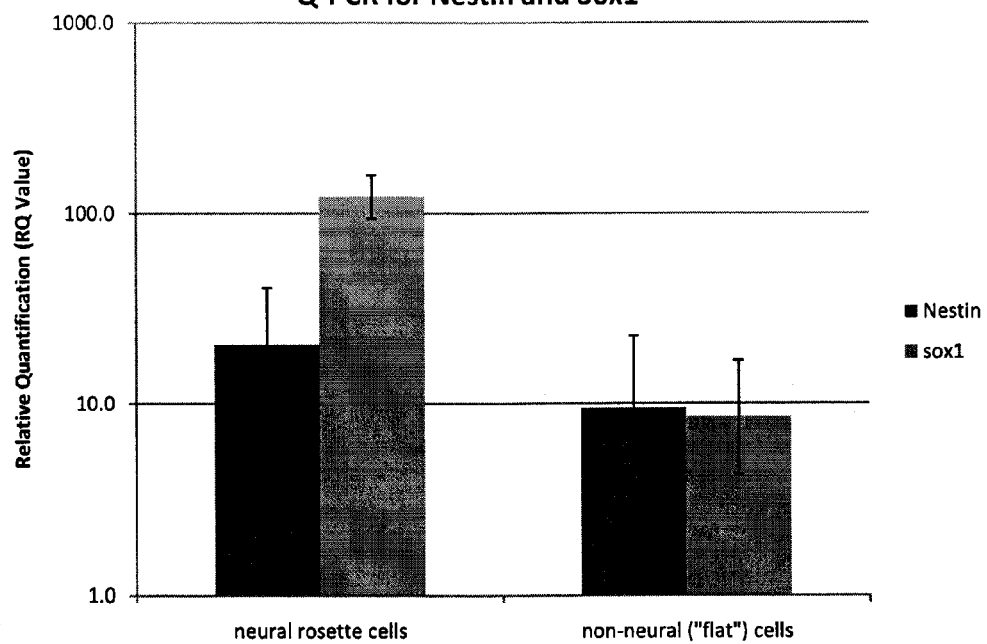
FIG. 64 shows a graph representing qPCR results (relative quantification (RQ value)) of Nestin (dark grey) and Sox1 (light grey) transcript expression in neural rosette cells and non-neural "flat" cells isolated from attached EBs at day 2 (described in FIG. 63) generated previously from H9 p52 hESCs in mTeSR™ 1-F 270 mOsm/kg or mTeSR™ 1-F 340 mOsm/kg, respectively.

Example 56. Phenotypic and Molecular Characterization of Cells within Neural Rosettes Generated in mTeSR™ 1-F with an Osmolality of 270 mOsm/kg and Non-Neural Cells Generated in mTeSR™ 1-F with an Osmolality of 340 mOsm/kg In this example hESCs line H9 passage 63 was used. EBs containing 500 cells per EB were formed as described in Example 28 in AggreWell™ 400 and EBs were released after 5 days of culture in the microwells and attached to Poly-L-ornithine/laminin coated dishes as described in Example 29. Two media were used: mTeSR™ 1-F with an osmolality of 270 mOsm/kg and mTeSR™ 1-F with an osmolality of 340 mOsm/kg. To characterize neural progenitor cells present in neural rosettes of attached EBs, immunocytochemistry was performed as described in Example 17. Markers for NPCs that are described in literature were used. The earliest neural marker used was Pax6, followed by the later marker Sox1 and Nestin. Pax6 and Sox1 were expressed within rosettes of attached EBs formed in mTeSR™ 1-F with an osmolality of 270 mOsm/kg and weakly expressed or absent in EBs formed in mTeSR™ 1-F with an osmolality of 340 mOsm/kg as shown in FIG. 60. FIG. 61 shows co-expression of Pax6, Sox1 and Nestin marker expression in attached EBs from multiple experiments formed in mTeSR™ 1-F with an osmolality of 270 mOsm/kg. FIG. 62 shows co-expression of Pax6 and Sox1 with ZO-1. FIG. 62 also shows staining for BLBP, a marker of radial glia cells within rosette structures. FIG. 63 shows non-neural cells which emerge mainly in EBs formed and cultured in mTeSR™ 1-F with an osmolality of 340 mOsm/kg, which have no rosette structures and are "flat" in morphology (in this example H9 p52 hES cells were used). It is likely that these flat cells and the non-rosette structures are derived of mesoderm or endoderm lineage. These cells were scraped with a 200 P pipette tip by gently moving it back and forth in between attached EB colonies to obtain cells for qPCR. As a control, rosette structures were manually selected. Both cells types were transferred into a 1.5 mL Eppendorf tube and centrifuged at maximum speed for 1-2 minutes. RNA was extracted using Trizol (Invitrogen, catalog number 15596-018) and standard methods. Single round reverse transcriptase PCR was performed to generate cDNA copy (remaining RNA was digested using RNase) and cDNA was amplified using gene-specific primers and SybrGreen™ (GE Healthcare) using the manufacturer's protocols. Amplification of the desired products by SybrGreen incorporation was monitored using a 7900-HT machine (Applied Biosystems) and data analysis performed using standard programs (RQ Manager 1.2). The qPCR results are shown in FIG. 64 and demonstrate that Nestin and Sox1 transcripts are higher in "neural rosette cells" than in "non-neural (flat) cells".

In summary, morphological, immunocytochemical characterization as well as FACS and qPCR for neural markers show that induction of neural ectoderm in mTeSR™ 1-F with an osmolality of 270 is efficient and NPCs can be isolated and propagated as well as differentiated into neurons and astrocytes. In comparison EBs formed in mTeSR™ 1-F with an osmolality of 340 mOsm/kg do not enrich for neural rosette structures and NPCs cannot be isolated. It is likely that osmolality of above 280 and 340 mOsm/kg enriches for non-ectodermal cells which have a different morphology than neural derived cells and are derived of mesoderm or endoderm lineage.

Figure 65:
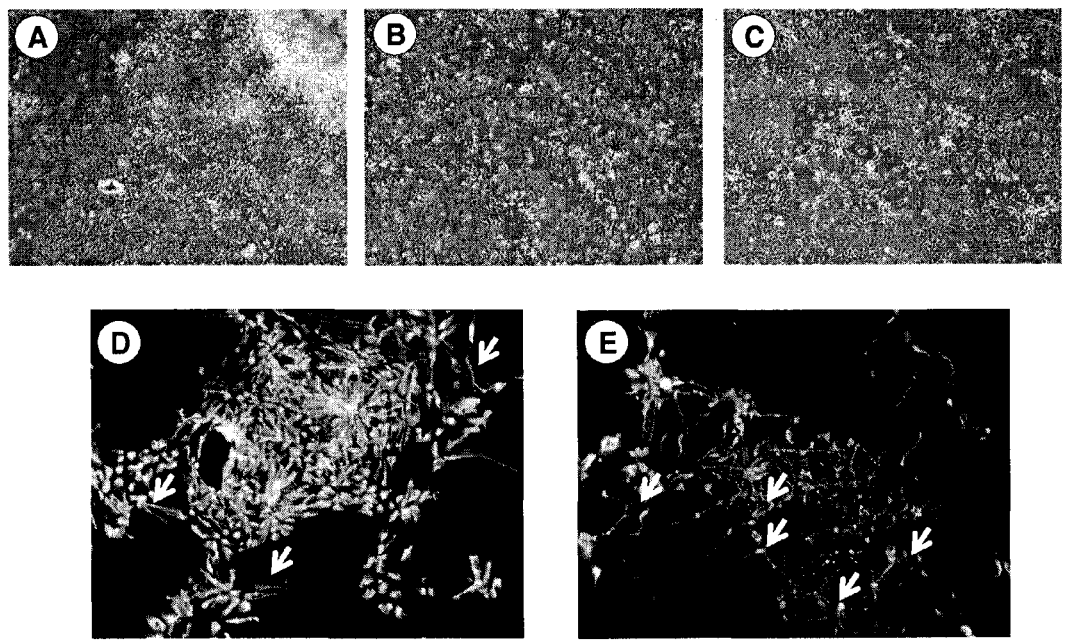
FIG. 65 shows NPCs (H9; p36 cells) at passage 1 day 8 (p1d8) (A), p2d2 (B) and p3d3 (C). NPCs were derived from attached EBs on day 5 after plating (released from AggreWell at day 5). In passage 1 and 2 mostly NPCs were observed, while in passage 3 sub-populations of neurons emerged spontaneously. (D) shows cells in p1 stained for the neural marker Nestin and the neuronal marker TUJ-1. (E) shows cells in p3 stained for the neural marker Nestin and the neuronal marker TUJ-1. Arrows point towards axons extending from neurons. There are more neurons present in (E) than in (D). Magnification 10×.
Figure 66:
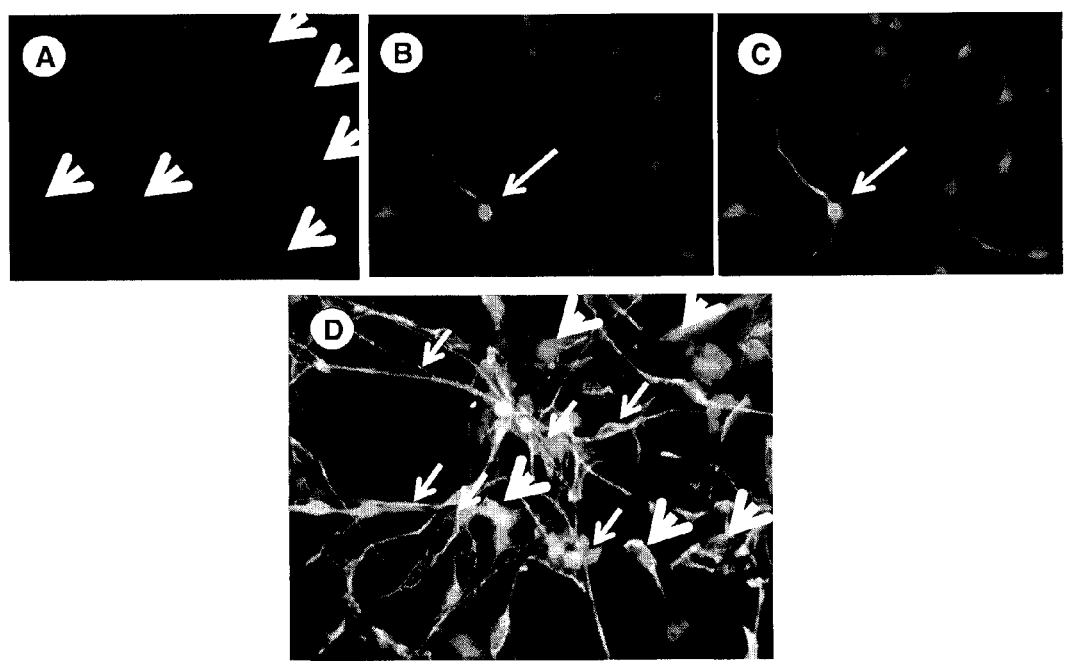
FIG. 66 shows spontaneously differentiated neurons derived from NPCs co-stained for the pan-neuronal marker TUJ-1 (marked by short, thick arrows) (A) and the GABAergic neuron marker GABA (arrow) (B). (C) shows an overlap of TUJ-1 and GABA staining and shows that not all neurons are GABAergic neurons. The arrow in (B) and (C) marks a positive GABAergic neuron. (D) GFAP positive cells (thick arrows), indicating the presence of astrocytes can also be identified in spontaneously differentiated of NPCs. Neurons staining positive for TUJ-1 do not co-stain for GFAP (thin arrows). Magnification 40×.

Example 57. Spontaneous Differentiation of Neural Progenitor Cells (NPCs) into Neurons and Astrocytes Neural progenitor cells were passaged for several passages as described in Example 55 containing a mixture of NPCs, neurons and astrocytes. In this example EBs containing 2000 cells per EB were formed form hESC line H9 p36 in AggreWell™ 800 as described in Example 30. EBs were released and plated as described in Example 31 for 5 days. Next, attached cells were dissociated with HBSS as described in Example 52 and passaged. Cells were cultured for 8 days (Passage 1), dissociated with HBSS as described in Example 55 and passaged into the second passage. Cells were cultured for a further 5 days and then dissociated with TrypIE (third passage). FIG. 65 shows NPCs at passage 1 day 8 (p1d8), p2d2 and p3d3. In passage 1 and 2 mostly NPCs were observed, while in passage 3 sub-populations of neurons emerged spontaneously. For example, FIG. 66 shows cells expressing markers for gabaergic neurons. GFAP positive cells, indicating the presence of astrocytes can also be identified in spontaneously differentiation of NPCs.

Figure 67:
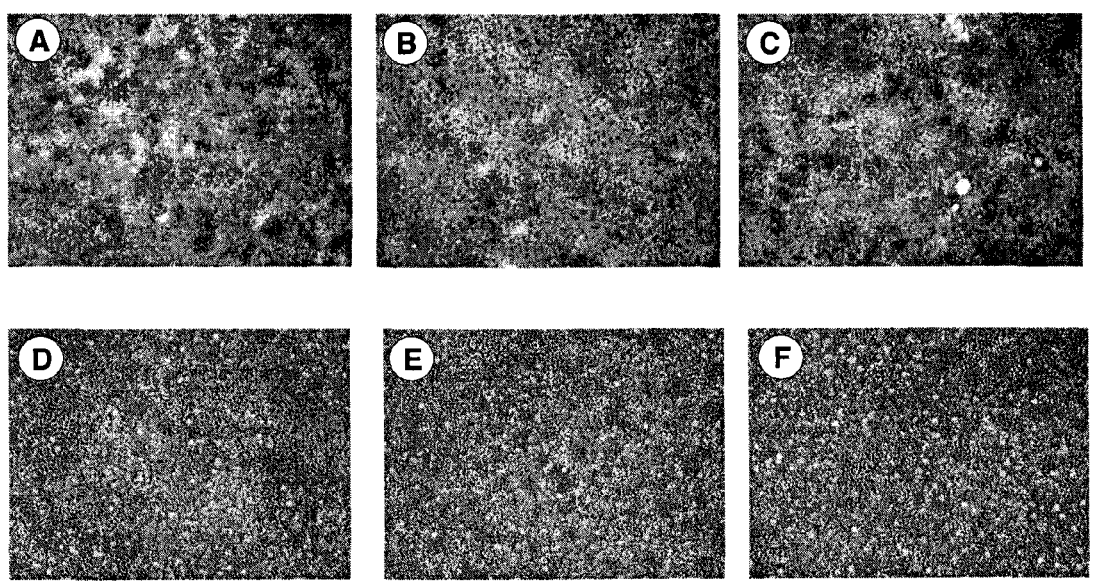
FIG. 67 shows neural induction from hESC line H9 passage 55, passaged for 4 passages as single cell suspension. Adherent NPC cultures 7 days after neuroectoderm induction in mTeSR™ 1-F 270 mOsm/kg (A, D), mTeSR™ 1-F 270 mOsm/kg supplemented with 1% N2A, 1% B27 (B, E) or mTeSR™ 1-F 270 mOsm/kg supplemented with 2% B27 on matrigel. Magnification 2× (A-C), 10× (D-F).

Example 58. Efficient Induction of Neural Ectoderm in hPSCs Cultured in Adherent Culture in mTeSR™ 1-F with an Osmolality of 270 mOsm/kg with and without Supplements The human embryonic stem cell line H9 was passaged as single cells in culture for 4 passages between passage 51 to passage 55 (p51 to p55) as described in Example 21. $1.7 \times 10^5$ cells were plated into a 6-well dish in mTeSR™ 1-F with an osmolality of 270 mOsm/kg alone or supplemented with 2% B27, 1% N2A or 1% B27 (Invitrogen, catalog number 17504-044). Matrigel and Poly-L-ornithine were used for adherent cultures of hPSCs prior and during neural induction. To a person skilled in the art, neural rosettes were apparent as early as 3 days after plating and induction. FIG. 67 shows induced rosette structures 7 days after plating them in induction medium (mTeSR™ 1-F with an osmolality of 270 mOsm/kg) onto matrigel.

Example 59. Culture of Human Pluripotent Stem Cells as Aggregates in Defined Serum-Free Medium on BD Matrigel™ Coating Human pluripotent cells were maintained on BD Matrigel™ coated dishes in defined, low osmolality serum-free medium. A detailed protocol can be found in manual #29267 "Maintenance of Human Embryonic Stem Cells in TeSR™-E8™" by STEMCELL TECHNOLOGIES INC. for the maintenance of human pluripotent stem cells which includes the procedure for BD Matrigel coating. Cells were passaged when the colonies were large, beginning to merge, and had centers that are dense and phase-bright compared to their edges (see FIG. 68). Depending on the size and density of seeded aggregates, cultures were passaged 4-7 days after initial seeding.

Medium was aspirated from the stem cell culture and cells were rinsed with DMEM/F-12 (2 mL/well). 1 mL of Gentle Cell Dissociation Reagent (STEMCELL TECHNOLOGIES INC. catalogue #07174) was added per well. The dish was placed at room temperature (15-25 C) for 6-8 minutes.

Gentle Cell Dissociation Reagent was removed, and 1 mL/well of TeSR™-E8™ was added to the well. Colonies were detached by scraping with a serological glass pipette or a cell scraper (e.g. Corning Catalog #3010 or Fisherbrand Catalog #08-100-240).

The detached cell aggregates were transferred to a 15 mL conical tube and the well was rinsed with an additional 2 mL of TeSR™-E8™ to collect any remaining aggregates. The rinsed media containing remaining cells was added to the same 15 mL tube.

The aggregates within the 15 mL tube were passed through a 2 mL serological pipette 2-5 times to break up the aggregates into a desirable size for replating. A split ratio of 1-10 to 1-40 was performed based on the density of the starting culture at the time of passage.

hESC aggregates were plated with 2 mL of TeSR™-E8™ per new 6-well coated with BD Matrigel™. The plate was moved in several quick, short, back-and-forth and side-to-side motions to disperse cells evenly across the surface of the wells. The plate was placed in a 37° C. incubator. hESCs cultured in TeSR™-E8™ and BD Matrigel™ can be used as a consistent source of cells for the differentiation protocols in this disclosure.

Example 60. Morphological Assessment of Pluripotency of Human Pluripotent Stem Cells (hPSCs) Grown in TeSR™-E8™ on BD Matrigel™

Figure 68:
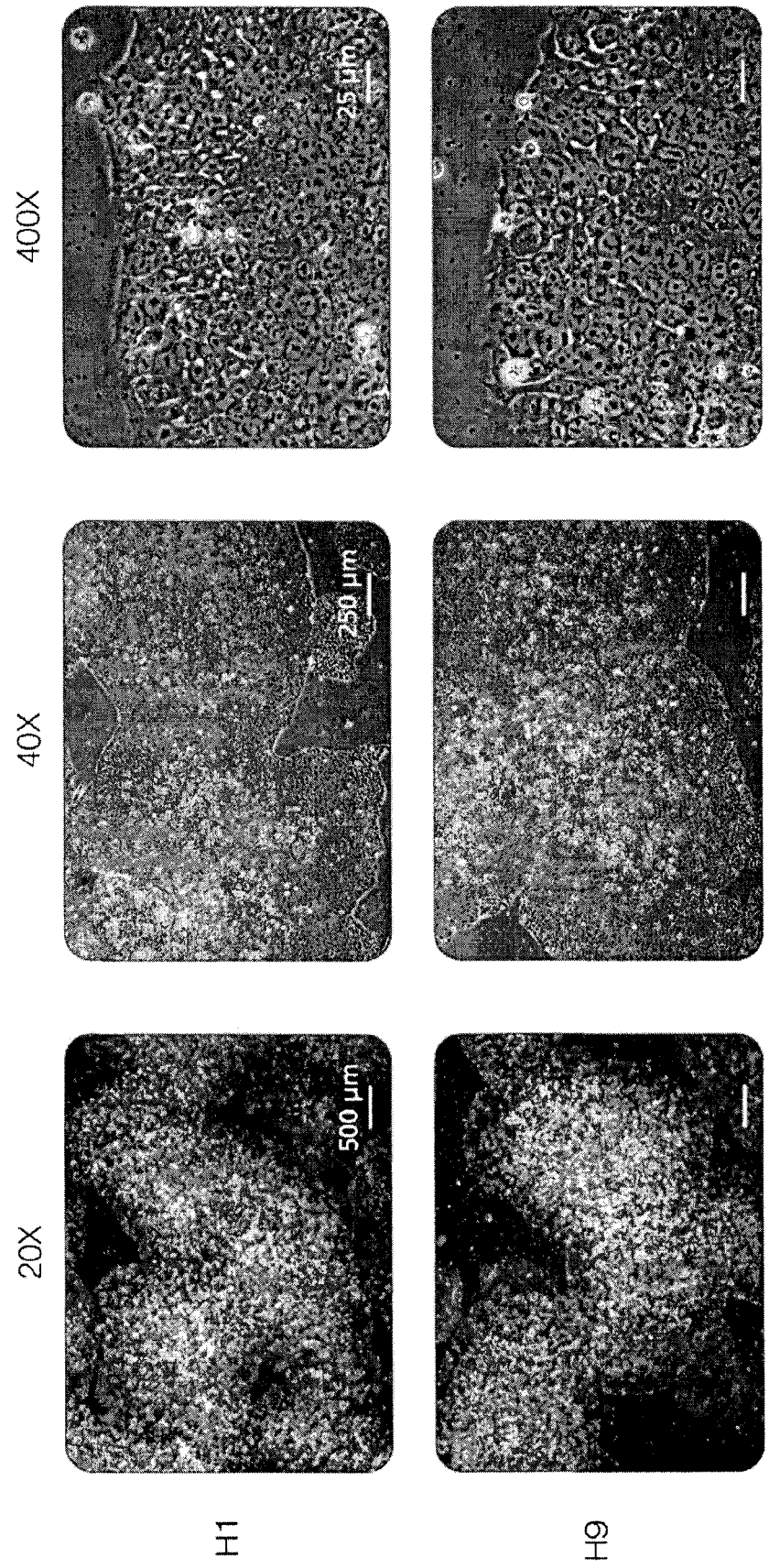
FIG. 68 shows the gross morphology of undifferentiated human embryonic stem cells (H1 and H9 lines) at the optimal time for passaging. These cells have been maintained in TeSR™-E8™ on BD Matrigel™. Images are shown at 20×, 40×, and 400× magnifications.
Figure 69:
FIG. 69 shows example areas of spontaneous differentiation that can occur in pluripotent stem cells cultured in TeSR™-E8™ on BD Matrigel™. Images of differentiation within these H1 cells are circled in the 20× and 40× magnification images. The 400× image shows a close-up area where cells no longer exhibit the characteristic pluripotent stem cell morphology.
Figure 69:
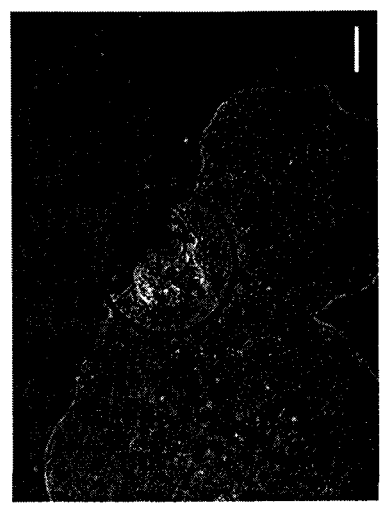
Figure 69:

For the successful induction of endoderm, a highly pure population of pluripotent stem cells was used. The following criteria were employed to assess the morphology and quality of cells (described in technical manual #29267 by STEMCELL TECHNOLOGIES INC.): Undifferentiated human pluripotent stem cells, grew as compact, multi-cellular colonies, as shown in FIG. 68. They exhibited a high nuclear-to-cytoplasm ratio and prominent nucleoli. These colonies were characterized by a distinct border. Healthy hPSC colonies were multilayered in the center, resulting in clusters of phase-bright cells when viewed under phase contrast. Differentiation was characterized by loss of border integrity, gross non-uniform cell morphology within the colony and the emergence of obvious alternate cell types. The percentage of pluripotency was estimated by observation of the colonies under the microscope (using 4× and 10× objectives). Cells were used for germ layer induction only when they displayed less than 10% of differentiation. FIG. 69 shows an example of spontaneous differentiation within TeSR™-E8™ cultured pluripotent stem cells on Matrigel™.

Example 61. Media Formulations with Different Osmolality Ranges: TeSR™-E8™ Medium with Modified Osmolalities The complete media formulation and method of preparation for TeSR™-E8™ (STEMCELL TECHNOLOGIES INC., catalogue #05840) is published in Beers et al, Nature Protocols 7(11): 2029, 2012. It is based on the original E8 formulation published in Chen et al., Nature Methods 8(5): 424, 2011.

Figure 70:
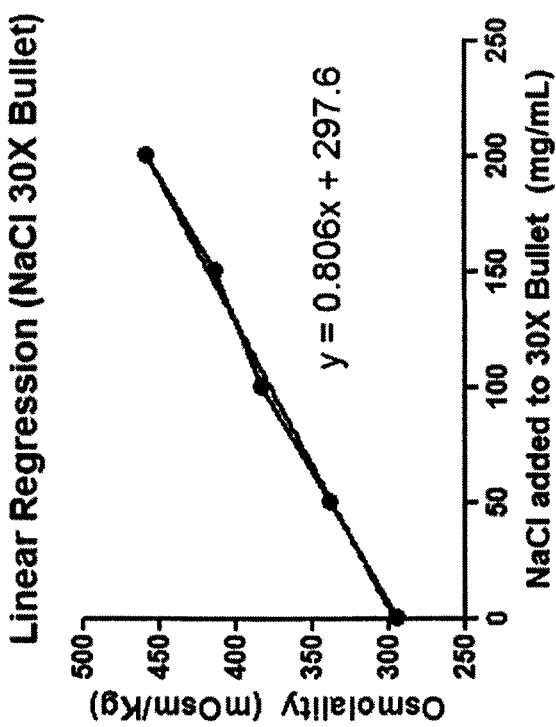
FIG. 70 shows linear regression analysis for the amount of sodium chloride that must be added either (A) directly to TeSR™-E8™ or (B) into a 33× concentrated supplement in order to achieve a desired final osmolality of TeSR™-E8™.
Figure 70:
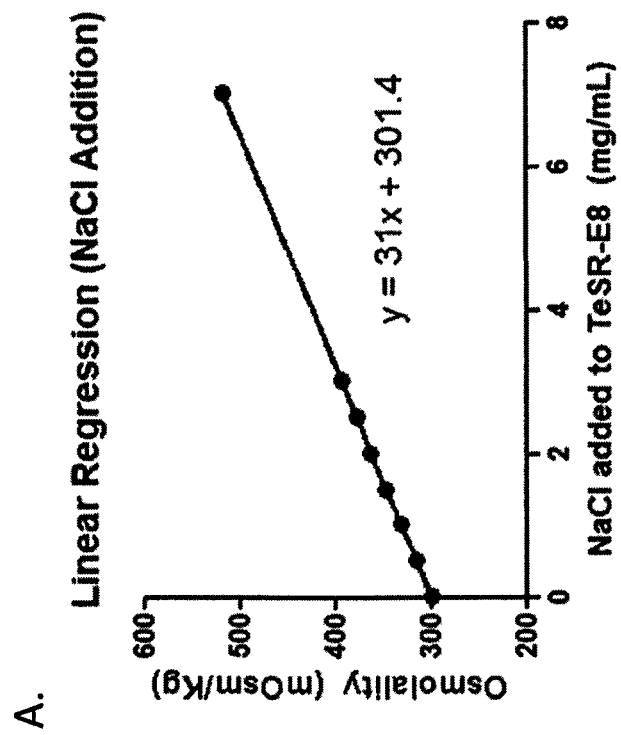

TeSR™-E8™ has an osmolality of approximately 300 mOsm/Kg as measured by a standard osmometer. The osmolality of TeSR™-E8™ was increased by adding sodium chloride to complete TeSR™-E8™ medium. Nine media with different osmolalities were prepared: 300 mOsm/kg (no additional NaCl added to TeSR-E8), 317 mOsm/kg, 332 mOsm/kg, 349 mOsm/kg, 365 mOsm/kg, 379 mOsm/kg, 394 mOsm/kg, 426 mOsm/kg, and 518 mOsm/kg. These media were prepared by adding 0.5 mg/mL, 1.0 mg/mL, 1.5 mg/mL, 2.0 mg/mL, 2.5 mg/mL, 3.0 mg/mL, 4.0 mg/mL, and 7.0 mg/mL, respectively. The amount of NaCl to add to TeSR™-E8™ can be calculated based on the best-fit linear progression as shown in FIG. 70A. As shown in FIG. 70B, a 33× concentrated bullet can be prepared such that 30 μl of this bullet can be added per mL of TeSR™-E8™ to achieve a known final osmolality.

Example 62. Generating a Single Cell Suspension of Human Pluripotent Stem Cells for Direct Plating or for Use in the Formation of Aggregates The procedure for the generation of single human pluripotent stem cells can be found in detail in the product information sheet for STEMdiff™ Definitive Endoderm (STEMCELL Technologies, Inc., Cat #05110; document #29550, 2012). Briefly, human pluripotent stem cell cultures that are ready to be passaged as described herein are washed once with calcium and magnesium-free phosphate buffered saline. This wash solution is aspirated from the culture well and replaced with 1 mL per well of Gentle Cell Dissociation Reagent. The cells are incubated at 37 C for 8-10 minutes until they can be easily detached from the plate by gentle tapping on the culture dish. The cells are dislodged by pipetting the suspension up and down 1-3 times using a p1000 pipette tip. The cells are then immediately transferred to a 15 mL conical tube containing an equal volume of DMEM/F12 medium. Remaining cells are collected using an additional wash of each well with DMEM/F12. The cells are centrifuged at 300×g for 5 minutes to produce a cell pellet. The cell pellet is then re-suspended in the media described in Example 3 also containing 10 uM Y27632 and plated into either culture plates or microwell plates for the generation of a monolayer or aggregate culture, respectively.

Figure 71:
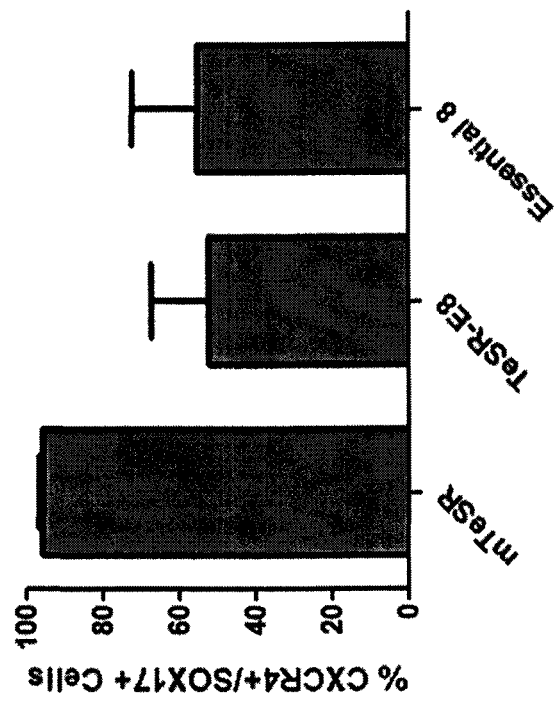
FIG. 71 shows low efficiency definitive endoderm differentiation of human induced pluripotent stem cells (WLS-4D1) previously cultured in either TeSR™-E8™ or Essential 8™ compared to cells previously cultured in mTeSR™ 1. Pluripotent cells were harvested as single cells, resuspended in the same pluripotency medium with 10 μM Y27632 and plated onto Matrigel™-coated 12-well culture plates at a density of 800,000 cells per well. The cells were cultured in their respective pluripotency media with Y27632 for 16-24 hours prior to differentiating the cells to definitive endoderm using STEMdiff™ Definitive Endoderm. Cells were analyzed for expression of CXCR4 and SOX17 by flow cytometry on day 4 of the protocol.

Example 63. Poor Differentiation to Definitive Endoderm in Pluripotent Stem Cells Previously Cultured in Low Osmolality Maintenance Media Separate human pluripotent stem cell (WLS-4D1) cultures were maintained in either mTeSR™ 1, TeSR™-E8™, or Essential 8™ for at least 2 passages. Single cell suspensions were generated from these cultures using methods described herein. The cells were resuspended in their respective maintenance media+10 µM Y27632 and plated into Matrigel-coated 12-well culture plates at a density of 800,000 cells per well. The cells were incubated in these media for 24 hours then differentiated to definitive endoderm using the STEMdiff™ Definitive Endoderm Kit as described herein. On day 5 of the protocol, the cultured cells were harvested as a single cell suspension using a 5 minute, 37 C incubation in the presence of Accutase and the expression of CXCR4 and SOX17 was measured using flow cytometry techniques. FIG. 71 shows results indicating that following 5 days of differentiation in STEMdiff™ Definitive Endoderm medium, cells derived from pluripotent stem cells cultured in TeSR™-E8™ or Essential 8™ differentiated to definitive endoderm with poor efficiency, while those cells derived from pluripotent stem cells previously cultured in mTeSR™ 1 differentiated to definitive endoderm with high efficiency.

Figure 72:
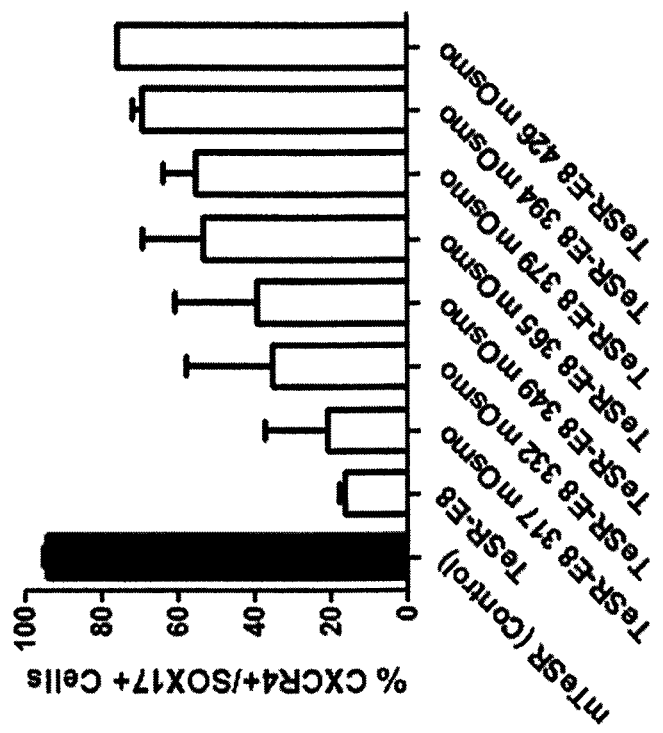
FIG. 72 shows the correlation between increasing osmolality and increasing definitive endoderm differentiation efficiency in the human induced pluripotent stem cell line A13700. The A13700 cells previously maintained in TeSR™-E8™ were harvested as single cells using methods described herein and plated at a density of 800,000 cells into Matrigel-coated 12-well plates. The cells were subjected to a 24-hour incubation in TeSR™-E8™ with the indicated adjusted osmolalities prior to being differentiated to definitive endoderm using the STEMdiff™ Definitive Endoderm Kit. CXCR4/SOX17 co-expression was analyzed on Day 5 of the protocol.

Example 64. Increasing Efficiency of Endoderm Differentiation in Cells Previously Cultured in Low Osmolality Pluripotency Media by Increased Osmolality Treatment Single cell suspensions were generated from the human induced pluripotent stem cell line A13700 (Invitrogen Cat #A13700) using methods described herein. The cells were resuspended in TeSR™-E8™+10 uM Y27632 with osmolalities ranging from 300 to 426 mOsm/Kg and plated into 12-well culture plates at a density of 800,000 cells per well. The cells were incubated in these media for 24 hours then differentiated to definitive endoderm using the STEMdiff™ Definitive Endoderm Kit as described herein. On day 5 of the protocol, the cultured cells were harvested as a single cell suspension using a 5 minute, 37° C. incubation in the presence of Accutase and the expression of CXCR4 and SOX17 was measured using flow cytometry techniques. FIG. 72 shows results from 3 separate experiments indicating that following 5 days of differentiation in STEMdiff™ Definitive Endoderm medium, cells pretreated with the highest osmolality (426 mOsm/Kg) achieved the highest level of expression of definitive endoderm markers. Note that definitive endoderm marker expression data was not generated for cells pretreated with TeSR™-E8™ at 518 mOsm/Kg as this condition resulted in substantial loss of cells via detachment and possibly death.

Figure 73:
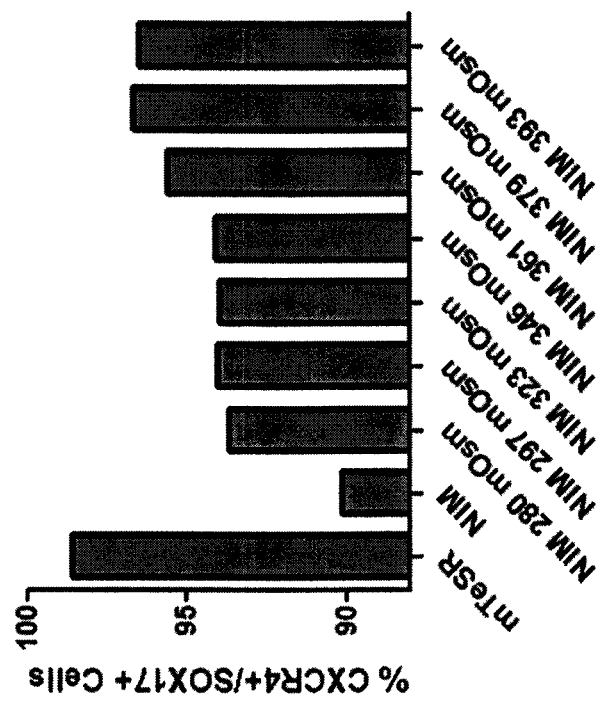
FIG. 73 shows the effect of priming pluripotent stem cells previously cultured in mTeSR™ 1 with STEMdiff™ Neural Induction Medium with increasing adjusted osmolalities for 24 hours prior to initiated differentiation using the STEMdiff™ Definitive Endoderm Kit. CXCR4/SOX17 co-expression was analyzed on Day 5 of the protocol.

Example 65. Increasing Efficiency of Endoderm Differentiation in Cells Previously Cultured in High Osmolality Pluripotency Medium by Adjusting to Higher Osmolality Conditions Single cell suspensions were generated from the human embryonic stem cell line H1 that had been maintained in mTeSR™ 1 using methods described herein. The cells were re-suspended in STEMdiff™ Neural Induction Medium (NIM; STEMCELL Technologies, Inc., Cat #05831 2011)+ 10 µM Y27632 with osmolalities ranging from 280 to 393 mOsm/Kg and plated into 12-well culture plates at a density of 800,000 cells per well. The cells were incubated in these media for 24 hours then differentiated to definitive endoderm using the STEMdiff™ Definitive Endoderm Kit as described herein. On day 5 of the protocol, the cultured cells were harvested as a single cell suspension using a 5 minute, 37 C incubation in the presence of Accutase and the expression of CXCR4 and SOX17 was measured using flow cytometry techniques. FIG. 73 shows that following 5 days of differentiation in STEMdiff™ Definitive Endoderm medium, cells pretreated with the highest osmolality (393 mOsm/Kg) achieved the highest level of expression of definitive endoderm markers.

Figure 74:
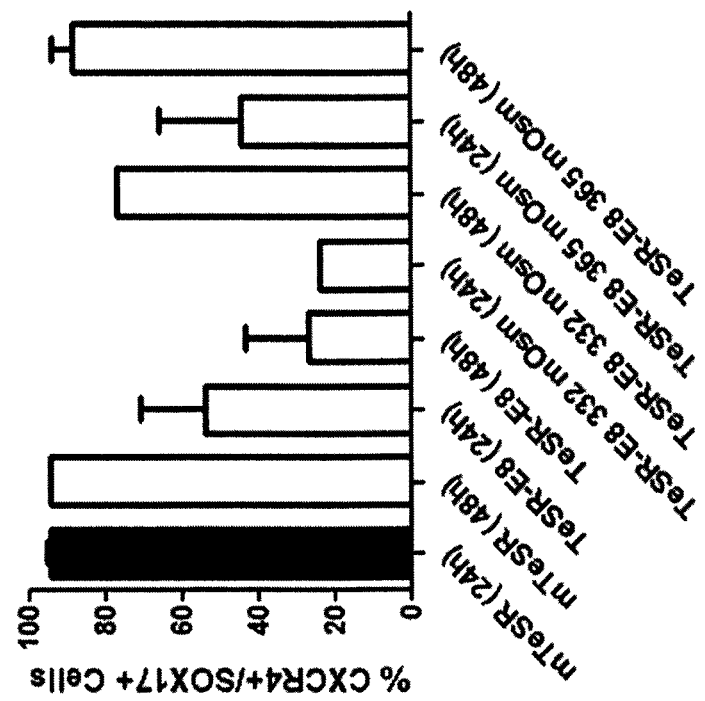
FIG. 74 shows the combined effect of pretreating pluripotent stem cells with high osmolality medium for increasing periods of time prior to initiating definitive endoderm differentiation. WLS-4D1 human induced pluripotent stem cells were previously maintained in either mTeSR™ 1 or TeSR™-E8™. Pluripotent stem cells were harvested as single cells and plated onto Matrigel™ at a density of 800,000 cells per 12-well plate well. mTeSR™ 1 cultures were primed for 24 or 48 hours in monolayer culture using mTeSR™ 1 with 10 µM Y27632. TeSR™-E8™ cultures were primed for 24 or 48 hours in monolayer culture in TeSR™-E8™ media with indicated osmolalities and 10 µM Y27632. CXCR4/SOX17 co-expression was analyzed on Day 5 of the protocol.

Example 66. Increase Endoderm Differentiation Efficiency with 48 h Pretreatment in High Osmolality Compared to 24 h or 8 h Pretreatment in High Osmolality Single cell suspensions were generated from the human induced pluripotent stem cell line WLS-4D1 (Developed in the lab of Bill Stanford, University of Ottawa) that had been maintained in TeSR™-E8™ medium using methods described herein. The cells were re-suspended in TeSR™-E8™+10 µM Y27632 with osmolalities of 300 (standard), 332 mOsm/Kg, or 365 mOsm/Kg and plated into 12-well culture plates at a density of 800,000 cells per well. The cells were incubated in these media for 24 or 48 hours then differentiated to definitive endoderm using the STEMdiff™ Definitive Endoderm Kit as described herein. Cells were harvested as a single cell suspension using a 5 minute, 37 C incubation in the presence of Accutase on either day 4 or day 5 of the protocol and the expression of CXCR4 and SOX17 was measured using flow cytometry techniques. FIG. 74 shows that definitive endoderm formation was most efficient when cells were pretreated for 48 hours with 365 mOsm/Kg TeSR™-E8™ prior to 5 day differentiation using STEMdiff™ Definitive Endoderm. The efficiency of differentiation after 48 h pretreatment with 365 mOsm/Kg TeSR™-E8™ was reduced if cells were harvested after only 4 days of definitive endoderm differentiation (data not shown). The efficiency of differentiation was also reduced if pluripotent stem cells were pretreated with 365 mOsm/Kg for 24 hours prior to 5 day differentiation in STEMdiff™ Definitive Endoderm. Extending the pretreatment period of mTeSR™ 1-cultured cells using mTeSR™ 1 did not affect differentiation efficiency.

Example 67. Use of TGF-Beta Inhibitors to Induce Endoderm Differentiation

Figure 75:
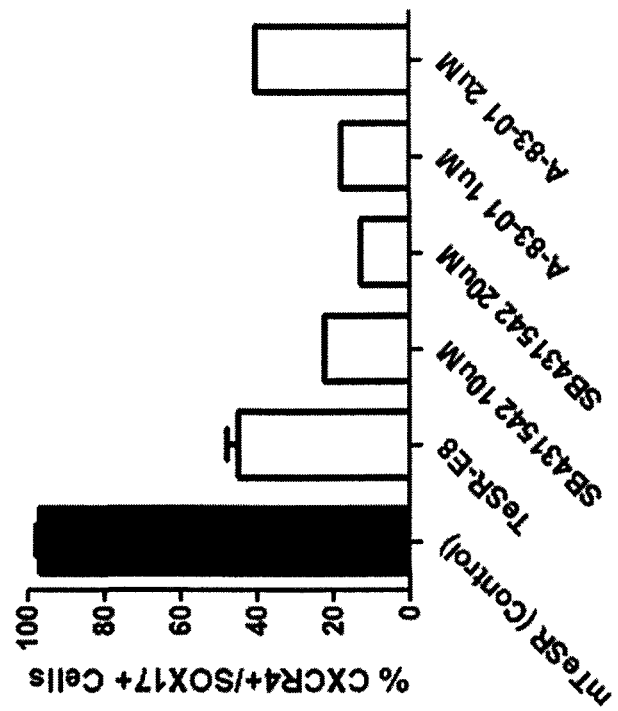
FIG. 75 shows the effect of priming (A) A13700 human induced pluripotent stem cell or (B) H1 human embryonic stem cell TeSR™-E8™ cultures with TeSR™-E8™ plus indicated concentrations of the indicated small molecule TGF-beta inhibitor. CXCR4/SOX17 co-expression was analyzed on Day 5 of the protocol. A standard differentiation using pluripotent stem cells previously cultured in mTeSR™ 1 is shown as a positive control.
Figure 75:
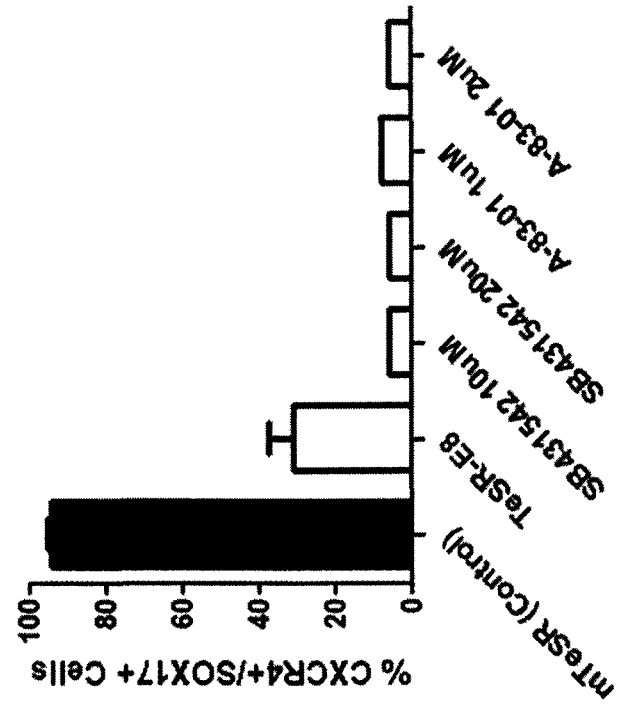

Single cell suspensions were generated from the human induced pluripotent stem cell line A13700 or the human embryonic stem cell line H1 that had been maintained in TesR™-E8™ using methods described herein. The cells were re-suspended in TeSR™-E8™ containing small molecule TGF-beta inhibitors and 10 µM Y-27632 and plated at 800,000 cells per well into Matrigel-coated 12-well culture plates. The TFG-beta inhibitors used were SB431542 at 10 µM or 20 µM, and A-83-01 at 1 µM or 2 µM. Following approximately 16 hours of culture in these media, the cells were differentiated to definitive endoderm using the STEMdiff™ Definitive Endoderm Kit. Following 5 days of differentiation, cells that had been treated with TGF-beta inhibitors did not differentiate with high efficiency to definitive endoderm (FIG. 75).

Figure 76:
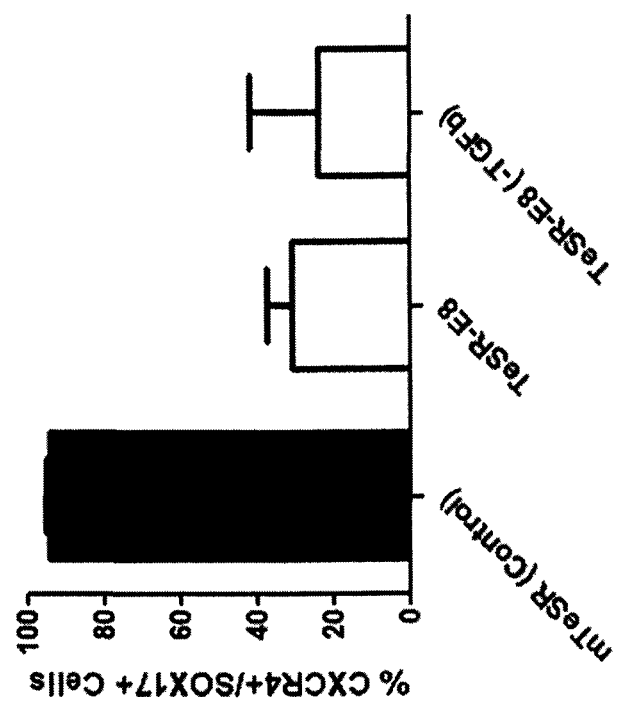
FIG. 76 shows that removal of TGF-beta from TeSR™-E8™ during a 24 hour priming of the human induced pluripotent stem cell line A13700 has no effect on definitive endoderm differentiation efficiency. A standard differentiation using pluripotent stem cells previously cultured in mTeSR™ 1 is shown as a positive control.

Example 68. Using TeSR-E8 without TGF-Beta Based Medium to Induce Endoderm Differentiation Single cell suspensions were generated from the human induced pluripotent stem cell line A13700 that had been maintained in TeSR™-E8™ using methods described herein. The cells were re-suspended in TeSR™-E8™ wherein TGF-beta had been removed, then plated at 800,000 cells per well into Matrigel-coated 12-well culture plates. Following approximately 16 hours of culture in this medium, the cells were differentiated to definitive endoderm using the STEMdiff™ Definitive Endoderm Kit. Following 5 days of differentiation, cells that had been treated with TGF-beta-free TeSR™-E8™ did not differentiate with high efficiency to definitive endoderm (FIG. 76).

Figure 77:
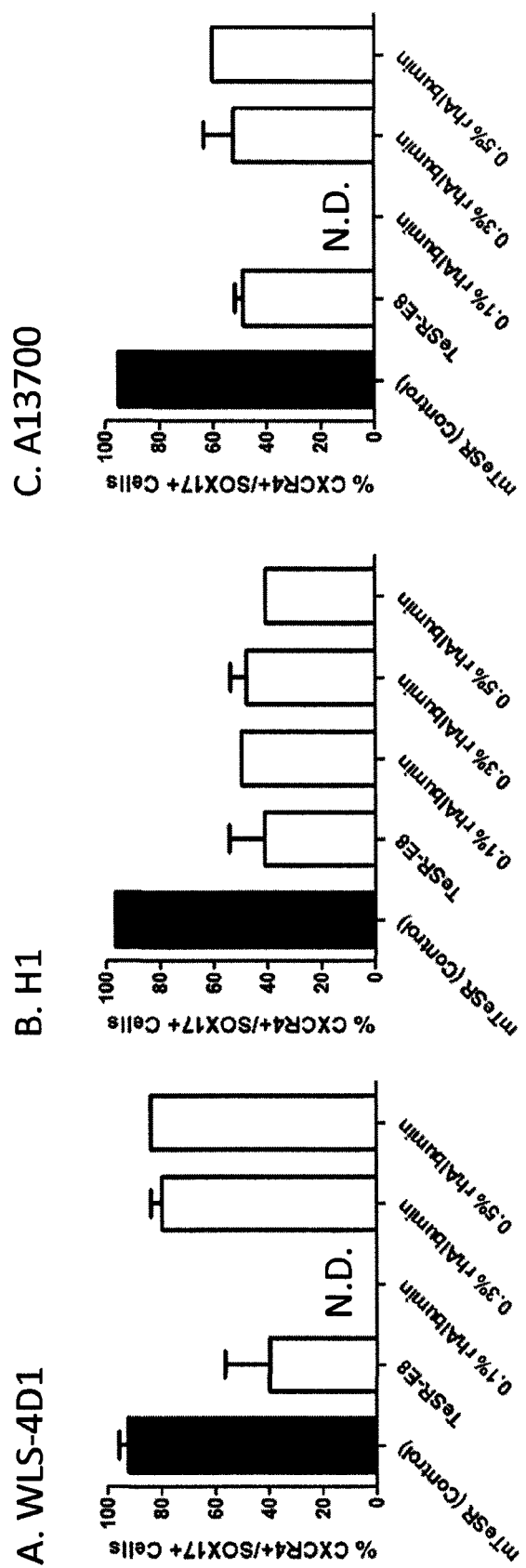
FIG. 77 shows that addition of recombinant human albumin (rhAlbumin) to TeSR™-E8™ during a 24 hour priming period results in improved differentiation efficiency to definitive endoderm in the WLS-4D1 human induced pluripotent stem cells line (FIG. 77A) but not in the human embryonic stem cell line H1 (FIG. 77B) or the human induced pluripotent stem cell line A13700 (FIG. 77C). A standard differentiation using pluripotent stem cells previously cultured in mTeSR™ 1 is shown as a positive control for each cell line.

Example 69. Use of Protein Such as Albumin to Induce Endoderm Differentiation Single cell suspensions were generated from the human embryonic stem cell line H1 or the human induced pluripotent stem cell lines WLS-4D1 or A13700 that had been maintained in TeSR™-E8™ using methods described herein. The cells were re-suspended in TeSR™-E8™ with different concentrations of human recombinant albumin (0.1%, 0.3%, or 0.5%), then plated at 800,000 cells per well into Matrigel-coated 12-well culture plates. Following approximately 16 hours of culture in this medium, the cells were differentiated to definitive endoderm using the STEMdiff™ Definitive Endoderm Kit. Following 5 days of differentiation, only the WLS-4D1 cell line showed improved differentiation efficiency when primed with TeSR™-E8™ with albumin (FIG. 77A). The other two cell lines did not differentiate with high efficiency to definitive endoderm when primed with TeSR™-E8™ with albumin at any of the tested concentrations (FIG. 77B, C).

Example 70. Clump Cultures

Figure 78:
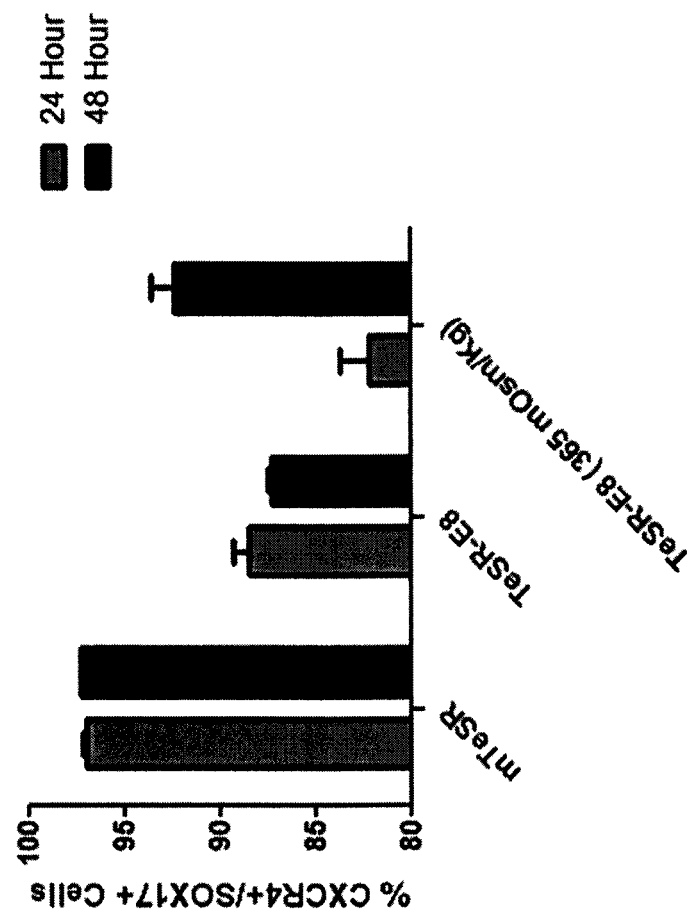
FIG. 78 shows the effect of 24 or 48 hour priming of TeSR™-E8™ clump cultures with either standard osmolality TeSR™-E8™ or TeSR™-E8™ with osmolality adjusted to 365 mOsm/Kg.

Clumps or aggregates (approximately 100-200 µm in diameter) were generated from the human embryonic stem cell line H1 that had been maintained in mTeSR™ 1 or TeSR™-E8™ using methods described herein. The clumps were re-suspended in mTeSR™ 1 or TeSR™-E8™ (either standard osmolality or osmolality adjusted to 365 mOsm/Kg), then plated at 1000 clumps per well into Matrigel-coated 12-well culture plates. Following either 24 or 48 hours of culture in these media, the cells were differentiated to definitive endoderm using the STEMdiff™ Definitive Endoderm Kit. Following 5 days of differentiation, clumps previously cultured in mTeSR™ 1 differentiated to definitive endoderm with high efficiency. For clumps previously maintained in TeSR™-E8™, plating the clumps into low osmolality TeSR™-E8™ for 24 or 48 hours prior to definitive endoderm differentiation resulted in poorer differentiation compared to those clumps previously maintained in mTeSR™ 1. A 24 hour pretreatment of clumps previously maintained in TeSR™-E8™ with TeSR™-E8™ at 365 mOsm/Kg did not improve differentiation efficiency; however, extending this pretreatment in TeSR™-E8™ at 365 mOsm/Kg to 48 hours resulted in an improved efficiency of differentiation to definitive endoderm (FIG. 78).

Figure 79:
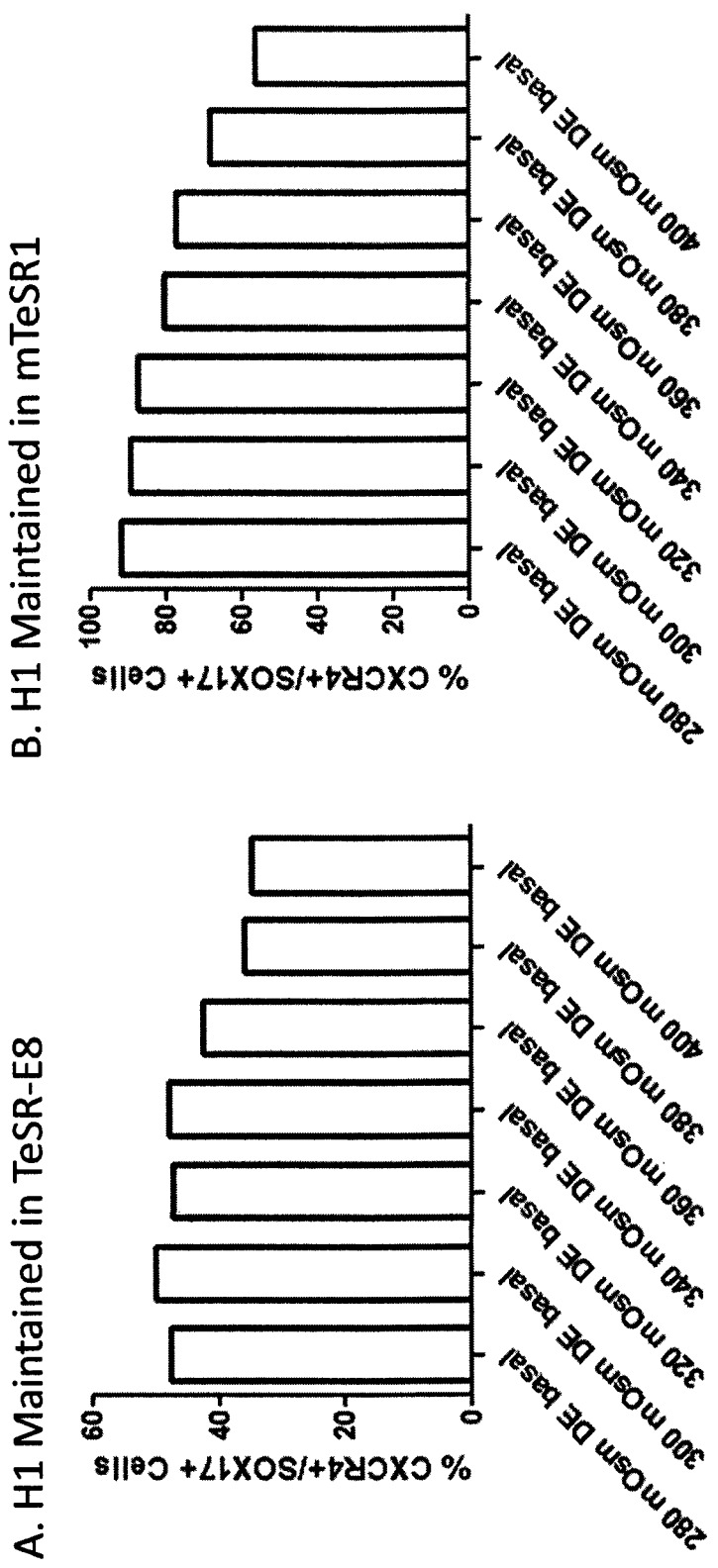
FIG. 79 shows the effect of modulating the osmolality of the culture medium used during the differentiation to definitive endoderm in the H1 human embryonic stem cell line previously maintained in (A) TeSR™-E8™ or (B) mTeSR™ 1.

Example 71. Increasing Osmolality of the Differentiation Basal Medium does not Improve Differentiation Efficiency Single cell suspensions were generated from the human embryonic stem cell line H1 that had been maintained in mTeSR™ 1 or TeSR™-E8™ using methods described herein. The cells were re-suspended in the same maintenance medium (osmolality not adjusted from standard) with 10 µM Y27632, then plated at 800,000 cells per well into Matrigel-coated 12-well culture plates. Following approximately 16 hours of culture in this medium, the cells were differentiated to definitive endoderm using the STEMdiff™ Definitive Endoderm Kit with the following modification. The osmolality of the STEMdiff™ Definitive Endoderm Basal Medium (STEMCELL Technologies, Inc., Cat #05111) was modified using addition of sodium chloride to the following osmolalities: 300 mOsm/Kg, 320 mOsm/Kg, 340 mOsm/Kg, 360 mOsm/Kg, 380 mOsm/Kg, and 400 mOsm/Kg. Following 5 days of differentiation, cells that had been treated with higher osmolality STEMdiff™ Definitive Endoderm Basal Medium differentiated with lower efficiency to definitive endoderm compared to those cells cultured in lower osmolality STEMdiff™ Definitive Endoderm Basal Medium (FIG. 79).

Discussion:

Alterations in osmolality can affect cell size, thus potentially activating stretch or mechanical force-regulated signaling pathways. One such pathway thought to be regulated by stretch is the Wnt/B-Catenin pathway. The Wnt/B-Catenin pathway plays a critical role in the early formation of the primitive streak, the precursor of endoderm (Zorn and Wells 2009). Activation of Wnt, or inhibition of GSK-3, a downstream wnt effector protein results in the differentiation of human pluripotent stem cells towards the primitive streak and endoderm. Most in vitro protocols for the differentiation of human pluripotent stem cells towards endoderm utilize either a Wnt activator, eg. Wnt3a (D'Amour et al., 2006; Rezania et al., 2011, 2012) or an inhibitor of GSK-3 (eg. US2009/0298178A1). Culturing human pluripotent stem cells in a low osmolality environment may keep Wnt signaling low, thus keeping the cells in a state from which differentiation to endoderm is more difficult. Conversely, it could be postulated that culturing human pluripotent stem cells in a medium with higher osmolality, which may activate a specific stretch or mechanical force correlated to a partial activation of the wnt pathway, may provide a faster, more specified, or more efficient differentiation to endoderm in these cells.

Recently, several low-protein media have been developed for the maintenance of human pluripotent stem cells in an undifferentiated state. These include, but are not limited to E8 (Chen et al., MatMethods, 2011; Beers et al, Nat Protoc, 2012), Essential 8™ (Life Technologies), and TeSR™-E8™ (STEMCELL). Among the key differences between E8 and more common pluripotency media, including mTeSR™ 1, is a much reduced concentration of proteins (433 fold less protein in E8 compared to mTeSR), largely resulting from E8 being substantially free of albumin. Proteins, and albumin in particular, are effective at binding molecules and can therefore reduce the effective concentration or bioavailability of key signaling molecules that might be present within culture media designed to invoke differentiation of human pluripotent stem cells. For example, see Belatik et al., 2012. This suggests that adding albumin back into a formulation such as TeSR™-E8™ such that levels are within a similar range to that found in more traditional pluripotency media formulations should restore the ability of the cells to respond to a standard definitive endoderm differentiation protocol. Different ES or iPS cell lines may be more or less sensitive to concentrations of morphogens or toxins with the differentiation media. The addition of albumin to the medium may buffer toxins or reduce bioavailability of certain morphogens within the medium, thus resulting in differential responses to the protocol described in Example 69.

Another key difference between E8-like formulations and other higher protein maintenance media is the presence of an approximately 4-fold increase in TGF-beta concentrations within the E8-like formulations. Signaling through TGF-beta is critical during the differentiation of human pluripotent stem cells to definitive endoderm. Thus, the present inventors hypothesized that a reduction in TGF-beta signaling may restore the differentiation potential of the human pluripotent stem cells cultured in these E8-like formulations. This was tested in two ways. First, TGF-beta was removed from the TeSR™-E8™ formulation, and undifferentiated cells were cultured in this medium for 24 hours prior to differentiation towards definitive endoderm using the STEMdiff™ Definitive Endoderm Kit (Example 68). This did not result in improved differentiation efficiency. Second, we tested the addition of small molecule TGF-beta inhibitors (Example 67). In these tests, cells previously cultured in TeSR™-E8™ were seeded as a monolayer and incubated in TeSR™-E8™ with or without the TGF-beta inhibitors at multiple concentrations for 24 hours prior to differentiation using STEMdiff™ Definitive Endoderm. This did not result in improved differentiation efficiency. Therefore modification of TGF-beta levels did not directly improve definitive endoderm differentiation of stem cells.

The third fundamental difference between E8-like formulations and those with higher protein levels is a change in the osmolality. E8-like media typically have an osmolality near 300 mOsm/Kg, which is significantly lower than the osmolality of other home-made and commercially available pluripotency media, which are typically near 340 mOsm/Kg (Ludwig et al., 2006). To test the effect of osmolality on the definitive endoderm differentiation potential of human pluripotent stem cells, the present inventors incubated human pluripotent stem cells that had previously been cultured in TeSR™-E8™ for 24 hours in TeSR™-E8™ with osmolality adjusted to 332 mOsm/Kg or 365 mOsm/Kg (Example 66). In both cases, differentiation was then performed using STEMdiff™ Definitive Endoderm. Differentiation potential in both conditions was significantly reduced compared to cells that had been maintained in mTeSR™ 1. Extending the culture period of higher osmolality (either 332 mOsm/Kg or 365 mOsm/Kg) to around 48 hours prior to inducing definitive endoderm differentiation resulted in much improved differentiation efficiency to definitive endoderm. Cells cultured in 365 mOsm/Kg culture medium performed better than those cultured in 332 mOsm/Kg culture medium and their overall efficiency of differentiation was not significantly different from cells that had been maintained in mTeSR™ 1. These finding were unexpected and suggest the manipulation of the osmolality and timing of culture could influence cell fate outcomes.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Plate or Well Size | Target # of Clumps/Plate or Well |
| --- | --- |
| 100 mm dish | 2400 clumps |
| 60 mm dish | 1000 clumps |
| wells in a 6-well dish | 350 clumps |

TABLE 2

| Component | Concentration as 1 x (mg/ml) |
| --- | --- |
| Sodium Bicarbonate | 0.544 |
| L-glutamine | 0.142 |
| Human Holo-transferrin | 0.0106 |
| BSA | 13.1 |
| Thiamine HCl | 0.0064 |
| Reduced glutathione | 1.942 |
| L-ascorbic acid | 0.32 |
| L-alanine | 0.0086 |
| L-asparagine $H_2O$ | 1.456E−03 |
| L-aspartic acid | 1.292E−03 |
| L-glutamic acid | 1.428E−03 |
| Glycine | 7.28E−03 |
| L-proline | 1.116E−03 |
| L-serine | 1.02E−03 |
| 1000 x trace elements B | 1.94 x |
| 1000 x trace elements C | 0.97 x |
| Sodium Selenium | 1.36E−06 |
| Human Insulin | 1.94E−03 |
| Chemically Defined Lipids | 1.942E−03 mL/mL |
| 2Beta Mercapto ethanol | 9.718E−06 |
| NaCl for 260 mOsm/kg | 0.027 |
| NaCl for 270 mOsm/kg | 0.33 |
| NaCl for 290 mOsm/kg | 0.95 |
| NaCl for 320 mOsm/kg | 1.87 |
| NaCl for 340 mOsm/kg | 2.48 |

TABLE 3

| | Required number of cells per well | |
| --- | --- | --- |
| Desired number of cells per EB | AggreWell ™400 each well contains approximately 1200 microwells | AggreWell ™800 each well contains approximately 300 microwells |
| 50 | $6 \times 10^4$ cells | — |
| 100 | $1.2 \times 10^5$ cells | — |
| 200 | $2.4 \times 10^5$ cells | — |
| 500 | $6 \times 10^5$ cells | — |
| 1,000 | $1.2 \times 10^6$ cells | $3.0 \times 10^5$ cells |

TABLE 3-continued

Required number of cells per well

| Desired number of cells per EB | AggreWell ™400 each well contains approximately 1200 microwells | AggreWell ™800 each well contains approximately 300 microwells |
|---|---|---|
| 2,000 | 2.4 × 10$^6$ cells | 6.0 × 10$^5$ cells |
| 3,000 | 3.6 × 10$^6$ cells | 9.0 × 10$^5$ cells |
| 4,000 | — | 1.2 × 10$^6$ cells |
| 5,000 | — | 1.5 × 10$^6$ cells |
| 10,000 | — | 3.0 × 10$^6$ cells |
| 15,000 | — | 4.5 × 10$^6$ cells |
| 20,000 | — | 6.0 × 10$^6$ cells |

TABLE 4

| Component | Concentration |
|---|---|
| DMEM/F12 (Liquid) | N/A |
| L-Ascorbic Acid | 64 mg/L |
| Selenium | 14 µg/L |
| Transferrin | 10.7 mg/L |
| NaHCO$_3$ | 543 mg/L |
| Insulin | 19.4 mg/L |
| FGF2 | 100 µg/L |
| TGF-beta | 2 µg/L |

REFERENCES

Amabile G, Meissner A (2009) Induced pluripotent stem cells: current progress and potential for regenerative medicine. Trends Mol Med. 2009 February; 15(2):59-68. Epub 2009 Jan. 21

Beers et al. (2012) Passaging and colony expansion of human pluripotent stem cells by enzyme-free dissociation in chemically defined culture conditions. Nat Protoc. 7(11):2029-2040.

Belatik et al. (2012) Binding sites of retinol and retinoic acid with serum albumins. Eur J Med Chem. 48:114-123.

Borowiak M, Maehr R, Chen S, Chen A E, Tang W, Fox J L, Schreiber S L, Melton D A (2009) Small molecules efficiently direct endodermal differentiation of mouse and human embryonic stem cells. Cell Stem Cell. April 3; 4(4):348-58

Boyd N L, Robbins K R, Dhara S K, West F D, Stice S L (2009) Human embryonic stem cell-derived mesoderm-like epithelium transitions to mesenchymal progenitor cells. Tissue Eng Part A. 2009 August; 15(8):1897-907

Brewer G J, Torricelli J R, Evege E K, Price P J (1993) Optimized survival of hippocampal neurons in B27-supplemented Neurobasal, a new serum-free medium combination. J Neurosci Res. 1993 Aug. 1; 35(5):567-76.

Brewer G J, Price P J (1996) Viable cultured neurons in ambient carbon dioxide and hibernation storage for a month. Neuroreport. 1996 Jun. 17; 7(9):1509-12

Chambers S M, Fasano C A, Papapetrou E P, Tomishima M, Sadelain M, Studer L (2009) Highly efficient neural conversion of human ES and iPS cells by dual inhibition of SMAD signaling. Nat Biotechnol. 2009 March; 27(3): 275-80. Epub 2009 Mar. 1. Erratum in: Nat Biotechnol. 2009 May; 27(5):485

Chen et al. (2011) Chemically defined conditions for human iPSC derivation and culture. Nat Methods 8(5):424-429.

D'Amour K A, Agulnick A. D., Eliazer, S., Kelly O. G., Kroon E, Baetge E. E (2005) Efficient differentiation of human embryonic stem cells to definitive endoderm. Nat. Biotech. 23:12 1534-1541

D'Amour et al. (2006) Production of pancreatic hormone-expressing endocrine cells from human embryonic stem cells. Nat. Biotech. 24(11): 1392-1401.

Dhara S K, Hasneen K, Machacek D W, Boyd N L, Rao R R, Stice S L (2008) Human neural progenitor cells derived from embryonic stem cells in feeder-free cultures. Differentiation (2008) 76:454-464

Dravid et al., (2006) Culture of human embryonic stem cells on human and mouse feeder cells. Embryonic stem cell protocols, Humana Press Elkabetz Y, Panagiotakos G, Al Shamy G, Socci N D, Tabar V, Studer L (2009) Human ES cell-derived neural rosettes reveal a functionally distinct early neural stem cell stage. Genes Dev. 2008 Jan. 15; 22(2):152-65. Erratum in: Genes Dev. 2008 May 1; 22(9):1257

Elkabetz Y and Studer L (2009) Human ESC-derived Neural Rosettes and Neural Stem Cell Progression. Cold Spring Harb Symp Quant Biol 2008 73: 377-387 originally published online Feb. 9, 2009

Ferreira L S, Gerecht S, Shieh H F, Watson N, Rupnick M A, Dallabrida S M, Vunjak-Novakovic G, Langer R (2007) Vascular progenitor cells isolated from human embryonic stem cells give rise to endothelial and smooth muscle like cells and form vascular networks in vivo. Circ Res. 2007 Aug. 3; 101(3):286-94. Epub 2007 Jun. 14

Gerrard L, Rodgers L, Cui W (2005) Differentiation of Human Embryonic Stem Cells to Neural Lineages in Adherent Culture by Blocking Bone Morphogenetic Protein Signaling. Stem Cells Vol. 23 No. 9 October 2005, pp. 1234-1241

Itsykson P, Ilouz N, Turetsky T, Goldstein R S, Pera M F, Fishbein I, Segal M, Reubinoff B E (2005) Derivation of neural precursors from human embryonic stem cells in the presence of noggin. Mol Cell Neurosci. 2005 September; 30(1):24-36

Jessell T M (2000) Neuronal specification in the spinal cord: inductive signals and transcriptional codes. Nat Rev Genet. 2000 October; 1(1):20-9

Kim D S, Lee J S, Leem J W, Huh Y J, Kim J Y, Kim H S, Park I H, Daley G Q, Hwang D Y, Kim D W (2010) Robust enhancement of neural differentiation from human ES and iPS cells regardless of their innate difference in differentiation propensity. Stem Cell Rev. 2010 June; 6(2):270-81. Erratum in: Stem Cell Rev. 2010 June; 6(2):334.

Kivell B M, McDonald F J, Miller J H (2000) Serum-free culture of rat post-natal and fetal brainstem neurons. Developmental Brain Research 120_2000. 199-210

Kubo L H, Shinozaki K, Shannon J M, Kouskoff V, Kennedy M, Woo S, Fehling H J Keller G (2004) Development of definitive endoderm from embryonic stem cells in culture. Development 131, 1651-1662 (2004)

Koch P, Opitz T, Steinbeck J A, Ladewig J, Brüstle O (2009) A rosette-type, self-renewing human ES cell-derived neural stem cell with potential for in vitro instruction and synaptic integration. Proc Natl Acad Sci USA. 2009 Mar. 3; 106(9):3225-30. Epub 2009 Feb. 13

Lee L H, Peerani R, Ungrin M, Joshi C, Kumacheva E, Zandstra P (2009) Micropatterning of human embryonic stem cells dissects the mesoderm and endoderm lineages. Stem Cell Res. 2009 March; 2(2):155-62. Epub 2008 Dec. 3

Li X J, Du Z W, Zarnowska E D, Pankratz M, Hansen L O, Pearce R A, Zhang S C (2005) Specification of motoneurons from human embryonic stem cells. Nat Biotechnol. 2005 February; 23(2):215-21. Epub 2005 Jan. 30

Ludwig T E, Bergendahl V, Levenstein M E, Yu J, Probasco M D, Thomson J A (2006). Feeder-independent culture of human embryonic stem cells. Nat Methods. 2006 August; 3(8):637-46. Erratum in: Nat Methods. 2006 October; 3(10):867

Ludwig T E, Levenstein M E, Jones J M, Berggren W T, Mitchen E R, Frane J L, Crandall L J, Daigh C A, Conard K R, Piekarczyk M S, Lianas R A, Thomson J A (2006) Derivation of human embryonic stem cells in defined conditions. Nat Biotechnol. 2006 February; 24(2):185-7. Epub 2006 Jan. 1

Mallon B S, Park K Y, Chen K G, Hamilton R S, McKay R D (2006) Toward xeno-free culture of human embryonic stem cells. Int J Biochem Cell Biol. 2006; 38(7):1063-75. Epub 2006 Jan. 23

Mummery C L, Ward D, Passier R (2007) Differentiation of Human Embryonic Stem Cells to Cardiomyocytes by Coculture with Endoderm in Serum-Free Medium. Curr Protoc Stem Cell Biol. 2007 July; Chapter 1: Unit 1F.2

Murry C E, Keller G (2008) Differentiation of embryonic stem cells to clinically relevant populations: lessons from embryonic development. Cell. 2008 Feb. 22; 132(4):661-80. Review Nat R, Nilbratt M, Narkilahti S, Winblad, B, Hovatte, O, Nordberg A (2007) Neurogenic Neuroepithelial and Radial Glial Cells Generated from Six Human Embryonic Stem Cell Lines in Serum-Free Suspension and Adherent Cultures. Glia 55:385-399 (2007)

Odorico J S, Kaufman D S, Thomson J A (2001) Multilineage Differentiation from Human Embryonic Stem Cell Lines. Stem Cells, Vol. 19, No. 3, 193-204, May 2001

Osafune K, Chen A E, Melton D A (2006) Directed Differentiation of Human Embryonic Stem Cells into Early Endoderm Cells. Curr Opin Investig Drugs. 2006 July; 7(7):614-8

Peh G S L, Lang, G J, Pera M F, Hawes S M (2009) CD133 Expression by Neural Progenitors Derived from Human Embryonic Stem Cells and Its Use for Their Prospective Isolation. Stem Cells and Development Volume 18, Number 2

Perrier A L, Tabar V, Barberi T, Rubio M E, Bruses J, Topf N, Harrison N L, Studer L (2004) Derivation of midbrain dopamine neurons from human embryonic stem cells. Proc Nat Acad Sci USA. 2004 Aug. 24; 101(34):12543-8. Epub 2004 Aug. 13

Rezania et al. (2011) Production of functional glucagon-secreting alpha cells from human embryonic stem cells. Diabetes 60:239-247

Rezania et al. (2012) Maturation of human embryonic stem cell-derived pancreatic progenitors into functional islets capable of treating pre-existing diabetes in mice. Diabetes 61:2016-2029

Schuldiner M, Eiges R, Eden A, Yanuka O, Itskovitz-Eldor J, Goldstein R S, Benvenisty N (2001) Induced neuronal differentiation of human embryonic stem cells. Brain Res. 2001 Sep. 21; 913(2):201-5.

Shin S, Mitalipova M, Noggle S, Tibbitts D, Venable A, Rao R, Stice S L (2006) Long-term proliferation of human embryonic stem cell-derived neuroepithelial cells using defined adherent culture conditions. Stem Cells. 2006 January; 24(1):125-38. Epub 2005 Aug. 11

Schulz T C, Palmarini G M, Noggle S A, Weiler D A, Mitalipova M M, Condie B G (2003) Directed neuronal differentiation of human embryonic stem cells. BMC Neurosci. 2003 Oct. 22; 4:27

Sonntag K C, Sanchez-Pernaute R. (2006) Tailoring human embryonic stem cells for neurodegenerative disease therapy. Curr Opin Investig Drugs. 2006 July; 7(7):614-8

Sonntag K C, Pruszak J, Yoshizaki T, van Arensbergen J, Sanchez-Pernaute R, Isacson O (2007) Enhanced yield of neuroepithelial precursors and midbrain-like dopaminergic neurons from human embryonic stem cells using the bone morphogenic protein antagonist noggin. Stem Cells. 2007 February; 25(2):411-8. Epub 2006 Oct. 12

Sulzbacher S, Schroeder I S, Truong T T, Wobus A M (2009) Activin A-induced differentiation of embryonic stem cells into endoderm and pancreatic progenitors—the influence of differentiation factors and culture conditions. Stem Cell Rev Rep. 2009 June; 5(2):159-73. Epub 2009 Mar. 5

Takei S, Ichikawa H, Johkura K, Mogi A, No H, Yoshie S, Tomotsune D, Sasaki K (2009) Bone morphogenetic protein-4 promotes induction of cardiomyocytes from human embryonic stem cells in serum-based embryoid body development. Am J Physiol Heart Circ Physiol 296: H1793-H1803, 2009

Watanabe K, Ueno M, Kamiya D, Nishiyama A, Matsumura M, Wataya T, Takahashi J B, Nishikawa S, Nishikawa S, Muguruma K, Sasai Y (2007) A ROCK inhibitor permits survival of dissociated human embryonic stem cells. Nat Biotechnol. 2007 June; 25(6):681-6. Epub 2007 May 27

Wiese, C, Rolletscheka A, Kaniaa G, Blyszczuka, K V, Tarasovb, Y, Tarasovab, R., Werstob, P, Bohelerb K R, Wobus A M (2004) Nestin expression—a property of multi-lineage progenitor cells? CMLS, Cell. Mol. Life Sci. 61 (2004) 2510-2522

Yan Y, Yang D, Zarnowska E D, Du Z, Werbel B, Valliere C, Pearce R A, Thomson J A, Zhang S C (2007) Directed Differentiation of Dopaminergic Neuronal Subtypes from Human Embryonic Stem Cells. Stem Cells Volume 23 Issue 6, Pages 781-790

Zhang S C, Wernig M, Duncan, I D, Brustle O, Thomson J A (2001) In vitro differentiation of transplantable neural precursors from human embryonic stem cells. Nature Biotechnology 19, 1129-1133 (2001)

Zorn and Wells (2009) Vertebrate endoderm development and organ formation. Annu. Rev. Cell Dev. Biol. 25: 221-251.

The invention claimed is:

1. A method of generating a population of enriched mammalian endodermal progenitor cells comprising: a) maintaining mammalian pluripotent stem cells in a first stem cell medium having an osmolality of 260-310 mOsm/kg; b) priming the mammalian pluripotent stem cells of step a) for endoderm induction by incubating the cells from a) in a second stem cell culture medium having an osmolality of 350 to 550 mOsm/kg for 16 to 60 hours; and c) differentiating the primed mammalian cells from b) in a differentiation medium having an osmolality of 260-310 mOsm/kg to enrich for endodermal progenitor cells;

wherein the mammalian endodermal progenitor cells derived from the mammalian pluripotent stem cells express one or more definitive endoderm markers selected from the group consisting of CXCR4, SOX17, GATA-4, FOXA2, AFP, CER1, C-KIT, EPCAM, SNAIL, GSC E-Cad, and N-Cad, and wherein at least 50% of the differentiated mammalian cells produced in c) express the one or more definitive endoderm markers.

2. The method of claim 1, wherein incubating the cells for 16 to 60 hours in b) comprises dissociating the cells and plating the dissociated cells onto a coated culture dish and incubating the plated cells in the second stem cell culture medium prior to differentiating the incubated cells.

3. The method of claim 2, wherein the primed cells from b) are dissociated from the coated culture dish plate and formed into aggregates prior to c)
   i) where c) is performed on cells from b) in suspension culture, or
   ii) where c) is performed on aggregates that have been plated onto matrix-coated tissue culture plates.

4. The method of claim 1, wherein the first stem cell medium and the second stem cell medium comprise Dulbecco's minimal essential medium and further comprise at least one of vitamins, trace elements, selenium, insulin, lipids, β-mercaptoethanol, non-essential amino acids, antibiotics, bFGF, B27, or N2.

5. The method of claim 1, wherein the first stem cell medium and the second stem cell medium comprise a mixture of F-12 and Dulbecco's Modified Eagle's Medium (DMEM) and further comprise at least one of salts, vitamins, trace elements, proteins, selenium, insulin, lipids, β-mercaptoethanol, amino acids, or antibiotics.

6. The method of claim 1, wherein the first stem cell medium that maintains pluripotency comprises:
   (a) a mixture of F-12 and Dulbecco's Modified Eagle's Medium (DMEM), NaHCO$_3$, L-ascorbic acid, selenium, transferrin, insulin, FGF2, TGF-beta, bovine serum albumin, glutathione, beta-mercaptoethanol, pipecolic acid, γ-Aminobutyric acid (GABA), lithium chloride and defined lipids; or
   (b) a mixture of F-12 and Dulbecco's Modified Eagle's Medium (DMEM), NaHCO$_3$, L-ascorbic acid, selenium, transferrin, insulin, FGF2 and TGF-beta.

7. The method of claim 1, wherein the pluripotent stem cells are human pluripotent stem cells.

8. The method of claim 1, wherein the pluripotent stem cells are induced pluripotent stem cells or embryonic stem cells.

9. The method of claim 1, wherein the osmolality of the second stem cell medium is 350-450 mOsm/kg.

10. The method of claim 1, wherein the osmolality of the second stem cell medium is about 365 mOsm/kg.

11. The method of claim 1, wherein the endodermal progenitor cells are further differentiated to form pancreatic cells, respiratory cells, intestinal cells or liver cells.

12. The method of claim 1, wherein the differentiation medium has an osmolality of 260-280 mOsm/kg.

13. The method of claim 1, wherein the osmolality of the first stem cell medium, the second stem cell medium, and/or the differentiation medium is manipulated through the addition of a concentrated supplement.

14. The method of claim 13, wherein the concentrated supplement comprises a physiological diluent and a salt.

15. The method of claim 14, further comprising a protein.

16. The method of claim 15, wherein the protein comprises albumin.

17. The method of claim 16, wherein the albumin is derived from an animal source.

18. The method of claim 16 wherein the albumin is derived from a recombinant source.

19. The method of claim 18 wherein the albumin is human recombinant albumin.

20. The method of claim 14 wherein the salt is sodium chloride.

21. The method of claim 1, wherein b) comprises priming the pluripotent stem cells for 48 to 60 hours.

22. The method of claim 1, wherein b) comprises priming the pluripotent stem cells for 24 to 60 hours.

23. The method of claim 1, wherein the incubation of the cells in the second stem cell medium in b) comprises:
   i) priming the pluripotent stem cells for at least 24 hours as adherent aggregates;
   ii) dissociating the primed cells;
   iii) plating the dissociated cells as single cells onto a coated culture plate; and
   iv) continuing to incubate the cells in the second stem cells medium for at least 12 hours.

24. The method of claim 1, wherein the differentiation medium of c) comprises at least one of a TGF-beta signaling agonist and a WNT signaling agonist.

25. The method of claim 1, wherein the first stem cell medium has an osmolality of 290-310 mOsm/kg.

26. The method of claim 1, further comprising dissociating the cells of a) prior to b).

27. The method of claim 26, wherein the incubation of the cells in the second stem cell medium for 16 to 60 hours in b) comprises:
   i) priming the dissociated cells in a microwell device to form aggregates and continuing the priming in the microwell device in the second stem cell culture medium;
   ii) priming the dissociated cells in the second stem cell culture medium in a microwell device to form aggregates and releasing the aggregates from the microwell device;
   iii) priming the dissociated cells in suspension in the second stem cell culture medium for followed by dissociating the primed cells and adhering onto coated culture dishes and priming in the second stem cell culture medium; or
   iv) adhering the dissociated cells onto coated culture dishes or feeders and priming in the second stem cell culture medium.

28. The method of claim 1, wherein the primed cells are pluripotent.

* * * * *

UNITED STATES PATENT AND TRADEMARK OFFICE
CERTIFICATE OF CORRECTION

PATENT NO.         : 9,708,582 B2
APPLICATION NO.    : 13/829783
DATED              : July 18, 2017
INVENTOR(S)        : Alexandra A. Blak, Sharon A. Louis and Michael John Riedel It is certified that error appears in the above-identified patent and that said Letters Patent is hereby corrected as shown below:

In the Claims

Column 74, Claim 1, Line 61:
Please delete "GSC E-Cad" and insert therefor --GSC, E-Cad--.

Signed and Sealed this
Twenty-seventh Day of February, 2018

Andrei Iancu
*Director of the United States Patent and Trademark Office*